United States Patent
Shen et al.

(10) Patent No.: US 9,365,852 B2
(45) Date of Patent: Jun. 14, 2016

(54) COMPOSITIONS AND METHODS RELATED TO MIRNA MODULATION OF NEOVASCULARIZATION OR ANGIOGENESIS

(71) Applicant: Mirna Therapeutics, Inc., Austin, TX (US)

(72) Inventors: Jikui Shen, Dundlak, MD (US); Kevin Kelnar, Kyle, TX (US); Jeffrey Shelton, Buda, TX (US); David Brown, Austin, TX (US); Peter Campochiaro, Baltimore, MD (US)

(73) Assignee: MIRNA THERAPEUTICS, INC., Austin, TX (US)

( * ) Notice: Subject to any disclaimer, the term of this patent is extended or adjusted under 35 U.S.C. 154(b) by 0 days.

(21) Appl. No.: 14/704,458

(22) Filed: May 5, 2015

(65) Prior Publication Data
US 2015/0344880 A1  Dec. 3, 2015

Related U.S. Application Data

(60) Continuation of application No. 13/602,933, filed on Sep. 4, 2012, now abandoned, which is a division of application No. 12/437,899, filed on May 8, 2009, now Pat. No. 8,258,111.

(60) Provisional application No. 61/051,519, filed on May 8, 2008.

(51) Int. Cl.
| | |
|---|---|
| *C07H 21/02* | (2006.01) |
| *C07H 21/04* | (2006.01) |
| *A61K 48/00* | (2006.01) |
| *C12N 15/113* | (2010.01) |
| *C12Q 1/68* | (2006.01) |

(52) U.S. Cl.
CPC ............ *C12N 15/113* (2013.01); *C12Q 1/6809* (2013.01); *C12Q 1/6883* (2013.01); *C12N 2310/11* (2013.01); *C12N 2310/141* (2013.01); *C12N 2310/32* (2013.01); *C12N 2310/351* (2013.01); *C12N 2320/30* (2013.01); *C12Q 2600/106* (2013.01); *C12Q 2600/158* (2013.01); *C12Q 2600/178* (2013.01)

(58) Field of Classification Search
CPC .............................. A61K 48/00; C12N 15/113
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,876,187 A | 10/1989 | Duck et al. |
| 4,999,290 A | 3/1991 | Lee |
| 5,011,769 A | 4/1991 | Duck et al. |
| 5,188,934 A | 2/1993 | Menchen et al. |
| 5,256,555 A | 10/1993 | Milburn et al. |
| 5,260,191 A | 11/1993 | Yang |
| 5,262,311 A | 11/1993 | Pardee et al. |
| 5,366,860 A | 11/1994 | Bergot et al. |
| 5,432,272 A | 7/1995 | Benner |
| 5,486,603 A | 1/1996 | Buhr |
| 5,538,848 A | 7/1996 | Livak et al. |
| 5,543,296 A | 8/1996 | Sobol et al. |
| 5,545,522 A | 8/1996 | Van Gelder et al. |
| 5,660,988 A | 8/1997 | Duck et al. |
| 5,723,591 A | 3/1998 | Livak et al. |
| 5,739,169 A | 4/1998 | Ocain et al. |
| 5,766,888 A | 6/1998 | Sobol et al. |
| 5,800,996 A | 9/1998 | Lee et al. |
| 5,801,005 A | 9/1998 | Cheever et al. |
| 5,801,155 A | 9/1998 | Kutyavin et al. |
| 5,824,311 A | 10/1998 | Greene et al. |
| 5,830,880 A | 11/1998 | Sedlacek et al. |
| 5,847,162 A | 12/1998 | Lee et al. |
| 5,859,221 A | 1/1999 | Cook et al. |
| 5,861,245 A | 1/1999 | McClelland et al. |
| 5,863,727 A | 1/1999 | Lee et al. |
| 5,871,697 A | 2/1999 | Rothberg et al. |
| 5,898,031 A | 4/1999 | Crooke |
| 5,925,517 A | 7/1999 | Tyagi et al. |
| 5,936,087 A | 8/1999 | Benson et al. |
| 5,942,398 A | 8/1999 | Tartaglia et al. |
| 5,945,526 A | 8/1999 | Lee et al. |

(Continued)

FOREIGN PATENT DOCUMENTS

| | | |
|---|---|---|
| EP | 0416817 A2 | 3/1991 |
| EP | 0870842 A2 | 10/1998 |

(Continued)

OTHER PUBLICATIONS

Aaboe et al. Vitronectin in human breast carcinomas. Biochem. Biophys. Acta. 1638 (1):72-82, 2003.
Aagaard et al. An inflammatory role for the mammalian carboxypeptidase inhibitor latexin: relationship to cystatins and the tumor suppressor TIG1. Structure (Camb), 13: 309-317, 2005.
Abuharbeid et al. The fibroblast growth factor-binding protein FGF-BP. Int. J. Biochem. Cell Biol., 38(9):1463-1468, 2006.
Adams et al. Infrequent mutation of TRAIL receptor 2 (TRAIL-R2/DR5) in transitional cell carcinoma of the bladder with 8p21 loss of heterozygosity. Cancer Lett. 220 (2): 137-144, 2005.
Afanasyeva et al. New miRNAs cloned from neuroblastoma. BMC Genomics, 9(1):52, 2008.

(Continued)

*Primary Examiner* — Amy Bowman
(74) *Attorney, Agent, or Firm* — Wilson, Sonsini, Goodrich & Rosati

(57) ABSTRACT

The present invention concerns methods and compositions for diagnosing and/or treating vascular diseases including cancer, cardiac diseases, vascular diseases of the eye, and inflammatory diseases. The methods involve measuring the levels of one or multiple miRNAs in patient samples and using the test results to diagnose and/or predict an optimal treatment regimen for the patient. Compositions described in the invention include nucleic acids that function as miRNAs or miRNA inhibitors that can be introduced to a patient to reduce or increase vascularization as needed.

6 Claims, 8 Drawing Sheets

(56) References Cited

U.S. PATENT DOCUMENTS

| | | |
|---|---|---|
| 5,965,364 A | 10/1999 | Benner |
| 5,976,567 A | 11/1999 | Wheeler et al. |
| 5,998,203 A | 12/1999 | Matulic-Adamic et al. |
| 6,001,983 A | 12/1999 | Benner |
| 6,004,755 A | 12/1999 | Wang |
| 6,008,379 A | 12/1999 | Benson et al. |
| 6,020,481 A | 2/2000 | Benson et al. |
| 6,037,129 A | 3/2000 | Cole et al. |
| 6,040,138 A | 3/2000 | Lockhart et al. |
| 6,051,719 A | 4/2000 | Benson et al. |
| 6,057,105 A | 5/2000 | Hoon et al. |
| 6,084,102 A | 7/2000 | Kutyavin et al. |
| 6,096,314 A | 8/2000 | Cohen et al. |
| 6,103,476 A | 8/2000 | Tyagi et al. |
| 6,107,094 A | 8/2000 | Crooke |
| 6,111,095 A | 8/2000 | Benseler et al. |
| 6,132,997 A | 10/2000 | Shannon |
| 6,140,054 A | 10/2000 | Wittwer et al. |
| 6,140,500 A | 10/2000 | Yan et al. |
| 6,150,097 A | 11/2000 | Tyagi et al. |
| 6,153,737 A | 11/2000 | Manoharan et al. |
| 6,174,670 B1 | 1/2001 | Wittwer et al. |
| 6,184,037 B1 | 2/2001 | Rolland et al. |
| 6,191,278 B1 | 2/2001 | Lee et al. |
| 6,232,066 B1 | 5/2001 | Felder et al. |
| 6,238,869 B1 | 5/2001 | Kris et al. |
| 6,287,792 B1 | 9/2001 | Pardridge et al. |
| 6,344,316 B1 | 2/2002 | Lockhart et al. |
| 6,355,421 B1 | 3/2002 | Coull et al. |
| 6,383,752 B1 | 5/2002 | Agrawal et al. |
| 6,418,382 B2 | 7/2002 | Rothberg et al. |
| 6,435,245 B1 | 8/2002 | Sette et al. |
| 6,458,382 B1 | 10/2002 | Herweijer et al. |
| 6,458,533 B1 | 10/2002 | Felder et al. |
| 6,476,205 B1 | 11/2002 | Buhr et al. |
| 6,485,901 B1 | 11/2002 | Gildea et al. |
| 6,506,559 B1 | 1/2003 | Fire et al. |
| 6,511,832 B1 | 1/2003 | Guarino et al. |
| 6,548,250 B1 | 4/2003 | Sorge |
| 6,573,048 B1 | 6/2003 | VanAtta et al. |
| 6,573,099 B2 | 6/2003 | Graham |
| 6,586,218 B2 | 7/2003 | Milburn et al. |
| 6,586,219 B2 | 7/2003 | Milburn et al. |
| 6,589,743 B2 | 7/2003 | Sorge |
| 6,590,091 B2 | 7/2003 | Albagli et al. |
| 6,593,091 B2 | 7/2003 | Keys et al. |
| 6,596,490 B2 | 7/2003 | Dattagupta |
| 6,610,663 B2 * | 8/2003 | Cook ............... A61K 48/00 435/6.16 |
| 6,706,480 B1 | 3/2004 | Armour |
| 6,720,138 B2 | 4/2004 | Sharma et al. |
| 6,723,509 B2 | 4/2004 | Ach |
| 6,730,477 B1 | 5/2004 | Sun et al. |
| 6,787,335 B2 | 9/2004 | Salceda et al. |
| 6,797,471 B2 | 9/2004 | Katz et al. |
| 6,815,432 B2 | 11/2004 | Wheeler et al. |
| 6,858,225 B2 | 2/2005 | Semple et al. |
| 6,964,847 B1 | 11/2005 | Englert |
| 6,967,016 B2 | 11/2005 | Van et al. |
| 6,998,268 B2 | 2/2006 | Terada et al. |
| 7,001,724 B1 | 2/2006 | Greenfield |
| 7,005,261 B1 | 2/2006 | Lloyd et al. |
| 7,014,838 B2 | 3/2006 | Mueller et al. |
| 7,015,047 B2 | 3/2006 | Huang et al. |
| 7,056,704 B2 | 6/2006 | Tuschl et al. |
| 7,078,180 B2 | 7/2006 | Genetta |
| 7,078,196 B2 | 7/2006 | Tuschl et al. |
| 7,109,167 B2 | 9/2006 | Von Wronski et al. |
| 7,141,372 B2 | 11/2006 | Spivack et al. |
| 7,171,311 B2 | 1/2007 | Dai et al. |
| 7,192,586 B2 | 3/2007 | Bander |
| 7,205,105 B2 | 4/2007 | Belousov et al. |
| 7,232,806 B2 | 6/2007 | Tuschl et al. |
| 7,282,564 B2 | 10/2007 | Mello et al. |
| 7,297,480 B2 | 11/2007 | Vogt |
| 7,301,017 B2 * | 11/2007 | Kolesnick ............ A01K 67/0276 536/24.5 |
| 7,306,906 B2 | 12/2007 | Maruyama et al. |
| 7,307,067 B2 | 12/2007 | Sarnow et al. |
| 7,354,725 B2 | 4/2008 | Muraca |
| 7,365,058 B2 | 4/2008 | Stoffel et al. |
| 7,368,098 B2 | 5/2008 | Mueller et al. |
| 7,390,792 B2 | 6/2008 | Srivastava et al. |
| 7,402,389 B2 | 7/2008 | Mousses et al. |
| 7,452,987 B2 | 11/2008 | Giese et al. |
| 7,459,547 B2 | 12/2008 | Zamore et al. |
| 7,473,525 B2 | 1/2009 | Kreutzer et al. |
| 7,495,073 B2 | 2/2009 | Hsu et al. |
| 7,582,744 B2 | 9/2009 | Manoharan et al. |
| 7,592,441 B2 | 9/2009 | Bentwich et al. |
| 7,642,348 B2 | 1/2010 | Bentwich et al. |
| 7,655,785 B1 | 2/2010 | Bentwich |
| 7,683,036 B2 | 3/2010 | Esau et al. |
| 7,723,510 B1 | 5/2010 | Tuschl et al. |
| 7,960,359 B2 | 6/2011 | Brown et al. |
| 8,946,177 B2 † | 2/2015 | Brown |
| 2002/0006630 A1 | 1/2002 | Sirbasku |
| 2002/0037540 A1 | 3/2002 | Ali et al. |
| 2002/0065396 A1 | 5/2002 | Yang et al. |
| 2002/0065406 A1 | 5/2002 | Meyers |
| 2002/0068307 A1 | 6/2002 | Pluta et al. |
| 2002/0086356 A1 | 7/2002 | Tuschl et al. |
| 2002/0094546 A1 | 7/2002 | Shimkets et al. |
| 2002/0119156 A1 | 8/2002 | Chen et al. |
| 2002/0165189 A1 | 11/2002 | Crooke |
| 2003/0009295 A1 | 1/2003 | Markowitz et al. |
| 2003/0027783 A1 | 2/2003 | Zernicka-Goetz et al. |
| 2003/0031678 A1 | 2/2003 | Ali et al. |
| 2003/0033614 A1 | 2/2003 | French et al. |
| 2003/0084471 A1 | 5/2003 | Beach et al. |
| 2003/0099976 A1 | 5/2003 | Chang |
| 2003/0108923 A1 | 6/2003 | Tuschl et al. |
| 2003/0124114 A1 | 7/2003 | McIntire et al. |
| 2003/0157030 A1 | 8/2003 | Davis et al. |
| 2003/0170623 A1 | 9/2003 | Chen et al. |
| 2003/0175768 A1 | 9/2003 | Carson et al. |
| 2003/0180298 A1 | 9/2003 | Old et al. |
| 2003/0204322 A1 | 10/2003 | Loehrlein et al. |
| 2003/0215842 A1 | 11/2003 | Sledziewski et al. |
| 2004/0001841 A1 | 1/2004 | Nagavarapu et al. |
| 2004/0010001 A1 | 1/2004 | Au et al. |
| 2004/0029121 A1 | 2/2004 | Cottrell et al. |
| 2004/0029128 A1 | 2/2004 | Cottrell et al. |
| 2004/0053411 A1 | 3/2004 | Cullen et al. |
| 2004/0058373 A1 | 3/2004 | Winkler et al. |
| 2004/0063197 A1 | 4/2004 | Tilles et al. |
| 2004/0063654 A1 | 4/2004 | Davis et al. |
| 2004/0072164 A1 | 4/2004 | Maruyama et al. |
| 2004/0086504 A1 | 5/2004 | Sampath et al. |
| 2004/0110191 A1 | 6/2004 | Winkler et al. |
| 2004/0114800 A1 | 6/2004 | Ponomarev et al. |
| 2004/0115630 A1 | 6/2004 | Olek et al. |
| 2004/0115671 A1 | 6/2004 | Zlokovic et al. |
| 2004/0147027 A1 | 7/2004 | Troy et al. |
| 2004/0152112 A1 | 8/2004 | Croce et al. |
| 2004/0166511 A1 | 8/2004 | Clasina et al. |
| 2004/0175732 A1 | 9/2004 | Rana |
| 2004/0203145 A1 | 10/2004 | Zamore et al. |
| 2004/0214198 A1 | 10/2004 | Rana |
| 2004/0215651 A1 | 10/2004 | Markowitz et al. |
| 2004/0224337 A1 | 11/2004 | Foehr et al. |
| 2004/0229211 A1 | 11/2004 | Yeung |
| 2004/0236516 A1 | 11/2004 | Brandon |
| 2004/0243362 A1 | 12/2004 | Liebman |
| 2004/0259247 A1 | 12/2004 | Tuschl et al. |
| 2005/0020521 A1 | 1/2005 | Rana |
| 2005/0026278 A1 | 2/2005 | Tuschl et al. |
| 2005/0033030 A1 | 2/2005 | Lo et al. |
| 2005/0037362 A1 | 2/2005 | Remacle et al. |
| 2005/0059024 A1 | 3/2005 | Conrad |
| 2005/0065333 A1 | 3/2005 | Seth |
| 2005/0074788 A1 | 4/2005 | Dahlberg et al. |
| 2005/0075492 A1 | 4/2005 | Chen et al. |
| 2005/0095646 A1 | 5/2005 | Sherman |

(56) References Cited

U.S. PATENT DOCUMENTS

| | | |
|---|---|---|
| 2005/0112604 A1 | 5/2005 | Fujimoto et al. |
| 2005/0125161 A1 | 6/2005 | Cairney et al. |
| 2005/0130170 A1 | 6/2005 | Harvey et al. |
| 2005/0130172 A1 | 6/2005 | Beard et al. |
| 2005/0142556 A1 | 6/2005 | Hoon et al. |
| 2005/0153337 A1 | 7/2005 | Manoharan |
| 2005/0176018 A1 | 8/2005 | Thompson et al. |
| 2005/0181382 A1 | 8/2005 | Zamore et al. |
| 2005/0182005 A1 | 8/2005 | Tuschl et al. |
| 2005/0186018 A1 | 8/2005 | Byun |
| 2005/0186586 A1 | 8/2005 | Zamore et al. |
| 2005/0208493 A1 | 9/2005 | Alon |
| 2005/0234006 A1 | 10/2005 | Tuschl et al. |
| 2005/0234007 A1 | 10/2005 | Tuschl et al. |
| 2005/0261218 A1 | 11/2005 | Esau et al. |
| 2005/0266418 A1 | 12/2005 | Chen et al. |
| 2005/0287539 A1 | 12/2005 | Labourier et al. |
| 2006/0051768 A1 | 3/2006 | Hoon et al. |
| 2006/0078894 A1 | 4/2006 | Winkler et al. |
| 2006/0088521 A1 | 4/2006 | Mahadevan |
| 2006/0095980 A1 | 5/2006 | Petitte et al. |
| 2006/0105350 A1 | 5/2006 | Qiao et al. |
| 2006/0105360 A1 | 5/2006 | Croce et al. |
| 2006/0134639 A1 | 6/2006 | Huffel et al. |
| 2006/0134661 A1 | 6/2006 | Essner |
| 2006/0154275 A1 | 7/2006 | Sgarlato et al. |
| 2006/0165659 A1 | 7/2006 | Croce et al. |
| 2006/0183128 A1 | 8/2006 | Berlin et al. |
| 2006/0185026 A1 | 8/2006 | Sacktor et al. |
| 2006/0185027 A1 | 8/2006 | Bartel et al. |
| 2006/0189557 A1 | 8/2006 | Slack et al. |
| 2006/0195269 A1 | 8/2006 | Yeatman et al. |
| 2006/0210979 A1 | 9/2006 | Yang et al. |
| 2006/0247193 A1 | 11/2006 | Taira et al. |
| 2006/0252057 A1 | 11/2006 | Raponi et al. |
| 2006/0258566 A1 | 11/2006 | Von et al. |
| 2006/0271309 A1 | 11/2006 | Showe et al. |
| 2006/0292616 A1 | 12/2006 | Neely et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0009484 A1 | 1/2007 | Hunt et al. |
| 2007/0025997 A1 | 2/2007 | Nagavarapu et al. |
| 2007/0031840 A1 | 2/2007 | Klussmann et al. |
| 2007/0031873 A1 | 2/2007 | Wang et al. |
| 2007/0041934 A1 | 2/2007 | William et al. |
| 2007/0048758 A1 | 3/2007 | Lokhov et al. |
| 2007/0050146 A1 | 3/2007 | Bentwich et al. |
| 2007/0054287 A1 | 3/2007 | Bloch |
| 2007/0065844 A1 | 3/2007 | Golub et al. |
| 2007/0072204 A1 | 3/2007 | Hannon et al. |
| 2007/0093445 A1 | 4/2007 | Tuschl et al. |
| 2007/0099196 A1 | 5/2007 | Kauppinen et al. |
| 2007/0161004 A1 | 7/2007 | Brown et al. |
| 2007/0213292 A1 | 9/2007 | Stoffel et al. |
| 2007/0259827 A1 | 11/2007 | Aronin et al. |
| 2007/0287179 A1 | 12/2007 | Tuschl et al. |
| 2007/0299030 A1 | 12/2007 | Dmitrovsky et al. |
| 2008/0076674 A1 | 3/2008 | Litman et al. |
| 2008/0132461 A1 | 6/2008 | Tuschl et al. |
| 2008/0171667 A1 | 7/2008 | Brown et al. |
| 2008/0171715 A1 | 7/2008 | Brown et al. |
| 2008/0176766 A1 | 7/2008 | Brown et al. |
| 2008/0182237 A1 | 7/2008 | Bentwich et al. |
| 2008/0182245 A1 | 7/2008 | Brown et al. |
| 2008/0261908 A1 | 10/2008 | Croce et al. |
| 2008/0269147 A1 | 10/2008 | Tuschl et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0029932 A1 | 1/2009 | Voinnet et al. |
| 2009/0075258 A1 | 3/2009 | Latham et al. |
| 2009/0092974 A1 | 4/2009 | Davison et al. |
| 2009/0186353 A1 | 7/2009 | Aharonov et al. |
| 2009/0186843 A1 | 7/2009 | Tuschl et al. |
| 2009/0281167 A1 | 11/2009 | Shen et al. |
| 2010/0087507 A1 | 4/2010 | Ochiya et al. |
| 2010/0144850 A1 | 6/2010 | Croce |
| 2010/0203544 A1 | 8/2010 | Croce et al. |
| 2010/0234241 A1 | 9/2010 | Croce et al. |
| 2010/0257618 A1 | 10/2010 | Croce et al. |
| 2010/0286232 A1 | 11/2010 | Schmittgen et al. |

FOREIGN PATENT DOCUMENTS

| | | |
|---|---|---|
| EP | 0921195 A1 | 6/1999 |
| EP | 1627925 A1 | 2/2006 |
| EP | 2285960 A2 | 2/2011 |
| FR | 2877350 A1 | 5/2006 |
| JP | 2005296014 A | 10/2005 |
| WO | WO-9321329 | 10/1993 |
| WO | WO-9727317 | 7/1997 |
| WO | WO-9743450 | 11/1997 |
| WO | WO-9745539 | 12/1997 |
| WO | WO-9808973 | 3/1998 |
| WO | WO-9921881 | 5/1999 |
| WO | WO-9923256 | 5/1999 |
| WO | WO-9936760 | 7/1999 |
| WO | WO-0005409 A1 | 2/2000 |
| WO | WO-0024939 A1 | 5/2000 |
| WO | WO-0044895 A1 | 8/2000 |
| WO | WO-0056748 A1 | 9/2000 |
| WO | WO-0066604 A2 | 11/2000 |
| WO | WO-0075356 A1 | 12/2000 |
| WO | WO-0168255 A2 | 9/2001 |
| WO | WO-0175164 A2 | 10/2001 |
| WO | WO-0200169 A2 | 1/2002 |
| WO | WO-0244321 A2 | 6/2002 |
| WO | WO-02064835 A2 | 8/2002 |
| WO | WO-03020898 A2 | 3/2003 |
| WO | WO-03020931 A2 | 3/2003 |
| WO | WO-03022421 A2 | 3/2003 |
| WO | WO-03023058 A2 | 3/2003 |
| WO | WO-03029459 A2 | 4/2003 |
| WO | WO-03029485 A2 | 4/2003 |
| WO | WO-03040410 A1 | 5/2003 |
| WO | WO-03053586 A1 | 7/2003 |
| WO | WO-03066906 A2 | 8/2003 |
| WO | WO-03067217 A2 | 8/2003 |
| WO | WO-03076928 A1 | 9/2003 |
| WO | WO-03087297 A2 | 10/2003 |
| WO | WO-03091426 A1 | 11/2003 |
| WO | WO-03093810 A1 | 11/2003 |
| WO | WO-03100012 A2 | 12/2003 |
| WO | WO-03100448 A1 | 12/2003 |
| WO | WO-2004020085 A1 | 3/2004 |
| WO | WO-2004027093 A1 | 4/2004 |
| WO | WO-2004029212 A2 | 4/2004 |
| WO | WO-2004043387 A2 | 5/2004 |
| WO | WO-2004046324 A2 | 6/2004 |
| WO | WO-2004050125 A1 | 6/2004 |
| WO | WO-2004057017 A2 | 7/2004 |
| WO | WO-2004066183 A2 | 8/2004 |
| WO | WO-2004074509 A2 | 9/2004 |
| WO | WO-2004076622 A2 | 9/2004 |
| WO | WO-2005013901 A2 | 2/2005 |
| WO | WO-2005078139 A2 | 8/2005 |
| WO | WO-2005079397 A2 | 9/2005 |
| WO | WO-2005116261 A2 | 12/2005 |
| WO | WO-2005118806 A2 | 12/2005 |
| WO | WO-2006028967 A2 | 3/2006 |
| WO | WO-2006033928 A2 | 3/2006 |
| WO | WO-2006101173 A1 | 9/2006 |
| WO | WO-2006108718 A1 | 10/2006 |
| WO | WO-2006113679 A2 | 10/2006 |
| WO | WO-2006119365 A2 | 11/2006 |
| WO | 2006/137941 A2 † | 12/2006 |
| WO | WO-2006128245 A1 | 12/2006 |
| WO | WO-2006135765 A1 | 12/2006 |
| WO | WO-2006137941 A2 | 12/2006 |
| WO | WO-2007016548 A2 | 2/2007 |
| WO | WO-2007033023 A2 | 3/2007 |
| WO | WO-2007073737 A1 | 7/2007 |

(56) References Cited

FOREIGN PATENT DOCUMENTS

| | | |
|---|---|---|
| WO | WO-2007081720 A2 | 7/2007 |
| WO | WO-2007081740 A2 | 7/2007 |
| WO | WO-2007087113 A2 | 8/2007 |
| WO | WO-2008014008 A2 | 1/2008 |
| WO | WO-2008095096 A9 | 10/2008 |
| WO | WO-2008136971 A1 | 11/2008 |
| WO | WO-2008137867 A2 | 11/2008 |

OTHER PUBLICATIONS

Agrawal and Kandimalla. Antisense therapeutics: is it as simple as complementary base recognition. Molecular Medicine Today, 6:72-81, 2000.

Agrawal and Syngal. Colon cancer screening strategies. Curr Opin Gastroenterol, 21(1):59-63, 2005.

Aiello et al. Suppression of retinal neovascularization in vivo by inhibition of vascular endothelial growth factor (VEGF) using soluble VEGF-receptor chimeric proteins. Proc. Natl. Acad. Sci. USA. 92(23):10457-10461, 1995.

Akao et al. let-7 microRNA functions as a potential growth suppressor in human colon cancer cells. Biol. Pharm. Bull, 29(5):903-906, 2006.

Akao et al. MicroRNAs 143 and 145 are possible common onco-microRNAs in human cancers. Oncology Reports, 16:845-850, 2006.

Akiba et al. Expression and function of interleukin-8 in human hepatocellular carcinoma. Int. J. Oncol., 18 (2): 257-264, 2001.

Alevizos et al. Oral cancer in vivo gene expression profiling assisted by laser capture microdissection and microarray analysis. Oncogene, 20(43):6196-6204, 2001.

Al-Hajj et al. Prospective identification of tumorigenic breast cancer cells. Proc. Natl. Acad. Sci. U S A, 100(7):3983-8, 2003.

Allawi et al. Quantitation of MicroRNAs using a modified Invader assay. RNA, 10:1153-1161, 2004.

Altucci and Gronemeyer. The promise of retinoids to fight against cancer. Nat. Rev. Cancer, 1:181-193, 2001.

Altucci and Gronomeyer. Retinoids and TRAIL: two cooperating actors to fight against cancer. Vitam. Horn. 67:319-345, 2004.

Ambion, Inc. mMessage mMachine®. High Yield Capped RNA Transcription Kit, Catalog #1340, 1344, 1348; pp. 1-8.

Ambion, Inc. mMessage mMachine®. Instruction Manual, Catalog #1340, 1344, 1348; pp. 1-31.

Ambros et al. A uniform system for microRNA annotation. RNA, 9(3):277-279, 2003.

Ambros. microRNAs: tiny regulators with great potential. Cell, 107(7):823-826, 2001.

Amendment and Response to Office Action filed Sep. 12, 2012, in U.S. Appl. No. 13/299,255.

Anatharaman and Aravind. Evolutionary history, structural features and biochemical diversity of the N1pC/P60 superfamily of enzymes. Genome Biol., 4:R11, 2003.

Ando et al. Polo-like kinase 1 (Plkl) inhibits p53 function by physical interaction and phosphorylation. J. Biol. Chem., 279 (24):25549-25561, 2004.

Aoki et al. Proteasomal degradation of the FoxOl transcriptional regulator in cells transformed by the P3k and Akt oncoproteins. Proc Natl Aced Sci USA. 101(37):13613-13617, 2004.

Armour et al. Measurement of locus copy number by hybridisation with amplifiable probes. Nucleic Acids Research, 28(2):605-609, 2000.

Association of Directors of Anatomic and Surgical Pathology. Recommendations for the reporting of resected large intestinal carcinomas. Association of directors of anatomic and surgical pathology. Am. J. Clin. Pathol. 106 (1): 12-15, 1996.

Astler and Coller. The prognostic significance of direct extension of carcinoma of the colon and rectum. Ann. Surg., 139: 846-852, 1954.

Asuragen, Inc. website. Asuragen's DiscovArray miRNA Expression Profiling Service. located athttp://www.asuragen.com/Services/solutions/discovarray.aspx, printed Mar. 6, 2009.

Austin and Cook. Increased expression of Mc1-1 is required for protection against serum starvation in phosphatase and tensin homologue on chromosome 10 null mouse embryonic fibroblasts, but repression of Bim is favored in human glioblastomas. J Biol Chem, 280(39):33280-33288, 2005.

Baba et al. Involvement of deregulated epiregulin expression in tumorigenesis in vivo through activated Ki-Ras signaling pathway in human colon cancer cells. Cancer Res, 60(24):6886-6889, 2000.

Bader and Vogt. An essential role for protein synthesis in oncogenic cellular transformation. Oncogene, 23(18):3145-3150, 2004.

Bader et al. Oncogenic Pl3K deregulates transcription and translation. Nat Rev Cancer, 5(12):921-929, 2005.

Bae et al. MCL-1S, a splicing variant of the antiapoptotic BCL-2 family member MCL-1, encodes a proapoptotic protein possessing only the BH3 domain. J. Biol. Chem., 275(33):25255-61, 2000.

Baffa et al. MicroRNA expression profiling of human metastatic cancers identifies cancer gene targets. J. Pathol., Epub Ahead of Print, 2009.

Bagga et al. Regulation by let-7 and lin-4 miRNAs results in target mRNA degradation. Cell, 122(4):553-563, 2005.

Bai et al. Downregulation of selective microRNAs in trigeminal ganglion neurons following inflammatory muscle pain. Mol Pain, 3:15, 2007.

Bandres et al. Identification by Real-time PCR of 13 mature microRNAs differentially expressed in colorectal cancer and non-tumoral tissues. Mol. Cancer, 5:29, 2006.

Bangoura et al. Expression of HIF-2alpha/EPAS1 in hepatocellular carcinoma. World J. Gastroenterol., 10(4):525-530, 2004.

Bao et al. Glioma stem cells promote radioresistance by preferential activation of the DNA damage response. Nature, 444(7120):756-60, 2006.

Barnetson et al. Genetic analysis of multiple sporadic colon carcinomas from a single patient. Int J Colorectal Dis, 15:83-86, 2000.

Bartel et al. Alternative and aberrant splicing of MDM2 mRNA in human cancer. Cancer Cell, 2(1):9-15, 2002.

Bartlett and Davis. Effect of siRNA nuclease stability on the in vitro and in vivo kinetics of siRNA-mediated gene silencing. Biotechnol. Bioeng. 97(4):909-921, 2007.

Bartlett et al. Impact of tumor-specific targeting on the biodistribution and efficacy of siRNA nanoparticles measured by multimodality in vivo imaging. 104(39):15549-15554, 2007.

Bartlett et al. Insights into the kinetics of siRNA-mediated gene silencing from live-cell and live-animal bioluminescent imaging. Nucleic Acids Research, 34(1):322-333, 2006.

Barton et al. Angiogenic protein expression in advanced epithelial ovarian cancer. Clin. Cancer Res., 3 (9):1579-1586, 1997.

Basturk et al. MicroRNA expression in androgen independent and metastatic prostate cancer. Modern Pathology, Abstract No. 669, 21(Suppl. 1):148A, 2008.

Bedell et al. Amplification of human papillomavirus genomes in vitro is dependent on epithelial differentiation. J Virol. 65(5):2254-60, 1991.

Beeram et al. Raf: a strategic target for therapeutic development against cancer. J Clin Oncol, 23(27):6771-6790, 2005.

Beier et al. CD133(+) and CD133(−) glioblastoma-derived cancer stem cells show differential growth characteristics and molecular profiles. Cancer Res., 67(9):4010-5, 2007.

Bell and Dutta. DNA replication in eukaryotic cells. Annu Rev Biochem, 71:333-374, 2002.

Bello et al. Androgen responsive adult human prostatic epithelial cell lines immortalized by human papillomavirus 18. Carcinogenesis, 18(6):1215-1223, 1997.

Bellovin et al. Reciprocal regulation of RhoA and RhoC characterizes the EMT and identifies RhoC as a prognostic marker of colon carcinoma. Oncogene, 25 (52):6959-6967, 2006.

Bendtsen et al. Feature-based prediction of non-classical and leaderless protein secretion. Protein Eng. Des. Sel., 17:349-356, 2004.

Benlloch et al. Role of CEA, PLUNC and CK19 mRNA expression in lymph nodes from resected stage I non-small cell lung cancer (NSCLC) patients as markers of occult micrometastasis: A pilot study. Lung Cancer, Abstract No. P-649, 49(1):5289, 2005.

(56) References Cited

OTHER PUBLICATIONS

Ben-Porath et al. An embryonic stem cell-like gene expression signature in poorly differentiated aggressive human tumors. Nat. Genet., 40(5):499-507, 2008.
Bentwich et al. Identification of hundreds of conserved and nonconserved human microRNAs. Nat Genet., 37(7):766-770, 2005.
Berezikov et al, Cell. Phylogenetic shadowing and computational identification of human microRNA genes. 120(1):21-24, 2005.
Berman et al. Medulloblastoma growth inhibition by hedgehog pathway blockade. Science, 297(5586):1559-61, 2002.
Bertagnolli et al. Sentinel node staging of resectable colon cancer: results of a multicenter study. Ann. Surg., 240(4):624-630, 2004.
Billottet et al. A selective inhibitor of the pllOdelta isoform of PI 3-kinase inhibits AML cell proliferation and survival and increases the cytotoxic effects of VP16. Oncogene, 25 (50):6648-6659, 2006.
Birchmeier et al. Met, metastasis, motility and more. Nat Rev Mol Cell Biol, 4(12):915-925, 2003.
Birnie et al. Gene expression profiling of human prostate cancer stem cells reveals a pro-inflammatory phenotype and the importance of extracellular matrix interactions. Genome Biol., 9(5):R83. [Epub ahead of print], 2008.
Biswas et al. Transforming growth factor beta receptor type II inactivation promotes the establishment and progression of colon cancer. Cancer Res., 64 (14):4687-4692, 2004.
Bitomsky et al. Transformation suppressor protein Pdcd4 interferes with INK-mediated phosphorylation of c-Jun and recruitment of the coactivator p300 by c-Jun. Oncogene, 23(45):7484-93, 2004.
Black et al. Expression of cyclin D1, cyclin E, EGFR, UBE1L and K167 in paired benign and malignant lung tissues. Lung Cancer, 49:S289, Abstract P-650, 2005.
Blanc et al. Wnt-5a gene expression in malignant human neuroblasts. Cancer Lett. 228 (1-2): 117-123, 2005.
Blobe et al. Functional roles for the cytoplasmic domain of the type III transforming growth factor beta receptor in regulating transforming growth factor beta signaling. J Biol Chem, 276(27):24627-24637, 2001.
Blower et al. MicroRNAs modualte the chemosensitivity of tumor cells. Mol Cancer Ther, 7(1):1-9, 2008.
Boccaccio and Comoglio. Invasive growth: a MET-driven genetic programme for cancer and stem cells. Nat Rev Cancer, 6(8):637-645, 2006.
Bodner-Adler et al. Serum levels of angiogenin (ANG) in invasive cervical cancer and in cervical intraepithelial neoplasia (CIN). Anticancer Res., 21 (1B):809-812, 2001.
Bommer et al. p53-mediated activation of miRNA34 candidate tumor-suppressor genes. Current Biology, 17:1298-1307, mailed 2007.
Bonci et al. The miR-15a-miR-16-1 cluster controls prostate cancer by targeting multiple oncogenic activities. Nature Medicine, 14(11):1271-1277, 2008.
Bonci et al. The miR-15A/miR-16-1 cluster controls prostate cancer progression by targeting multiple oncogenic activities. European Urology Supplements, Abstract No. 802, 7(3):271, 2008.
Bosch and de Sanjose. The epidemiology of human papillomavirus infection and cervical cancer. Dis Markers. 23(4):213-27, 2007.
Bostwick et al. Amphiregulin expression in prostatic intraepithelial neoplasia and adenocarcinoma: a study of 93 cases. Prostate, 58(2):164-168, 2004.
Bottoni et al. miR-15a and miR-16-1 Down-Regulation in Pituitary Adenomas. J Cell. Physiol., 204:280-285, 2005.
Boultwood et al. Low expression of the putative tumour suppressor gene gravin in chronic myeloid leukaemia, myelodysplastic syndromes and acute myeloid leukaemia. Br J Haematol, 126(4):508-511, 2004.
Bourguignon et al. Hyaluronan-CD44 interaction activates stem cell marker Nanog, Stat-3-mediated MDR1 gene expression, and ankyrin-regulated multidrug efflux in breast and ovarian tumor cells. J. Biol. Chem., 283(25):17635-51, 2008.
Braasch et al. RNA interference in mammalian cells by chemically-modified RNA. Biochemistry, 42:7967-7975, 2003.

Brazma and Vilo. Gene expression data analysis. FEBS Letters, 480:17-24, 2000.
Brennecke et al. Bantam encodes a developmentally regulated microRNA that controls cell proliferation and regulates the proapoptotic gene hid in *Drosophila*. Cell, 113:25-36, 2003.
Brioschi et al. Down-regulation of microRNAs 222/221 in acute myelogenous leukemia with deranged core-binding factor subunits. Neoplasia, 12(11):866-876, 2010.
Brothman et al. Metastatic properties of the human prostatic cell line, PPC-1, in athymic nude mice. J Urol., 145(5):1088-1091, 1991.
Brown and Regillo. Anti-VEGF agents in the treatment of neovascular age-related macular degeneration: applying clinical trial results to the treatment of everyday patients. Am. J Ophthalmol. 144(4):627-637, 2007.
Bullinger et al. Gene expression profiling in acute myeloid leukemia. Journal of Clinical Oncology, 23(26):6296-6305, 2005.
Burdy et al. Identifying patients with T3-T4 node-negative colon cancer at high risk of recurrence. Dis Colon Rectum, 44:1682-1688, 2001.
Bussing et al. let-7 microRNAs in development, stem cells and cancer. Trends in Molecular Medicine, 14(9):400-409, 2008.
Bustin et al. Real-time reverse transcription PCR (qRT-PCR) and its potential use in clinical diagnosis. Clinical Science, 109:365-379, 2005.
Byrd et al. Pretreatment cytogenetic abnormalities are predictive of induction success, cumulative incidence of relapse, and overall survival in adult patients with de novo acute myeloid leukemia: results from Cancer and Leukemia Group B (CALGB 8461) Blood, 100:4325-4336, 2002.
Cai et al. Human papillomavirus genotype 31 does not express detectable microRNA levels during latent or productive virus replication. J Virol. 80(21):10890-3, 2006.
Calin and Croce. Genomics of chronic lymphocytic leukemia microRNAs as new players with clinical significance. Seminars in Oncology, 33(2):167-173, 2006.
Calin and Croce. MicroRNA signatures in human cancers. Nat Rev Cancer, 6(11):857-866, 2006.
Calin and Croce. MicroRNA-cancer connection: the beginning of a new tale. Cancer Res., 66 (15):7390-7394, 2006.
Calin and Croce. MicroRNAs and chromosomal abnormalities in cancer cells. Oncogene, 25 (46):6202-6210, 2006.
Calin et al. A MicroRNA signature associated with prognosis and progression in chronic lymphocytic leukemia. New England Journal of Medicine, 353(17):1793-1801, 2005.
Calin et al. Frequent deletions and down-regulation of micro-RNA genes miR15 and miR16 at 13q14 in chronic lymphocytic leukemia. Proc. Natl. Acad. Sci. USA, 99:15524-15529, 2002.
Calin et al. Human microRNA genes are frequently located at fragile sites and genomic regions involved in cancers. PNAS, 101(9):2999-3004, 2004.
Calin et al. MicroRNA profiling reveals distinct signatures in B cell chronic lymphocytic leukemias. Proc Natl Acad Sci USA, 101(32):11755-11760, 2004.
Campochiaro and Hackett. Ocular neovascularization: a valuable model system. Oncogene, 22(42):6537-6548, 2003.
Cao et al. A functional study of miR-124 in the developing neural tube. Genes & Development, 21(5):531-536, 2007.
Carrano et al. SKP2 is required for ubiquitin-mediated degradation of the CDK inhibitor p27. Nat. Cell. Biol., 1 (4):193-199, 1999.
Carreiras et al. Expression and localization of alpha v integrins and their ligand vitronectin in normal ovarian epithelium and in ovarian carcinoma. Gynecol. Oncol., 62 (2):260-267, 1996.
Carreiras et al. Human ovarian adenocarcinoma cells synthesize vitronectin and use It to organize their adhesion. Gynecol. Oncol., 72 (3):312-322, 1999.
Carrington and Ambros. Role of MicroRNAs in Plant and Animal Development. Science; 301:336-338; 2003.
Carter and Brunet. FOXO transcription factors. Curr Biol, 17(4):R113-114, 2007.
Casanova et al. The class II tumor-suppressor gene RARRES3 is expressed in B cell lymphocytic leukemias and down-regulated with disease progression. Leukemia, 15 (10):1521-1526, 2001.

(56) References Cited

OTHER PUBLICATIONS

Caselitz et al. Malignant melanomas contain only the vimentin type of intermediate filaments. Virchows Arch A Pathol Anat Histopathol, 400(1):43-51, 1983.

Castillo et al. Amphiregulin contributes to the transformed phenotype of human hepatocellular carcinoma cells. Cancer Res., 66(12):6129-6138, 2006.

Caudy et al. Fragile X-related protein and VIG associate with the RNA interference machinery. Genes & Development, 16:2491-2496; 2002.

Chan et al. Downregulation of ID4 by promoter hypermethylation in gastric adenocarcinoma. Oncogene, 22 (44):6946-6953, 2003.

Chan et al. MicroRNA-21 is an antiapoptotic factor in human glioblastoma cells. Cancer Res., 65(14):6029-6033, 2005.

Chandler et al. Prevalent expression of fibroblast growth factor (FGF) receptors and FGF2 in human tumor cell lines. Int. J. Cancer, 81(3):451-458, 1999.

Chang et al. Elevated circulating level of osteopontin is associated with advanced disease state of non-small cell lung cancer. Lung Cancer, 57(3):373-380, 2007.

Chang et al. MicroRNAs act sequentially and asymmetrically to control chemosensory laterality in the nematode. Nature, 430(7001):785-789, 2004.

Chang et al. Transactivation of miR-34a by p53 broadly influences gene expression and promotes apoptosis. Mol. Cell., 26(5):745-752, 2007.

Chen et al. Identification of trophinin as an enhancer for cell invasion and a prognostic factor for early stage lung cancer. European Journal of Cancer, 43(4):782-790, 2007.

Chen et al. Loss of PDCD4 expression in human lung cancer correlates with tumour progression and prognosis, 1 Pathol. 200(5):640-646, 2003.

Chen et al. MicroRNAs modulate hematopoietic lineage differentiation. Science, 303(5654):83-86, 2004.

Chen et al. Real-time quantification of microRNAs by stem-loop RT-PCR. Nucleic Acids Research, 33(20):e179 (13 printed pages), 2005.

Chendrimada et al. MicroRNA silencing through RISC recruitment of eIF6. Nature, 447(7146):823-828, 2007.

Cheng et al. Antisense inhibition of human miRNAs and indications for an involvement of miRNA in cell growth and apoptosis. Nucleic Acids Res., 33(4):1290-1297, 2005.

Chiaretti et al. Gene expression profiling identifies a subset of adult T-cell acute lymphoblastic leukemia with myeloid-like gene features and over-expression of miR-223. Haematologica, 95(7):1114-1121, 2010.

Chieffi et al. Aurora B expression directly correlates with prostate cancer malignancy and influence prostate cell proliferation. Prostate, 66(3):326-333, 2006.

Chirila et al. The use of synthetic polymers for delivery of therapeutic antisense oligodeoxynucleotides. Biomaterials, 23:321-342, 2002.

Chmielarz et al. Prognostic factors for the time of occurrence and dynamics of distant metastases and local recurrences after radical treatment in patients with rectal cancer. Med Sci Monit., 7(6):1263-1269, 2001.

Choi et al. AKAP12/Gravin is inactivated by epigenetic mechanism in human gastric carcinoma and shows growth suppressor activity. Oncogene, 23(42):7095-7103, 2004.

Churg. Immunohistochemical staining for vimentin and keratin in malignant mesothelioma. Am J Surg Pathol, 9(5):360-365, 1985.

Ciafre et al. Extensive modulation of a set of microRNAs in primary glioblastoma. Biochem. Biophys. Res. Commun., 334(4):1351-1358, 2005.

Cimmino et al. miR-15 and miR-16 induce apoptosis by targeting BCL2. Proceedings of the National Academy of Sciences of the USA, 102(39):13944-13949, 2005.

Ciocca et al. Heat shock portein hsp70 in patients with axillary lymph node-negative breast cancer: Prognostic implications. Journal of the National Cancer Institute, 85(7):570-574, 1993.

Cipriano and Chen. Insensitivity to growth inhibition by TGF-betal correlates with a lack of inhibition of the CDK2 activity in prostate carcinoma cells. Oncogene, 17(12):1549-1556, 1998.

Claudio et al. Expression of cell-cycle-regulated proteins pRb2/p130, p107, p27(kip1), p53, mdm-2, andKi-67 (MIB-1) in prostatic gland adenocarcinoma. Clin Cancer Res, 8(6):1808-1815, 2002.

Clement et al. Hedgehog-GLI1 signaling regulates human glioma growth, cancer stem cell self-renewal, and tumorigenicity. Curr. Biol., 17(2): 165-72, 2007.

Clifford et al. Human papillomavirus types in invasive cervical cancer worldwide: a meta-analysis. Br. J. Cancer, 88(1):63-73, 2003.

Coello et al. Prognostic significance of micrometastasis in non-small-cell lung cancer. Clin. Lung Cancer, 5:214-225, 2004.

Cogliano et al. Carcinogenicity of human papillomaviruses. Lancet Oncol. 6(4):204, 2005.

Cohen et al. Expression of a down-regulated target, SSeCKS, reverses v-Jun-induced transformation of 1OT1/2 murine fibroblasts. Oncogene, 20(2):141-146, 2001.

Cohen et al. Prognosis of node-positive colon cancer. Cancer, 67(7):1859-1861, 1991.

Coleman et al. Superior 5' homogeneity of RNA from ATP-initiated transcription under T7 D2.5 promoter. Nucleic Acids Research, 32(1):e14, 2004.

Coll et al. Molecular cloning of the avian acute transforming retrovirus MH2 reveals a novel cell-derived sequence (v-mil) in addition to the myc oncogene. Embo J, 2(12):2189-2194, 1983.

Collins et al. Prospective identification of tumorigenic prostate cancer stem cells, Cancer Res., 65(23):10946-51, 2005.

Conaco et al. Reciprocal actions of REST and a microRNA promote neuronal identity, PNAS, 103(7):2422-2427, 2006.

Cooper et al. Molecular cloning of a new transforming gene from a chemically transformed human cell line. Nature, 311(5981):29-33, 1984.

Costello et al. Cyclin-dependent kinase 6 (CDK6) amplification in human gliomas identified using two-dimensional separation of genomic DNA, Cancer Res, 57(7):1250-1254, 1997.

Costinean et al. Pre-B cell proliferation and lymphoblastic leukemia/high-grade lymphoma in Eμ-miR155 transgenic mice. Proc. Natl. Acad. Sci. USA, 103(18):7024-7029, 2006.

Cox. Epidemiology and natural history of HPV. J. Fain. Pract. Suppl:3-9, 2006.

Cox et al. Significance of sentinel lymph node micrometastases in human breast cancer. J. Am. Coll. Surg., 206(2):261-268, 2008.

Crnogorac-Jurcevic et al. Proteomic analysis of chronic pancreatitis and pancreatic adenocarcinoma. Gastroenterology, 129:1454-1463, 2005.

Croci et al. Inhibition of connective tissue growth factor (CTGF/CCN2) expression decreases the survival and myogenic differentiation of human rhabdomyosarcoma cells. Cancer Res., 64(5):1730-1736, 2004.

Crooke. Progress in antisense technology. Annu. Rev. Med., 55:61-95, 2004.

Cross et al. 25-Hydroxyvitamin D (3)-1alpha-hydroxylase and vitamin D receptor gene expression in human colonic mucosa is elevated during early cancerogenesis. Steroids, 66:287-292, 2001.

Cully et al. Transforming acidic coiled coil 1 promotes transformation and mammary tumorigenesis. Cancer Res., 65(22):10363-10370, 2005.

Cummins and Velculescu. Implications of micro-RNA profiling for cancer diagnosis. Oncogene, 25(46):6220-6227, 2006.

Cummins et al. The colorectal microRNAome. Proc. Natl. Acad. Sci. USA, 103(10):3687-3692, 2006.

Dahl et al. Identification of sentinel nodes in patients with colon cancer. Eur. J. Surg. Oncol., 31(4):381-385, 2005.

Dai et al., Prostate cancer induces bone metastasis through Wnt-induced bone morphogenetic protein-dependent and independent mechanisms. Cancer Res., 68(14):5785-94, 2008.

Danilkovitch-Miagkova and Zbar. Dysregulation of Met receptor tyrosine kinase activity in invasive tumors. J Clin Invest, 109(7):863-867, 2002.

D'Antonio et al. Transforming growth factor alpha, amphiregulin and cripto-1 are frequently expressed in advanced human ovarian carcinomas. Int. J Oncol. 21(5):941-948, 2002.

(56) References Cited

OTHER PUBLICATIONS

Database EMBL. Human DNA related to regulating mammalian cells using miRNAs Seq 471. EBI Database Accession No. ADR83569, Dec. 2, 2004.
Davalos et al. High EPHB2 mutation rate in gastric but not endometrial tumors with microsatellite instability. Oncogene, 26 (2):308-311, 2006.
David P. Bartel. MicroRNAs: Genomics, Biogenesis, Mechanism, and Function, Cell, vol. 116, pp. 281-297 (Jan. 23, 2004).
Davis et al. Modeling of repeated-batch transcription for production of RNA. Journal of Biotechnology, 71:25-37, 1999.
Davison et al. Analyzing micro-RNA expression using microarrays. Meth. Enzymol. 411:14-34, 2006.
D'Cunha et al. Poor correspondence between clinical and pathologic staging in stage 1 nonsmall cell lung cancer: results from CALGB 9761, a prospective trial. Lung Cancer, 48:241-246, 2005.
De Boer et al. Micrometastases and isolated tumor cells: relevant and robust or rubbish? (MIRROR): preliminary results of the MIRROR study from the Dutch breast cancer trialists' group (BOOG). San Antonio Breast Cancer Symposium, Abstract 23, 2008.
De Candia et al. Id4 messenger RNA and estrogen receptor expression: inverse correlation in human normal breast epithelium and carcinoma. Hum. Pathol. 37 (8):1032-1041, 2006.
De Nigris et al. Induction of ETS-1 and ETS-2 transcription factors is required for thyroid cell transformation. Cancer Res., 61 (5):2267-2275, 2001.
Dean et al. The human met oncogene is related to the tyrosine kinase oncogenes. Nature, 318(6044):385-388, 1985.
Decision on Appeal, Appeal 2008-002253, issued in U.S. Appl. No. 10/880,350, decided May 29, 2009.
Declaration of Dr. David P. Bartel under 37 C.F.R. 1.132, submitted in U.S. Appl. No. 10/913,288, 2009.
Denli and Hannon. RNAi: an ever-growing puzzle. Trends Biochem. Sci., 28:196, 2003.
Devine et al. Serum markers CASA, CEA, CYFRA, TPS, and NSE in lung cancer. Lung Cancer, Abstract, 11:37, 1994.
Dews et al. Augmentation of tumor angiogenesis by a Myc-activated microRNA cluster. Nat. Genet., 38(9):1060-1065, 2006.
Diederichs and Haber. Sequence variations of microRNAs in human cancer: Alterations in predicted secondary structure do not affect processing. Cancer Res., 66(12):6097-6104, 2006.
Dillon et al. An APRIL to remember: novel TNF ligands as therapeutic targets. Nat Rev Drug Discov, 5(3):235-246, 2006.
DiSepio et al. Identification and characterization of a retinoid-induced class II tumor suppressor/growth regulatory gene. Proc. Natl. Acad. Sci. USA, 95:14811-14815, 1998.
Dittmer. The biology of the Ets1 proto-oncogene. Mol Cancer, 2:29, 2003.
Doench and Sharp. Specificity of microRNA target selection in translational repression. Genes Dev, 18(5):504-11, 2004.
Dong et al. Telomerase: regulation, function and transformation. Crit Rev Oncol Hematol. 54(2):85-93, 2005.
Donnellan and Chetty. Cyclin D1 and human neoplasia. Mol Pathol. 51(1):1-7, 1998.
Dontu et al. In vitro propagation and transcriptional profiling of human mammary stem/progenitor cells. Genes Dev., 17:1253-70, 2003.
Dostie et al. Numerous microRNPs in neuronal cells containing novel microRNAs. RNA, 9:180-186; 2003.
D'Souza et al. Case-control study of human papillomavirus and oropharyngeal cancer. New Engl. J. Med., 356:1944-1956, 2007.
Doyle and Ross. Multidrug resistance mediated by the breast cancer resistance protein BCRP (ABCG2). Oncogene, 22(47):7340-58, 2003.
Droge and Davey. Do cells let-7 determine sternness? Cell Stem Cell, 2(1):8-9, 2008.
Duvic et al. Expression of a retinoid-inducible tumor suppressor, tazarotene-inducible gene-3 is decreased in psoriasis and skin cancer. Clin. Cancer Res., 6 (8):3249-3259, 2000.
Duvic et al. Tazarotene-induced gene 3 is suppressed in basal cell carcinomas and reversed in vivo by tazarotene application. J. Invest. Dermatol. 121:902-909, 2003.
Dyer and Bremner. The search for the retinoblastoma cell of origin. Nat Rev Cancer, 5(2):91-101, 2005.
Dylla et al. Colorectal cancer stem cells are enriched in xenogeneic tumors following chemotherapy. PLoS One, 3(6):e2428, 13 pages, 2008.
Ebert et al. Induction and expression of amphiregulin in human pancreatic cancer. Cancer Res., 54(15):3959-3962, 1994.
Eferl et al. Liver tumor development. c-Jun antagonizes the proapoptotic activity of p53. Cell, 112 (2):181-192, 2003.
Egle et al. Bim is a suppressor of Myc-induced mouse B cell leukemia. Proc Natl Aced Sci USA. 101(16):6164-6169, 2004.
Egloff et al. Cyclin B1 and other cyclins as tumor antigens in immunosurveillance and immunotherapy of cancer. Cancer Res, 66(1):6-9, 2006.
Einama et al. High-level Skp2 expression in pancreatic ductal adenocarcinoma: correlation with the extent of lymph node metastasis, higher histological grade, and poorer patient outcome. Pancreas, 32(4):376-381, 2006.
Engelmann et al. MCF7 side population cells with characteristics of cancer stem/progenitor cells express the tumor antigen MUC1. Cancer Res., 68(7):2419-26, 2008.
Esau et al. MicroRNA-143 regulates adipocyte differentiation. Journal of Biological Chemistry, 279(50):52361-52365, 2004.
Esquela-Kerscher and Slack. Oncomirs—microRNAs with a role in cancer. Nat Rev Cancer, 6(4):259-269, 2006.
Esquela-Kerscher et al. The let-7 microRNA reduces tumor growth in mouse models of lung cancer. Cell Cycle, 7(6):759-764, 2008.
Esser et al. The role of sentinel lymph node mapping in staging of colon and rectal cancer. Dis Colon Rectum, 44(6):850-856, 2001.
European Office Action for Application No. 07814937, issued Apr. 8, 2011.
European Office Action for Application No. 09154092, issued Mar. 30, 2011.
European Search Report and Search Opinion issued in European Application No. 09154092.2, mailed Aug. 12, 2009.
European Search Report for Application No. 10183560.1 issued Jan. 7, 2011.
European Search Report for Application No. 10183567.6 issued Jan. 7, 2011.
European Search Report for Application No. 10183577.5, issued Feb. 14, 2011.
Extended European Search Report issued in European Application No. 10181713.8, mailed Jun. 24, 2011.
Extended European Search Report issued in European Application No. 10181728.6, mailed Jul. 8, 2011.
Extended European Search Report issued in European Application No. 10181821.9, mailed Jul. 29, 2011.
Extended European Search Report issued in European Application No. 10183451.3, mailed Jan. 12, 2011.
Extended European Search Report issued in European Application No. 10183456.2, mailed Jan. 12, 2011.
Extended European Search Report issued in European Application No. 10183462.0, mailed Feb. 4, 2011.
Extended European Search Report issued in European Application No. 10183470.3, mailed Feb. 3, 2011.
Extended European Search Report issued in European Application No. 10183481.0, mailed Jan. 7, 2011.
Extended European Search Report issued in European Application No. 10183490.1, mailed Feb. 4, 2011.
Extended European Search Report issued in European Application No. 10183515.5, mailed Feb. 7, 2011.
Extended European Search Report issued in European Application No. 10183525.4, mailed Feb. 7, 2011.
Extended European Search Report issued in European Application No. 10183534.5, mailed Feb. 15, 2011.
Extended European Search Report issued in European Application No. 10183538.7, mailed Jan. 12, 2011.
Extended European Search Report issued in European Application No. 10183543.7, mailed Feb. 4, 2011.

(56) References Cited

OTHER PUBLICATIONS

Extended European Search Report issued in European Application No. 10183589.0, mailed Jan. 7, 2011.
Extended European Search Report issued in European Application No. 10183596.5, mailed Feb. 14, 2011.
Extended European Search Report issued in European Application No. 10183611.2, mailed Jan. 7, 2011.
Extended European Search Report issued in European Application No. 10183639.3, mailed Mar. 2, 2011.
Ezzat et al. Dual inhibition of RET and FGFR4 restrains medullary thyroid cancer cell growth. Clin. Cancer Res., 11 (3):1336-1341, 2005.
Fakharzadeh et al. Tumorigenic potential associated with enhanced expression of a gene that is amplified in a mouse tumor cell line. Embo J, 10(6):1565-1569, 1991.
Fan et al. Hedgehog signaling promotes prostate xenograft tumor growth. Endocrinology, 145:3961-3970, 2004.
Fan et al. Notch pathway inhibition depletes stem-like cells and blocks engraftment in embryonal brain tumors. Cancer Res., 66(15):7445-52, 2006.
Faried et al. RhoA and RhoC proteins promote both cell proliferation and cell invasion of human oesophageal squamous cell carcinoma cell lines in vitro and in vivo. Eur. J. Cancer, 42 (10):1455-1465, 2006.
Fay et al. Analysis of CUL-5 expression in breast epithelial cells, breast cancer cell lines, normal tissues and tumor tissues. Mol. Cancer, 2:40, 2003.
Fazi et al. A minicircuitry comprised of microRNA-223 and transcription factors NFI-A and C/EBPa regulates human granulopoiesis. Cell, 123:819-831, 2005.
Feldman and Feldman. The development of androgen-independent prostate cancer. Nat. Rev. Cancer, 1(1):34-45, 2001.
Fernandez et al. The matrix metalloproteinase-9/neutrophil gelatinase-associated lipocalin complex plays a role in breast tumor growth and is present in the urine of breast cancer patients. Clin. Cancer Res., 11(15):5390-5395, 2005.
Ferris et al. Molecular staging of cervical lymph nodes in squamous cell carcinoma of the head and neck. Cancer Res., 65:2147-2156, 2005.
Fesik. Promoting apoptosis as a strategy for cancer drug discovery. Nat Rev Cancer, 5(11):876-885, 2005.
Firth and Baxter. Cellular actions of the insulin-like growth factor binding proteins. Endocrin. Rev., 23 (6):824-854, 2002.
Folkman. Successful treatment of an angiogenic disease. N Engl J Med 320:1211-1212, 1989.
Fontana et al. MicroRNA's 17-5p-20a-106a control monocytopeiesis through AML1 targeting and M-CSF receptor upregulation. Nature Cell Biology, 9(7):775-787, 2007.
Francipane et al. Crucial role of interleukin-4 in the survival of colon cancer stem cells. Cancer Res., 68 (11):4022-4025, 2008.
Freelove and Walling. Pancreatic cancer: diagnosis and management. Am. Fam. Physician, 73(3):485-492, 2006.
Fujiwara et al. Isolation of a candidate tumor suppressor gene on chromosome 8p21.3-p22 that is homologous to an extracellular domain of the PDGF receptor beta gene. Oncogene, 10(5):891-895, 1995.
Galardi et al. miR-221 and miR-222 expression affects the proliferation potential of human prostate carcinoma cell lines by targeting p27Kip1. J Biol. Chem, 282(32):23716-23724, 2007.
Gao et al. Frequent loss of PDCD4 expression in human glioma: possible role in the tumorigenesis of glioma. Oncol. Rep., 17(1):123-128, 2007.
Garzon et al. MicroRNA fingerprints during human megakaryocytopoiesis. Proc. Natl. Acad. Sci. USA, 103(13):5078-5083, 2006.
Garzon et al. MicroRNA signatures associated with cytogenetics and outcome in acute myeloid leukemia. Session Type: Oral Session. Blood, 108(11):49A, Abstract #151, 2006.
Gerald and Haber. The EWS-WT1 gene fusion in desmoplastic small round cell tumor. Semin Cancer Biol, 15(3):197-205, 2005.
Giannakakis et al. miRNA genetic alterations in human cacners. Expert opinion on biological therapy, 7(9):1375-1386, 2007.
Gillanders et al. Molecular detection of micrometastatic breast cancer in histopathology-negative axillary lymph nodes correlates with traditional predictors of prognosis: an interim analysis of a prospective multi-institutional cohort study. Ann. Surg., 239:828-840, 2004.
Gilles et al. Vimentin expression in cervical carcinomas: association with invasive and migratory potential. J Pathol, 180(2):175-180, 1996.
Ginestier et al. ALDH1 is a marker of normal and malignant human mammary stem cells and a predictor of poor clinical outcome. Cell Stem Cell, 1(5):555-567, 2007.
Gipponi et al. Sentinel lymph node as a new marker for therapeutic planning in breast cancer patients. J. Surg. Oncol., 85(3):102-111, 2004.
Goke et al. Programmed cell death protein 4 suppresses CDK1/cdc2 via induction of p21(WaH/Cip1). Am. J Physiol. Cell Physiol., 287(6):C1541-6, 2004.
Gomez-Bougie et al. The imbalance between Bim and Mc1-1 expression controls the survival of human myeloma cells. Eur J Immunol, 34(11):3156-3164, 2004.
Gonzalez et al. Oncogenic activity of Cdc6 through repression of the INK4/ARF locus. Nature, 440(7084):702-706, 2006.
Goodell et al. Isolation and functional properties of murine hematopoietic stem cells that are replicating in vivo. J. Exp. Med., 183(4):1797-806, 1996.
Goyns et al. The c-ets-1 proto-oncogene is rearranged in some cases of acute lymphoblastic leukaemia. Br J Cancer, 56(5):611-613, 1987.
Grandori et al. The Myc/Max/Mad network and the transcriptional control of cell behavior. Annu. Rev. Cell. Dev. Biol., 16:653-699, 2000.
Grenier et al. Cyfra 21-1, a new marker for lung cancer. Nucl. Med. Biol., 21(3):471-476, 1994.
Griffiths-Jones et al. miRBase: microRNA sequences, targets and gene nomenclature. Nucleic Acids Res., 34 (Database Issue):D140-D144, 2006.
Griffiths-Jones et al. miRBase: tools for microRNA genomics. Nucl. Acids Res., 36 (Database Issue):D154-D158, 2008.
Grimwade. The clinical significance of cytogenetic abnormalities in acute myeloid leukaemia. Best. Pract. Res. Clin.Haematol., 14:497-529, 2001.
Grishok et al. Genes and mechanisms related to RNA interference regulate expression of the small temporal RNAs that control C. elegans developmental timing. Cell, 106:23-34, 2001.
Grosshans et al. The temporal patterning microRNA let-7 regulates several transcription factors at the larval to adult transition in C. elegans. Dev. Cell, 8(3):321-330, 2005.
Gstaiger et al. Skp2 is oncogenic and overexpressed in human cancers. Proc. Natl. Acad. Sci. USA, 98(9):5043-5048, 2001.
Gu et al. Prostate cancer cells with stem cell characteristics reconstitute the original human tumor in vivo. Cancer Res., 67(10):4807-15, 2007.
Guda and Subramaniam. TARGET: a new method for predicting protein subcellular localization in eukaryotes. Bioinformatics, 21: 3963-3969, 2005.
Guo et al. Reduced expression of EphB2 that parallels invasion and metastasis in colorectal tumours. Carcinogenesis, 27(3):454-464, 2006.
Gurevich. Preparative in vitro mRNA synthesis using SP6 and T7 RNA polymerases. Anal Biochem. 195(2):207-213, 1991.
Ha et al. A bulged lin-4/lin-14 RNA duplex is sufficient for Caenorhabditis elegans lin-14 temporal gradient formation. Genes Dev., 10, 3041-3050, 1996.
Hajnal et al. Subtaction cloning of H-rev107, a gene specifically expressed in H-ras resistant fibroblasts. Oncogene, 9:479-490, 1994.
Hamamura et al. Ganglioside GD3 promotes cell growth and invasion through p130Cas and paxillin in malignant melanoma cells. Proc Natl Acad Sci US A, 102(31):11041-11046, 2005.
Hambardzumyan et al. Pl3K pathway regulates survival of cancer stem cells residing in the perivascular niche following radiation in medulloblastoma in vivo. Genes Dev., 22(4):436-48, 2008.
Han et al. Cyclin D I expression in human prostate carcinoma cell lines and primary tumors. The Prostate, 35:95-101, 1998.

(56) References Cited

OTHER PUBLICATIONS

Hanahan and Weinberg. The hallmarks of cancer. Cell, 100(1):57-70, 2000.
Hannigan et al. Integrin-linked kinase: a cancer therapeutic target unique among its ILK. Nat Rev Cancer, 5(1):51-63, 2005.
Hardenbol et al. Multiplexed genotyping with sequence-tagged molecular inversion probes. Nat Biotechnol, 21(6):673-678, 2003.
Harle. MicroRNAs in vertebrate development. Curr. Opin. Genet. Dev., 15(4):410-5, 2005.
Hartmann et al. Hypoxia-induced up-regulation of angiogenin in human malignant melanoma. Cancer Res., 59 (7):1578-1583, 1999.
Hayashita et al. A polycistronic microRNA cluster, miR-17-92, is overexpressed in human lung cancers and enhances cell proliferation. Cancer Res., 65(21):9628-9632, 2005.
Hayette et al. In B-cell chronic lymphocytic leukemias, 7q21 translocations lead to overexpression of the CDK6 gene. Blood, 102(4):1549-1550, 2003.
He et al. A microRNA component of the p53 tumour suppressor network. Nature, 447(7148):1130-1134, 2007.
He et al. A microRNA polycistron as a potential human oncogene. Nature, 435(7043):828-833, 2005.
He et al. The role of microRNA genes in papillary thyroid carcinoma. Proc. Natl. Acad. Sci. USA, 102(52):19075-19080, 2005.
Hermann et al. Distinct populations of cancer stem cells determine tumor growth and metastatic activity in human pancreatic cancer. Cell Stem Cell, 1(3):313-23, 2007.
Hermeking. p53 enters the microRNA world. Cancer Cell, 12(5):414-418, 2007.
Hirschmann-Jax et al. A distinct side population of cells with high drug efflux capacity in human tumor cells. Proc. Natl. Acad. Sci. USA, 101:14228-33, 2004.
Hishikawa et al. Connective tissue growth factor induces apoptosis in human breast cancer cell line MCF-7. J. Biol. Chem., 274(52):37461-37466, 1999.
Ho et al. MDR1 and BCRP1 expression in leukemic progenitors correlates with chemotherapy response in acute myeloid leukemia. Exp. Hematol., 36(4):433-42, 2008.
Ho et al. Quantification of colorectal cancer micrometastases in lymph nodes by nested and real-time reverse transcriptase-PCR analysis for carcinoembryonic antigen. Clin. Cancer Res., 10(17):5777-5784, 2004.
Hodge et al. The role of IL-6 and STAT3 in inflammation and cancer. Eur J Cancer, 41(16):2502-2512, 2005.
Hoeflich et al. Insulin-like growth factor-binding protein 2 in tumorigenesis: protector or promoter? Cancer Res, 61(24):8601-8610, 2001.
Hofer et al. The role of metastasis-associated protein 1 in prostate cancer progression. Cancer Res, 64(3):825-829, 2004.
Holmquist-Mengelbier et al. Recruitment of HIF-1 alpha and HIF-2alpha to common target genes is differentially regulated in neuroblastoma: HIF-2alpha promotes an aggressive phenotype. Cancer Cell, 10(5):413-423, 2006.
Honma et al. The role of atelocollagen-based cell transfection array in high-throughput screening of gene functions and in drug discovery. Current Drug Discovery Technologies, 1(4):287-294, 2004.
Hornstein et al. The microRNA mir-196 acts upstream of Hoxb8 and Shh in limb development. Nature, 438:671-674, 2005.
Horoszewicz et al. The LNCaP cell line—a new model for studies on human prostatic carcinoma. Prog Clin Biol Res., 37:115-32, 1980.
Houbaviy et al. Embryonic stem cell-specific micro-RNAs. Developmental Cell, 5:351-358, 2003.
Houston and O'Connell. The Fas signalling pathway and its role in the pathogenesis of cancer. Carr Opin Pharmacol, 4(4):321-326, 2004.
Houvenaeghel et al. Micrometastases in sentinel lymph node in a multicentric study: predictive factors of nonsentinel lymph node involvement—Groupe des Chirurgiens de la Federation des Centres de Lutte Contre le Cancer. J. Clin. Oncol. 24:1814-1822, 2006.
Hsu et al. BOD (Bcl-2-related ovarian death gene) is an ovarian BH3 domain-containing proapoptotic Bcl-2 protein capable of dimerization with diverse antiapoptotic Bcl-2 members. Mol Endocrinol, 12(9):1432-1440, 1998.
Huang et al. Cloning and characterization of a novel retinoid-inducible gene 1 (RIG1) deriving from human gastric cancer cells. Mol. Cell. Endocrinol. 159:15-24, 2000.
Huang et al. Skp2 inhibits FOX01 in tumor suppression through ubiquitin-mediated degradation. Proc. Natl. Acad. Sci. USA, 102(5):1649-1654, 2005.
Huang et al. Skp2 overexpression is highly representative of intrinsic biological aggressiveness and independently associated with poor prognosis in primary localized myxofibrosarcomas. Clin. Cancer Res., 12 (2):487-498, 2006.
Huang et al. The retinoid-inducible gene I: effect on apoptosis and mitogen-activated kinase signal pathways. Anticancer Res., 22:799-804, 2002.
Huang et al. Wnt5a expression is associated with the tumor proliferation and the stromal vascular endothelial growth factor—an expression in non-small-cell lung cancer. J. Clin. Oncol., 23 (34):8765-8773, 2005.
Huber et al. Variance stabilization applied to microarray data calibration and to the quantification of differential expression. Bioinformatics, 18:Suppl 1:S96-104, 2002.
Hughes et al. A rapid, fully automated, molecular-based assay accurately analyzes sentinel lymph nodes for the presence of metastatic breast cancer. Ann. Surg., 243:389-398, 2006.
Human miRNA targets. For mmu-miR-126-3p Apr. 2005 version, accessed and retrieved from miRanda webserver at www.microrna.org and http://cbio.mskcc.org/cgi-bin/mirnaviewer, on Dec. 31, 2009. p. 1 of the 23 print-out pages included.
Hummel et al. Differentiation-induced and constitutive transcription of human papillomavirus type 3 lb in cell lines containing viral episomes. J Virol. 66(10):6070-80, 1992.
Hurt et al. CD44+ CD24(−) prostate cells are early cancer progenitor/stem cells that provide a model for patients with poor prognosis. Br. J. Cancer, 98(4):756-65, 2008.
Hutvagner and Zamore. A microRNA in a multiple-turnover RNAi enzyme complex. Science, 297(5589):2056-2060, 2002.
Hutvagner et al. Sequence-specific inhibition of small RNA function. PLoS Biol. 2(4):E98, 2004.
Huusko et al. Nonsense-mediated decay microarray analysis identifies mutations of EPHB2 in human prostate cancer. Nat. Genet., 36 (9):979-983, 2004.
Hynes and Lane. ERBB receptors and cancer: the complexity of targeted inhibitors. Nat Rev Cancer, 5(5):341-354, 2005.
Ibarra et al. A role for microRNAs in maintenance of mouse mammary epithelial progenitor cells, Genes Dev., 21(24):3238-3243, 2007.
Illmer et al. MiRNA expression signatures in actue myeloid leukemia are predictors for patient outcome. Session Type: Oral Session. Blood, 108(11):49A, Abstract #152, 2006.
International Preliminary Report on Patentability and Written Opinion, issued in; International Application No. PCT/US2005/022710, mailed Jan. 18, 2007.
International Preliminary Report on Patentability and Written Opinion, issued in; International Application No. PCT/US2005/041162, mailed Dec. 6, 2007.
International Search Report and Written Opinion, issued in International Application No. PCT/US2005/022710, mailed Oct. 7, 2005.
Iorio et al. MicroRNA gene expression deregulation in human breast cancer. Cancer Res, 65(16):7065-7070, 2005.
Isbarn et al. Association of numerous micro-RNAs (i.tRNAs) with prostate cancer initiation and progression. European Urology Supplements, Abstract No. 429, 6(2):130, 2007.
Ishikawa et al. Increases of amphiregulin and transforming growth factor-alpha in serum as predictors of poor response to gefitinib among patients with advanced non-small cell lung cancers. Cancer Res., 65(20):9176-9184, 2005.
Islam et al. Vimentin expression in human squamous carcinoma cells: relationship with phenotypic changes and cadherin-based cell adhesion. J Cell Biochem, 78(1):141-150, 2000.

(56) References Cited

OTHER PUBLICATIONS

Ito et al. Decreased expression of cyclin G2 is significantly linked to the malignant transformation of papillary carcinoma of the thyroid. Anticancer Res., 23(3B):2335-2338, 2003.
Ito et al. Decreased expression of p107 is correlated with anaplastic transformation in papillary carcinoma of the thyroid. Anticancer Res., 23(5A):3819-3824, 2003.
Ito et al. Expression of ets-1 and ets-2 in colonic neoplasms. Anticancer Res., 22 (3):1581-1584, 2002.
Ito et al. Expression of p8 protein in medullary thyroid carcinoma. Anticancer Res., 25 (5):3419-3423, 2005.
Jaakkola et al. Amplification of fgfr4 gene in human breast and gynecological cancers. Int. J Cancer, 54 (3):378-382, 1993.
Jaattela. Over-expression of hsp70 confers tumorigenicity to mouse fibrosarcoma cells. Int. J Cancer, 60(5):689-693, 1995.
Jackson and Foster. The enigmatic protein kinase Cdelta: complex roles in cell proliferation and survival. Faseb J, 18(6):627-636, 2004.
Jamieson et al. Granulocyte-macrophage progenitors as candidate leukemic stem cells in blast-crisis CML. N Engl. J. Med., 351(7):657-67, 2004.
Jang et al. Gene delivery from polymer scaffolds for tissue engineering. Expert Rev. Medical Devices, 1(1):127-138, 2004.
Jang et al. MTA1 overexpression correlates significantly with tumor grade and angiogenesis in human breast cancers. Cancer Sci, 97(5):374-379, 2006.
Janknecht. EWS-ETS oncoproteins: the linchpins of Ewing tumors. Gene, 363:1-14, 2005.
Jansen et al. Characterization of programmed cell death 4 in multiple human cancers reveals a novel enhancer of drug sensitivity. Mol. Cancer Ther. 3(2):103-110, 2004.
Jansen et al. Epidermal expression of the translation inhibitor programmed cell death 4 suppresses tumorigenesis. Cancer Res., 65(14):6034-41, 2005.
Jansen et al. Two unrelated cell-derived sequences in the genome of avian leukemia and carcinoma inducing retrovirus MH2. Embo J, 2(11):1969-1975, 1983.
Japanese Office Action, issued May 29, 2013, in Japanese Application No. 2012-150997. (6 pages).
Jemal et al. Cancer statistics, 2007. CA Cancer J. Clin., 57:43-66, 2007.
Jemielity et al. Novel 'anti-reverse' cap analogs with superior translational properties. RNA, 9(9):1108-1122, 2003.
Ji et al. BMC Cancer 2008. vol. 8. p. 266-277.
Jiang et al. Decreased expression of type II tumor suppressor gene RARRES3 in tissues of hepatocellular carcinoma and cholangiocarcinoma. World J. Gastroenterol., 11:948-953, 2005.
Jiang et al. Real-time expression profiling of microRNA precursors in human cancer cell lines. Nucleic Acids Research, 33(17):5394-5403, 2005.
Jiang et al. RNA silencing of S-phase kinase-interacting protein 2 inhibits proliferation and centrosome amplification in lung cancer cells. Oncogene, 24(21):3409-3418, 2005.
Jin et al. Tumorigenic transformation by CPI-17 through inhibition of a merlin phosphatase. Nature, 442 (7102):576-579, 2006.
Jing et al. Tazarotene-induced gene 1 (TIG1) expression in prostate carcinomas and its relationship to tumorigenicity. J. Natl. Cancer Inst., 94:482-490, 2002.
John et al. Human microRNA targets. PLOS Biology, 2(11):1862-1879, 2004.
Johnson et al. RAS is regulated by the let-7 microRNA family. Cell, 120:635-647, 2005.
Johnson et al. The let-7 microRNA represses cell proliferation pathways in human cells. Cancer Res, 67(16):7713-7722, 2007.
Jonsson et al. Loss of Wnt-5a protein is associated with early relapse in invasive ductal breast carcinomas. Cancer Res., 62 (2):409-416, 2002.
Jopling et al. Modulation of hepatitis C virus RNA abundance by a liver-specific MicroRNA. Science, 309(5740):1577-81, 2005.
Jubb et al. EphB2 is a prognostic factor in colorectal cancer. Clin. Cancer Res., 11 (14):5181-5187, 2005.

Kabbarah et al. Expression Profiling of Mouse Endometrial Cancers Microdissected from Ethanol-Fixed, Paraffin-Embedded Tissues. Am. J. Pathology, 162:755-762, 2003.
Kalin et al. Increased levels of the FoxM1 transcription factor accelerate development and progression of prostate carcinomas in both TRAMP and LADY transgenic mice. Cancer Res, 66(3):1712-1720, 2006.
Kalinichenko et al. Foxm1b transcription factor is essential for development of hepatocellular carcinomas and is negatively regulated by the p19ARF tumor suppressor. Genes Dev, 18(7):830-850, 2004.
Kelley et al. Vitamin D receptor activity and prevention of colonic hyperproliferation and oxidative stress. Food Chem. Toxicol., 40:1191-1196, 2002.
Kamata et al. High expression of skp2 correlates with poor prognosis in endometrial endometrioid adenocarcinoma. J Cancer Res. Clin. Oncol. 131(9):591-596, 2005.
Kammula et al. Serial follow-up and the prognostic significance of reverse transcriptase-polymerase chain reaction—staged sentinel lymph nodes from melanoma patients. J Clin. Oncol., 22:3989-3996, 2004.
Kapsimali et al. MicroRNAs show a wide diversity of expression profiles in the developing and mature central nervous system. Genome Biol, 8(8):R173, 2007.
Karakaidos et al. Overexpression of the replication licensing regulators hCdtl and hCdc6 characterizes a subset of non-small-cell lung carcinomas: synergistic effect with mutant p53 on tumor growth and chromosomal instability—evidence of E2F-1 transcriptional control over hCdtl. Am J Pathol, 165(4):1351-1365, 2004.
Karginov et al. A biochemical approach to identifying microRNA targets. PNAS, 104(49):19291-19296, 2007.
Karhadkar et al. Hedgehog signalling in prostate regeneration, neoplasia and metastasis. Nature, 431(7009):707-12, 2004.
Karin et al. NF-kappaB in cancer: from innocent bystander to major culprit. Nat Rev Cancer, 2(4):301-310, 2002.
Kasashima et al. Altered expression profiles of microRNAs during TPA-induced differentiation of HL-60 cells. Biochemical and Biophysical Research Communications, 322(2):403-410, 2004.
Kastan and Lim. The many substrates and functions of ATM. Nat Rev Mol Cell Biol, 1(3):179-186, 2000.
Kato. Adaptor-tagged competitive PCR: a novel method for measuring relative gene expression. Nucleic Acids Research, Oxford University Press, Surrey, GB, 25(22):4694-4696, 1997.
Kaufmann et al. Elevated expression of the apoptotic regulator Mc1-1 at the time of leukemic relapse. Blood, 91(3):991-1000, 1998.
Kayed et al. Hedgehog signaling in the normal and diseased pancreas. Pancreas, 32(2):119-129, 2006.
Keen and Taylor. Aurora-kinase inhibitors as anticancer agents. Nat. Rev. Cancer, 4(12):927-936, 2004.
Kent et al. (Oncogene 25, 6188-6196, 2006).
Kern et al. Application of a fed-batch system to produce RNA by in vitro transcription. Biotechnol. Prog., 15:174-184, 1999.
Kern et al. Application of solution equilibrium analysis to in vitro RNA transcription. Biotechnol. Prog., 13:747-756, 1997.
Keshet et al. MDR1 expression identifies human melanoma stem cells. Biochem. Biophys. Res. Commun., 368(4):930-6, 2008.
Kim et al. Genomics of microRNA. Trends in Genetics, 22:165-173, 2006.
Kim et al. Identification of many microRNAs that copurify with polyribosomes in mammalian neurons. Proc. Natl. Acad. Sci., USA, 101:360-365, 2004.
Kiriakidou et al. A combined computational-experimental approach predicts human microRNA targets. Genes Dev. 18(10):1165-78, 2004.
Kiriakidou et al. An mRNA m7G cap binding-like motif within human Ago2 represses translation. Cell, 129(6):1141-1151, 2007.
Kirikoshi et al. Up-regulation of Frizzled-7 (FZD7) in human gastric cancer. Int. J. Oncol., 19 (1):111-115, 2001.
Kita et al. Modulation of polygulutamine-induced cell death by genes identified by expression profiling. Human Molecular Genetics, 11(19):2279-2287, 2002.
Kitadai et al. Expression of amphiregulin, a novel gene of the epidermal growth factor family, in human gastric carcinomas. Jpn. J. Cancer Res., 84(8):879-884, 1993.

(56) References Cited

OTHER PUBLICATIONS

Kleer et al. RhoC GTPase expression as a potential marker of lymph node metastasis in squamous cell carcinomas of the head and neck. Clin. Cancer Res., 12 (15):4485-4490, 2006.
Kohno and Pouyssegur. Pharmacological inhibitors of the ERK signaling pathway: application as anticancer drugs. Progress in Cell Cycle Research,. (Meijer, L., Jezequel, A., and Roberge, M., Eds), Chapter 22, vol. 5:219-224, 2003.
Koivunen et al. Protein kinase C alpha/beta inhibitor Go6976 promotes formation of cell junctions and inhibits invasion of urinary bladder carcinoma cells. Cancer Res, 64(16):5693-5701,2004.
Koivunen et al. Protein kinase C (PKC) family in cancer progression. Cancer Lett, 235(1):1-10, 2006.
Kokko et al. EPHB2 germline variants in patients with colorectal cancer or hyperplastic polyposis. BMC Cancer, 6:145, 2006.
Komatsu et al. Increased expression of S100A6 (Calcyclin), a calcium-binding protein of the S100 family, in human colorectal adenocarcinomas. Clin. Cancer Res., 6:172-177, 2000.
Komiya et al. PRLTS gene alterations in human prostate cancer. Jpn. J Cancer Res., 88(4):389-393, 1997.
Konopleva et al. Mechanisms of apoptosis sensitivity and resistance to the BH3 mimetic ABT-737 in acute myeloid leukemia. Cancer Cell, 10(5):375-88, 2006.
Kops et al. On the road to cancer: aneuploidy and the mitotic checkpoint. Nat Rev Cancer, 5(10):773-785. 2005.
Krek et al. Combinatorial microRNA target predictions. Nature Genet., 37:495-500, 2005.
Krichevsky et al. A microRNA array reveals extensive regulation of microRNAs during brain development. RNA, 9(10):1274-1281, 2003.
Kristjansdottir and Rudolph. Cdc25 phosphatases and cancer. Chem Biol,11(8):1043-1051, 2004.
Kubista et al. Light-up probe based real-time Q-PCR. Spit, 4264:53-58, 2001.
Kuehbacher et al. Targeting microRNA expression to regulate angiogenesis. Trends Pharmacol Sci., 29(1):12-15, 2008.
Kuhajda. Fatty acid synthase and cancer: new application of an old pathway. Cancer Res, 66(12):5977-5980, 2006.
Kumar et al. Suppression of non-small cell lung tumor development by the let-7 microRNA family. PNAS, 105(10):3903-3908, 2008.
Kwak et al. VEGF is major stimulator in model of choroidal neovascularization. Invest. Ophthalmol. Vis. Sci., 41(10):3158-3164, 2000.
Kwong et al. Silencing of the retinoid response gene TIG1 by promoter hypermethylation in nasopharyngeal carcinoma. Int. J Cancer, 113 (3): 386-392, 2005.
Labourier et al. Improving in vitro transcription for large scale sytnthesis of human quality capped RNA. Ambion Diagnostics, RNA Healthcare Solutions, Eukaryotic mRNA Processing meeting, Cold Spring Harbor Laboratory, Cold Spring Harbor, NY, Aug. 2003.
Lagos-Quintana et al. Idenfication of Tissue-Specific MicroRNAs from Mouse Curr Biol., Curr Science, vol. 12, No. 9, Apr. 2002; 735-739.
Lagos-Quintana et al. Identification of novel genes coding for small expressed RNAs. Science, 294(5543):853-858, 2001.
Lagos-Quintana et al. New microRNAs from mouse and human. RNA, 9(2):175-179, 2003.
Lam et al. Expression of pl9INK4d, CDK4, CDK6 in glioblastoma multiforme. Br J Neurosurg, 14(1):28-32, 2000.
Lanza et al. mRNA/microRNA gene expression profile in microsatellite unstable colorectal cancer. Molec Cancer, 6:54, 2007.
Lao et al. Multiplexing RT-PCR for the detection of multiple miRNA species in small samples. Biochemical and Biophysical Research Communications, 343:85-89, 2006.
Lau et al. An abundant class of tiny RNAs with probable regulatory roles in Caenorhabditis elegans. Science, 294(5543):858-862, 2001.
le Sage et al., Regulation of the p27(Kip1) tumor suppressor by miR-221 and miR-222 promotes cancer cell proliferation. EMBO J. Aug. 8, 2007;26(15):3699-708. Epub Jul. 12, 2007.
Lecellier et al. A cellular microRNA mediates antiviral defense in human cells. Science, 308(5721):557-60, 2005.
Lechner et al. Nestin-positive progenitor cells derived from adult human pancreatic islets of Langerhans contain side population (SP) cells defined by expression of the ABCG2 (BCRP1) ATP-binding cassette transporter. Biochem. Biophys. Res. Commun., 293(2):670-674, 2002.
Lee and Ambros. An extensive class of small RNAs in Caenorhabditis elegans. Science, 294(5543):862-864, 2001.
Lee et al. A protein reacted with anti-vitronectin antibody accumulates in tumors derived from B16F10 melanoma cells. Cell Struct. Funct., 23 (4):193-199, 1998.
Lee et al. Altered microRNA expression in cervical carcinomas. Clin Cancer Res, 14(9):2535-2542, 2008.
Lee et al. Ectopic expression of neutrophil gelatinase-associated lipocalin suppresses the invasion and liver metastasis of colon cancer cells. Int. J. Cancer, 118(10):2490-2497, 2006.
Lee et al. Expression profiling identifies stroma- and tumor-related microRNAs in pancreatic cancer. 97th Annual AACR, Washington D.C., Abstract No. 5725, 2006.
Lee et al. MicroRNA maturation: stepwise processing and subcellular localization. EMBO J., 21(17):4663-4670, 2002.
Lee et al. The C. elegans heterochronic gene lin-4 encodes small RNAs with antisense complementarity to lin-14. Cell, 75(5):843-854, 1993.
Lee et al. The nuclear RNase III Drosha initiates microRNA processing. Nature, 425(6956):415-419, 2003.
Leong and Gao. The Notch pathway in prostate development and cancer. Differentiation, 76(6):699-716, 2008.
Leprince et al. A putative second cell-derived oncogene of the avian leukaemia retrovirus E26. Nature, 306 (5941):395-397, 1983.
Leris et al. WNT5A expression in human breast cancer. Anticancer Res., 25 (2a):731-734, 2005.
Lessard and Sauvageau. Bmi-1 determines the proliferative capacity of normal and leukaemic stem cells. Nature, 423(6937):255-60, 2003.
Lewis et al. Conserved seed pairing, often flanked by adenosines, indicates that thousands of human genes are microRNA targets. Cell, 120:15-20, 2005.
Lewis et al. Prediction of mammalian microRNA targets. Cell, 115(7):787-798, 2003.
L'hote and Knowles. Cell responses to FGFR3 signalling: growth, differentiation and apoptosis. Exp. Cell. Res., 304 (2):417-431, 2005.
Li et al. Apoptosis of non-small-cell lung cancer cell lines after paclitaxel treatment involves the BH3-only proapoptotic protein Bim. Cell Death Differ, 12(3):292-303, 2005.
Li et al. Evidence that transgenes encoding components of the Wnt signaling pathway preferentially induce mammary cancers from progenitor cells. Proc Natl Aced Sci USA, 100(26):15853-8, 2003.
Li et al. Intrinsic resistance of tumorigenic breast cancer cells to chemotherapy. J Natl. Cancer Inst., 100(9):672-9, 2008.
Li et al. Mutant TNFalpha negatively regulates human breast cancer stem cells from MCF7 in vitro. Cancer Biol. Ther., 6(9):1480-9, 2007.
Li et al. Overexpression of ETS2 in human esophageal squamous cell carcinoma. World J. Gastroenterol., 9 (2):205-208, 2003.
Li et al. PDGF-D is a potent transforming and angiogenic growth factor. Oncogene, 22(10):1501-1510, 2003.
Liang et al. Chacterization of microRNA expression profiles in normal human tissues. BMC Genomics, 8:166, 2007.
Lilja et al. Prostate-specific antigen and prostate cancer: prediction, detection and monitoring. Nat. Rev. Cancer, 8(4):268-278, 2008.
Lim et al. Microarray analysis shows that some microRNAs downregulate large numbers of target mRNAs. Nature, 433(7027):769-773, 2005.
Lim et al. The microRNAs of Caenorhabditis elegans. Genes and Development, 17:991-1008, 2003.
Lima e Silva et al. The SDF-1/CXCR4 ligand/receptor pair is an important contributor to several types of ocular neovascularization. FASEB J., 21(12):3219-3230, 2007.
Lin and Gelman. Reexpression of the major protein kinase C substrate, SSeCKS, suppresses v-src-induced morphological transformation and tumorigenesis. Cancer Res, 57(11):2304-2312, 1997.

(56) References Cited

OTHER PUBLICATIONS

Lin et al. Connective tissue growth factor inhibits metastasis and acts as an independent prognostic marker in colorectal cancer. Gastroenterology, 128(1):9-23, 2005.
Lin et al. The C. elegans hunchback homolog, hbl-1, controls temporal patterning and is a probable microRNA target. Dev. Cell, 4(5):639-650, 2003.
Linsley et al. Transcripts targeted by the microRNA-16 family cooperatively regulate cell cycle progression. Molecular and Cellular Biology, 27(6):2240-2252, 2007.
Liu and Erikson. Polo-like kinase (P1101 depletion induces apoptosis in cancer cells. Proc Natl Acad Sci USA. 100(10):5789-5794, 2003.
Liu and Matsuura. Inhibition of Smad antiproliferative function by CDK phosphorylation. Cell Cycle, 4(1):63-66, 2005.
Liu et al. An oligonucleotide microchip for genome-wide micronRNA profiling in human and mouse tissue. Proc. Nat. Acad. Sci. USA, 101:9740-9744, 2004.
Liu et al. CpG island methylation and expression of the secreted frizzled-related protein gene family in chronic lymphocytic leukemia. Cancer Res., 66 (2):653-658, 2006.
Liu et al. Sex-determining region Y box 4 is a transforming oncogene in human prostate cancer cells. Cancer Res., 66(8):4011-9, 2006.
Liu et al. FoxMlB is overexpressed in human glioblastomas and critically regulates the tumorigenicity of glioma cells. Cancer Res., 66 (7):3593-3602, 2006.
Liu et al. Functional studies of BCL11A: characterization of the conserved BCL11A-XL splice variant and its interaction with BCL6 in nuclear paraspeckles of germinal center B cells. Mol. Cancer, 5:18, 2006.
Liu et al. Hedgehog signaling and Bmi-1 regulate self-renewal of normal and malignant human mammary stem cells. Cancer Res., 66(12):6063-71, 2006.
Liu et al. The prognostic role of a gene signature from tumorigenic breast-cancer cells. N Engl. J. Med., 356(3):217-26, 2007.
Lo et al. High resolution allelotype of microdissected primary nasopharyngeal carcinoma. Cancer Res., 60:3348-3353, 2000.
Lo Vasco et al. Inositide-specific phospholipase c betal gene deletion in the progression of myelodysplastic syndrome to acute myeloid leukemia. Leukemia, 18 (6):1122-1126, 2004.
Logsdon et al. Molecular profiling of pancreatic adenocarcinoma and chronic pancreatitis identifies multiple genes differentially regulated in pancreatic cancer. Cancer Research, 63:2649-2657, 2003.
Lu et al. Defined culture conditions of human embryonic stem cells, Proc. Natl. Acad. Sci. USA, 103(15):5688-93, 2006.
Lu et al. MicroRNA expression profiles classify human cancers. Nature, 435(7043):834-838, 2005.
Lucke et al. Inhibiting mutations in the transforming growth factor beta type 2 receptor in recurrent human breast cancer. Cancer Res, 61(2):482-485, 2001.
Lui et al. Patterns of known and novel small RNAs in human cervical cancer. Cancer Res., 67(13):6031-6043, 2007.
Lujambio et al. Genetic unmasking of an epigenetically silenced microRNA in human cancer cells. Cancer Research, 67(4):1424-1429, 2007.
Lukiw. Micro-RNA speciation in fetal, adult and Alzheimer's disease hippocampus. Neuroreport, 18(3):297-300, 2007.
Ma et al. Tumour invasion and metastasis initiated by microRNA-10b in breast cancer. Nature, 449(7163):682-688, 2007.
Mahato et al. Modulation of gene expression by antisense and antigene oligodeoxynucleotides and small interfering RNA. Expert Opinion on Drug Delivery, 2(1):3-28, 2005.
Maitland & Collins. Prostate cancer stem cells: a new target for therapy, J Clin Oncol., 26(17):2862-70, 2008.
Makeyev et al. The microRNA miR-124 promotes neuronal differentiation by triggering brain-specific alternative pre-mRNA splicing. Molecular Cell, 27(3):435-448, 2007.
Maki et al. Avian sarcoma virus 17 carries the jun oncogene. Proc. Natl. Acad. Sci. USA, 84 (9):2848-2852, 1987.
Malanchi et al. Cutaneous cancer stem cell maintenance is dependent on beta-catenin signalling. Nature, 452(7187):650-3, 2008.
Malumbres and Barbacid. To cycle or not to cycle: a critical decision in cancer. Nat Rev Cancer, 1(3):222-231, 2001.
Mammalian Gene Collection (MGC) Program Team. Generation and initial analysis of more than 15,000 full-length human and mouse cDNA sequences. PNAS, 99(26):16899-16903, 2002.
Manion and Hockenbery. Targeting Bc1-2-related proteins in cancer therapy. Cancer Biol Ther, 2(4 Suppl 1):5105-114, 2003.
Mansfield et al. MicroRNA-responsive 'sensor' transgenes uncover Hox-like and other developmentally regulated patterns of vertebrate microRNA expression. Nature Genetics, 36(10):1079-1083, 2004.
Marcucci et al. Prognostic factors and outcome of core binding factor acute myeloid leukemia patients with t(8;21) differ from those of patients with inv(16): a Cancer and Leukemia Group B study, 1Clin. Oncol., 23:5705-5717, 2005.
Markowitz et al. Inactivation of the type II TGF-beta receptor in colon cancer cells with microsatellite instability. Science, 268(5215):1336-1338, 1995.
Markowitz. TGF-beta receptors and DNA repair genes, coupled targets in a pathway of human colon carcinogenesis. Biochim. Biophys. Acta. 1470 (1):M13-20, 2000.
Marks. Thioredoxin in cancer—role of histone deacetylase inhibitors. Semin. Cancer Biol., 16(6):436-443, 2006.
Marone et al. Analysis of cyclin E and CDK2 in ovarian cancer: gene amplification and RNA overexpression. Int J Cancer, 75(1):34-39, 1998.
Martello et al. MicroRNA control of nodal signaling. Nature, 449(7159):183-188, 2007.
Martin and Keller. Tailing and 3'-end labeling of RNA with yeast poly(A) polymerase and various nucleotides. RNA, 4(2):226-230, 1998.
Martin et al. Molecular profiling of cervical neoplasia. Expert Review of Molecular Diagnostics, 6(2):217-229, 2006.
Martinez et al. Human papilloma virus type 16 reduces the expression of microRNA-218 in cervical carcinoma cells. Oncogene, 27:2575-2582, 2008.
Martinez. Identification of differentially expressed genes in HPV associated cancers using gene expression, tissue, and microRNA microarrays. Dissertation Abstract, University of Pittsburg, 2007.
Massague et al. TGFbeta signaling in growth control, cancer, and heritable disorders. Cell, 103 (2):295-309, 2000.
Matoba et al. Gene expression in mouse cerebellum during its development. Gene, 241:125-131, 2000.
Matoba et al. Gene expression profiling of mouse postnatal cerebellar development. Physiol.Genomics, 4:155-164, 2000.
Mattie et al. Optimized high-throughput microRNA expression profiling provides novel biomarker assessment of clinical prostate and breast cancer biopsies. Mol. Cancer, 5:24, 2006.
McInroy and Maatta. Down-regulation of vimentin expression inhibits carcinoma cell migration and adhesion. Biochem Biophys Res Commun, 360(1):109-114, 2007.
McManus. MicroRNAs and cancer. Seminars in Cancer Biology, 13:253-258, 2003.
Meister et al. Sequence-specific inhibition of microRNA- and siRNA-induced RNA silencing. RNA, 10(3):544-50, 2004.
Mendrzyk et al. Genomic and protein expression profiling identifies CDK6 as novel independent prognostic marker in medulloblastoma. J Clin Oncol, 23(34):8853-8862, 2005.
Meng et al. Involvement of human micro-ma in growth and response to chemotherapy in human cholangiocarcinoma cell lines. Gastroenterology, 130(7):2113-2129, 2006.
Merle et al. Functional consequences of frizzled-7 receptor overexpression in human hepatocellular carcinoma. Gastroenterology, 127 (4):110-1122, 2004.
Metzler et al. High Expression of Precursor MicroRNA-155/B/C RNA in Children with Burkitt Lymphoma. Genes, Chromosomes, & Cancer 39:167-169; 2004.
Mi et al. MicroRNA expression signatures accurately discriminate acute lymphoblastic leukemia from acute myeloid leukemia. PNAS, 104(50):19971-19976, 2007.
Michael and Oren. The p53-Mdm2 module and the ubiquitin system. Semin. Cancer Biol. 13:49-58, 2003.

(56) References Cited

OTHER PUBLICATIONS

Michael et al. Reduced accumulation of specific microRNAs in colorectal neoplasia. Mol. Cancer Res., 1:882-891, 2003.
Miki & Rhim. Prostate cell cultures as in vitro models for the study of normal stem cells and cancer stem cells, Prost. Can. Prost. Dis., 11:32-39, 2008.
Miki et al. Identification of putative stem cell markers, CD133 and CXCR4, in hTERT-immortalized primary nonmalignant and malignant tumor-derived human prostate epithelial cell lines and in prostate cancer specimens. Cancer Res., 67(7):3153-3161, 2007.
Miller et al. Vascular endothelial growth factor/vascular permeability factor is temporally and spatially correlated with ocular angiogenesis in a primate mode. Am. J. Pathol., 145(3):574-584, 1994.
Minakuchi et al. Atelocollagen-mediated synthetic small interfering RNA delivery for effective gene silencing in vitro and in vivo. Nucleic Acids Research, 32(13):e109, 2004.
Mishima et al. RT-PCR-based analysis of microRNA (miR-1 and -124) expression in mouse CNS. Brain Res, 1131(1):37-43, Epub Dec. 19, 2006. 2007.
Miyake et al. Increased angiogenin expression in the tumor tissue and serum of urothelial carcinoma patients is related to disease progression and recurrence. Cancer, 86 (2):316-324, 1999.
Mizunuma et al. The LIM-only protein, LMO4, and the LIM domain-binding protein, LDB1, expression in squamous cell carcinomas of the oral cavity. Br J Cancer, 88(10):1543-1548, 2003.
Mohanty and Kushner. Polynucleotide phosphorylase functions both as a 3'-5' exonuclease and a poly(A) polymerase in *Escherichia coli*. PNAS, 97:11966-11971; 2000.
Moller et al. Expression of APO-1 (CD95), a member of the NGF/TNF receptor superfamily, in normal and neoplastic colon epithelium. Int J Cancer, 57 (3):371-377, 1994.
Momand et al. The MDM2 gene amplification database. Nucleic Acids Res, 26(15):3453-3459, 1998.
Montero et al. Angiogenin expression and prognosis in primary breast carcinoma. Clin. Cancer Res., 4 (9):2161-2168, 1998.
Mori et al. A genome-wide search identifies epigenetic silencing of somatostatin, tachykinin-1, and 5 other genes in colon cancer. Gastroenterology, 131(3):797-808, 2006.
Morton et al. Sentinel-node biopsy or nodal observation in melanoma. N Engl. J. Med., 355(13):1307-1317, 2006.
Morton et al. Technical details of intraoperative lymphatic mapping for early stage melanoma. Arch Surg, 127(4):392-399, 1992.
Mourelatos et al. miRNPs: a novel class of ribonucleoproteins containing numerous microRNAs. Genes & Development, 16:720-728, 2002.
Mrozek et al. Clinical relevance of mutations and gene-expression changes in adult acute myeloid leukemia with normal cytogenetics: are we ready for a prognostically prioritized molecular classification? Blood. 109:431-448, 2007.
Mundt et al. On the regulation and function of human polo-like kinase 1 (PLK1): effects of overexpression on cell cycle progression. Biochem Biophys Res Commun, 239(2):377-385, 1997.
Muralidhar et al. Global microRNA profiles in cervical squamous cell carcinoma depend on Drosha expression levels. J. Pathol., 212:368-377, 2007.
Murphy et al. p16INK4A, CDC6, and MCM5: predictive biomarkers in cervical preinvasive neoplasia and cervical cancer. J Clin Pathol, 58(5):525-534, 2005.
Nagpal et al. Tazaratone-induced gen 1 (TIG1), a novel retinoic acid receptor-responsive gene in skin. J. Invest. Dermatol. 106 (2):269-274, 1996.
Nakada et al. The phosphorylation of EphB2 receptor regulates migration and invasion of human glioma cells. Cancer Res., 64 (9):3179-3185, 2004.
Nakamura et al. MARCH-II is a syntaxin-6-binding protein involved in endosomal trafficking. Molecular Biology of the Cell, 16(4):1696-1710, 2005.
Nauert et al. Gravin, an autoantigen recognized by serum from myasthenia gravis patients, is a kinase scaffold protein. Curr Biol, 7(1):52-62, 1997.
Nelson et al. Microarray-based, high-throughput gene expression profiling of microRNAs. Nature Methods, 1(2):1-7, 2004.
Nerlov. C/EBPalpha mutations in acute myeloid leukaemias. Nat Rev Cancer, 4(5):394-400, 2004.
Nesbit et al. MYC oncogenes and human neoplastic disease. Oncogene, 18 (19):3004-3016, 1999.
Ngan et al. Quantitative evaluation of vimentin expression in tumour stroma of colorectal cancer. Br J Cancer, 96(6):986-992, 2007.
Nikiforova et al. MicroRNA expression profiling of thyroid tumors: biological significance and diagnostic utility. 93(5):1600-1608, 2008.
Nordgard et al. Quantitative RT-PCR detection of tumor cells in sentinel lymph nodes isolated from colon cancer patients with an ex vivo approach. Annals of Surgery, 249(4):602-607, 2009.
Notice of Allowance and Fee(s) Due and Notice of Allowability mailed Feb. 4, 2013, in U.S. Appl. No. 13/299,255.
Notice of Allowance issued in U.S. Appl. No. 11/141,707, mailed Oct. 4, 2010.
Notice of Allowance issued in U.S. Appl. No. 11/837,490, mailed Apr. 1, 2011.
Notice of Allowance issued in U.S. Appl. No. 11/837,495, mailed Dec. 2, 2010.
Nykanen et al. ATP requirements and small interfering RNA structure in the RNA interference pathway. Cell, 107:309-321, 2001.
Oberg et al. Detection of occult tumour cells in lymph nodes of colorectal cancer patients using real-time quantitative RT-PCR for CEA and CK20 mRNAS. Int. J. Cancer, 111(1):101-110, 2004.
O'Connor et al. Bim: a novel member of the Bc1-2 family that promotes apoptosis. Embo J, 17(2):384-395, 1998.
O'Donnel et al. c-Myc-regulated microRNA's modulcate E2F1 expression. Nature, 435(7043):839-843, 2005.
Office Action issued in Australian Application No. 2005250432, mailed Aug. 25, 2010.
Office Action issued in Australian Application No. 2005250432, mailed Dec. 1, 2009.
Office Action issued in Australian Application No. 2005250432, mailed Jun. 10, 2011.
Office Action issued in Australian Application No. 2005250432, mailed Mar. 29, 2011.
Office Action issued in Australian Application No. 2005333165, mailed Feb. 7, 2011.
Office Action issued in Chinese Application No. 200780050263.1, mailed Mar. 28, 2011, and English language translation thereof.
Office Action issued in European Application No. 02720894.1, mailed Jul. 11, 2007.
Office Action issued in European Application No. 05804851.3, mailed Dec. 21, 2007.
Office Action issued in European Application No. 05804851.3, mailed Jul. 30, 2008.
Office Action issued in European Application No. 05815286.9, mailed Apr. 3, 2008.
Office Action issued in European Application No. 05858321.2, mailed Apr. 11, 2008.
Office Action issued in European Application No. 05858321.2., mailed Apr. 16, 2010.
Office Action issued in European Application No. 07871689.1, mailed Dec. 15, 2009.
Office Action issued in European Application No. 07871690.9, mailed Dec. 14, 2009.
Office Action issued in European Application No. 07871691.7, mailed Dec. 14, 2009.
Office Action issued in European Application No. 07871691.7, mailed Oct. 28, 2010.
Office Action issued in European Application No. 07871693.3, mailed Dec. 9, 2009.
Office Action issued in European Application No. 07871693.3, mailed Oct. 18,2010.
Office Action issued in European Application No. 07871694.1, mailed Dec. 10, 2009.
Office Action issued in European Application No. 07871756.8, mailed Oct. 20, 2009.
Office Action issued in European Application No. 08770269.2, mailed Jul. 30, 2010.

(56) References Cited

OTHER PUBLICATIONS

Office Action issued in European Application No. 08831073.5, mailed Aug. 16, 2010.
Office Action issued in European Application No. 08831073.5, mailed Feb. 25, 2011.
Office Action issued in European Application No. 09154092.2, mailed Apr. 1, 2010.
Office Action issued in European Application No. 09154092.2, mailed May 7, 2009.
Office Action issued in European Application No. 09154092.2, mailed Nov. 10, 2010.
Office Action issued in European Application No. 09717913.9, mailed Mar. 7, 2011.
Office Action issued in Japanese Application No. 2007-515415, mailed Jan. 26, 2011 (and English language translation thereof).
Office Action issued in U.S. Appl. No. 10/632,534, mailed Jul. 11, 2006.
Office Action issued in U.S. Appl. No. 10/632,534, mailed Mar. 24, 2006.
Office Action issued in U.S. Appl. No. 10/632,534, mailed Mar. 29, 2007.
Office Action issued in U.S. Appl. No. 10/632,539, mailed Apr. 17, 2007.
Office Action issued in U.S. Appl. No. 10/632,539, mailed Jul. 27, 2006.
Office Action issued in U.S. Appl. No. 10/632,539, mailed Mar. 27, 2006.
Office Action issued in U.S. Appl. No. 10/880,350, mailed Oct. 4, 2006.
Office Action issued in U.S. Appl. No. 10/880,350, mailed Sep. 10, 2007.
Office Action issued in U.S. Appl. No. 10/963,415, mailed Apr. 13, 2007.
Office Action issued in U.S. Appl. No. 10/963,415, mailed Aug. 2, 2007.
Office Action issued in U.S. Appl. No. 10/963,415, mailed Mar. 17, 2008.
Office Action issued in U.S. Appl. No. 10/963,415, mailed Mar. 9, 2009.
Office Action issued in U.S. Appl. No. 11/141,707, mailed Feb. 9, 2009.
Office Action issued in U.S. Appl. No. 11/141,707, mailed Jan. 6, 2010.
Office Action issued in U.S. Appl. No. 11/141,707, mailed Jul. 17, 2008.
Office Action issued in U.S. Appl. No. 11/141,707, mailed Jun. 19, 2009.
Office Action issued in U.S. Appl. No. 11/141,707, mailed Mar. 11, 2010.
Office Action issued in U.S. Appl. No. 11/141,707, mailed May 15, 2007.
Office Action issued in U.S. Appl. No. 11/141,707, mailed Oct. 17, 2007.
Office Action issued in U.S. Appl. No. 11/141,707, mailed Sep. 2, 2010.
Office Action issued in U.S. Appl. No. 11/273,640, mailed Jul. 26, 2011.
Office Action issued in U.S. Appl. No. 11/273,640, mailed Jun. 26, 2009.
Office Action issued in U.S. Appl. No. 11/273,640, mailed May 5, 2010.
Office Action issued in U.S. Appl. No. 11/273,640, mailed Nov. 20, 2009.
Office Action issued in U.S. Appl. No. 11/567,082, mailed Jan. 27, 2009.
Office Action issued in U.S. Appl. No. 11/567,082, mailed Jul. 21, 2008.
Office Action issued in U.S. Appl. No. 11/567,082, mailed Jul. 3, 2007.
Office Action issued in U.S. Appl. No. 11/567,082, mailed Nov. 13, 2007.
Office Action issued in U.S. Appl. No. 11/567,082, mailed Sep. 30, 2009.
Office Action issued in U.S. Appl. No. 11/837,487, mailed Mar. 25, 2009.
Office Action issued in U.S. Appl. No. 11/837,487, mailed May 28, 2010.
Office Action issued in U.S. Appl. No. 11/837,487, mailed Nov. 22, 2010.
Office Action issued in U.S. Appl. No. 11/837,487, mailed Sep. 15, 2009.
Office Action issued in U.S. Appl. No. 11/837,488, mailed Feb. 15, 2011.
Office Action issued in U.S. Appl. No. 11/837,488, mailed Feb. 19, 2010.
Office Action issued in U.S. Appl. No. 11/837,490, mailed Apr. 9, 2010.
Office Action issued in U.S. Appl. No. 11/837,490, mailed Aug. 18, 2009.
Office Action issued in U.S. Appl. No. 11/837,490, mailed Aug. 6, 2008.
Office Action issued in U.S. Appl. No. 11/837,490, mailed Jan. 13, 2009.
Office Action issued in U.S. Appl. No. 11/837,494, mailed Jan. 15, 2009.
Office Action issued in U.S. Appl. No. 11/837,494, mailed Jan. 5, 2010.
Office Action issued in U.S. Appl. No. 11/837,494, mailed Mar. 5, 2009.
Office Action issued in U.S. Appl. No. 11/837,494, mailed Oct. 30, 2008.
Office Action issued in U.S. Appl. No. 11/837,495, mailed Jan. 5, 2010.
Office Action issued in U.S. Appl. No. 11/837,495, mailed Mar. 5, 2009.
Office Action issued in U.S. Appl. No. 11/837,495, mailed Oct. 30, 2008.
Office Action issued in U.S. Appl. No. 11/837,495, mailed Sep. 2, 2010.
Office Action issued in U.S. Appl. No. 11/837,498, mailed Apr. 30, 2009.
Office Action issued in U.S. Appl. No. 11/837,498, mailed Jan. 15, 2009.
Office Action issued in U.S. Appl. No. 11/837,498, mailed May 7, 2010.
Office Action issued in U.S. Appl. No. 11/837,498, mailed Nov. 20, 2009.
Office Action issued in U.S. Appl. No. 11/837,498, mailed Oct. 29, 2008.
Office Action issued in U.S. Appl. No. 11/857,948, mailed Aug. 24, 2010.
Office Action issued in U.S. Appl. No. 11/857,948, mailed Jan. 26, 2011.
Office Action issued in U.S. Appl. No. 11/857,948, mailed Jun. 4, 2009.
Office Action issued in U.S. Appl. No. 11/857,948, mailed May 25, 2010.
Office Action issued in U.S. Appl. No. 11/857,948, mailed Nov. 3, 2009.
Office Action issued in U.S. Appl. No. 11/953,606, mailed Aug. 10, 2009.
Office Action issued in U.S. Appl. No. 11/953,606, mailed Jan. 8, 2010.
Office Action issued in U.S. Appl. No. 11/953,606, mailed Jul. 1, 2010.
Office Action issued in U.S. Appl. No. 11/953,606, mailed Oct. 1, 2010.
Office Action issued in U.S. Appl. No. 11/967,639, mailed Mar. 13, 2009.
Office Action issued in U.S. Appl. No. 11/967,639, mailed Mar. 24, 2010.

(56) References Cited

OTHER PUBLICATIONS

Office Action issued in U.S. Appl. No. 11/967,639, mailed May 14, 2010.
Office Action issued in U.S. Appl. No. 11/967,663, mailed Feb. 12, 2010.
Office Action issued in U.S. Appl. No. 11/967,663, mailed Oct. 1, 2009.
Office Action issued in U.S. Appl. No. 12/112,291, mailed Mar. 1, 2010.
Office Action issued in U.S. Appl. No. 12/112,291, mailed Nov. 16, 2009.
Office Action issued in U.S. Appl. No. 12/120,388, mailed Feb. 19, 2010.
Office Action issued in U.S. Appl. No. 12/120,388, mailed Jul. 21, 2010.
Office Action issued in U.S. Appl. No. 12/124,394, mailed Feb. 5, 2010.
Office Action issued in U.S. Appl. No. 12/124,394, mailed Nov. 6, 2009.
Office Action issued in U.S. Appl. No. 12/125,412, mailed Feb. 16, 2010.
Office Action issued in U.S. Appl. No. 12/125,412, mailed Nov. 12, 2009.
Office Action issued in U.S. Appl. No. 12/125,675, mailed Apr. 22, 2010.
Office Action issued in U.S. Appl. No. 12/125,675, mailed Jan. 28, 2011.
Office Action issued in U.S. Appl. No. 12/125,675, mailed Oct. 14, 2010.
Office Action issued in U.S. Appl. No. 12/125,675, mailed Sep. 10, 2009.
Office Action issued in U.S. Appl. No. 12/134,932, mailed Feb. 24, 2011.
Office Action issued in U.S. Appl. No. 12/134,932, mailed Mar. 24, 2010.
Office Action issued in U.S. Appl. No. 12/134,932, mailed Nov. 12, 2009.
Office Action issued in U.S. Appl. No. 12/134,932, mailed Nov. 4, 2010.
Office Action issued in U.S. Appl. No. 12/167,492, mailed Aug. 12, 2010.
Office Action issued in U.S. Appl. No. 12/167,492, mailed Feb. 12, 2010.
Office Action issued in U.S. Appl. No. 12/167,492, mailed Feb. 25, 2011.
Office Action issued in U.S. Appl. No. 12/167,492, mailed Jun. 7, 2011.
Office Action issued in U.S. Appl. No. 12/209,822, mailed Mar. 15, 2011.
Office Action issued in U.S. Appl. No. 12/253,718, mailed Apr. 22, 2011.
Office Action issued in U.S. Appl. No. 12/253,718, mailed Jun. 11, 2010.
Office Action issued in U.S. Appl. No. 12/253,718, mailed Nov. 1, 2010.
Office Action issued in U.S. Appl. No. 12/325,917, mailed Apr. 22, 2011.
Office Action issued in U.S. Appl. No. 12/325,917, mailed Feb. 14, 2011.
Office Action issued in U.S. Appl. No. 12/325,917, mailed Jul. 28, 2010.
Office Action issued in U.S. Appl. No. 12/325,917, mailed May 3, 2010.
Office Action issued in U.S. Appl. No. 12/340,329, mailed Sep. 28, 2010.
Office Action issued in U.S. Appl. No. 12/368,053, mailed Aug. 19, 2010.
Office Action issued in U.S. Appl. No. 12/368,053, mailed Dec. 21, 2010.
Office Action issued in U.S. Appl. No. 12/368,053, mailed Jun. 22, 2011.
Office Action issued in U.S. Appl. No. 12/398,852, mailed Aug. 11, 2011.
Office Action issued in U.S. Appl. No. 12/398,852, mailed Mar. 7, 2011.
Office Action issued in U.S. Appl. No. 12/412,087, mailed Apr. 22, 2011.
Office Action issued in U.S. Appl. No. 12/412,087, mailed Aug. 18, 2011.
Office Action issued in U.S. Appl. No. 12/420,634, mailed Apr. 29, 2011.
Office Action issued in U.S. Appl. No. 12/420,634, mailed Aug. 30, 2010.
Office Action issued in U.S. Appl. No. 12/420,634, mailed May 26, 2010.
Office Action issued in U.S. Appl. No. 12/616,616, mailed Aug. 13, 2010.
Office Action issued in U.S. Appl. No. 10/880,350, mailed Feb. 21, 2006.
Office Communication issued in Japanese Patent Application No. 2007-541398, dated Jun. 4, 2012. (English translation).
Office Action issued in U.S. Appl. No. 11/967,639, mailed May 14, 2009.
Ohlsson et al. Biomarker selection for detection of occult tumour cells in lymph nodes of colorectal cancer patients using real-time quantitative RT-PCR. Br. J. Cancer, 95(2):218-225, 2006.
Ohsaki et al. Antitumor activity of magainin analogues against human lung cancer cell lines. Cancer Res, 52(13):3534-3538, 1992.
Ollila et al. Metastatic melanoma cells in the sentinel node cannot be ignored. J. Am. Coll. Surg., 208(5):924-929, 2009.
Olsen and Ambros. The lin-4 regulatory RNA controls developmental timing in Caenorhabditis elegans by blocking LIN-14 protein synthesis after the initiation of translation. Dev. Biol., 216:671, 1999.
Opalinska and Gewirtz. Nucleic-acid therapeutics: basic principles and recent applications. Nature Reviews, 1:503-514, 2002.
Ovcharenko et al. High-throughput RNAi screening in vitro: from cell lines to primary cells. RNA, 11(6):985-93, 2005.
Ozaki et al. Blockade of vascular endothelial cell growth factor receptor signaling is sufficient to completely prevent retinal neovascularization. Am. J. Pathol., 156(2):697-707, 2000.
Paik et al. FoxOs are lineage-restricted redundant tumor suppressors and regulate endothelial cell homeostasis. Cell, 128(2):309-323, 2007.
Palleres et al. Structure of human carboxypeptidase A4: with its endogenous protein inhibitor, latexin. Proc. Natl. Acad. Sci. USA, 102:3978-3983, 2005.
Paramo et al. Validation of sentinel node mapping in patients with colon cancer. Ann Surg Oncol, 9(6):550-554, 2002.
Parkin et al. Global cancer statistics, 2002. CA Cancer J. Clin., 55(2):74-108, 2005.
Pasquinelli and Ruvkun. Control of developmental timing by micrornas and their targets. Ann. Rev. Cell Dev. Biol., 18:495-513, 2002.
Pasquinelli et al. Reverse 5' caps in RNAs made in vitro by phage RNA polymerases. RNA, 1:957-967, 1995.
Patrawala et al. Hierarchical organization of prostate cancer cells in xenograft tumors: the CD44+alpha2beta1+ cell population is enriched in tumor-initiating cells. Cancer Res., 67(14):6796-805, 2007.
Patrawala et al. Highly purified CD44+ prostate cancer cells from xenograft human tumors are enriched in tumorigenic and metastatic progenitor cells. Oncogene, 25(12):1696-708, 2006.
Patrawala et al. Side population is enriched in tumorigenic, stem-like cancer cells, whereas ABCG2+ and ABCG2− cancer cells are similarly tumorigenic. Cancer Res., 65(14):6207-19, 2005.
Patrawala et al. MicroRNAs in prostate cancer stem cells, AACR Cancer Stem Cell Special Conference—Los Angeles, Feb. 12-15, 2008.
Payton and Coats. Cyclin E2, the cycle continues. Int J Biochem Cell Biol, 34(4):315-320, 2002.

(56) References Cited

OTHER PUBLICATIONS

Payton et al. Deregulation of cyclin E2 expression and associated kinase activity in primary breast tumors. Oncogene, 21(55):8529-8534, 2002.
PCT International Preliminary Report on Patentability and Written Opinion, issued in International Application No. PCT/US2005/018826, mailed Dec. 7, 2006.
PCT International Preliminary Report on Patentability and Written Opinion, issued in International Application No. PCT/US2005/036799, mailed Apr. 26, 2007.
PCT International Preliminary Report on Patentability and Written Opinion, issued in International Application No. PCT/US2007/086396, mailed Jun. 18, 2009.
PCT International Preliminary Report on Patentability and Written Opinion, issued in International Application No. PCT/US2007/087021, mailed Jun. 18, 2009.
PCT International Preliminary Report on Patentability and Written Opinion, issued in International Application No. PCT/US2007/087029, mailed Jun. 18, 2009.
PCT International Preliminary Report on Patentability and Written Opinion, issued in International Application No. PCT/US2007/087031, mailed Jun. 18, 2009.
PCT International Preliminary Report on Patentability and Written Opinion, issued in International Application No. PCT/US2007/087033, mailed Jun. 18, 2009.
PCT International Preliminary Report on Patentability and Written Opinion, issued in International Application No. PCT/US2007/087037, mailed Jun. 18, 2009.
PCT International Preliminary Report on Patentability and Written Opinion, issued in International Application No. PCT/US2007/087038, mailed Jun. 18, 2009.
PCT International Preliminary Report on Patentability and Written Opinion, issued in International Application No. PCT/US2007/089206, mailed Jun. 18, 2009.
PCT International Preliminary Report on Patentability and Written Opinion issued in International Application No. PCT/US2008/080318, mailed Apr. 29, 2010.
PCT International Preliminary Report on Patentability and Written Opinion issued in International Application No. PCT/US2008/085178, mailed Jun. 10, 2010.
PCT International Preliminary Report on Patentability and Written Opinion issued in International Application No. PCT/US2008/087762, mailed Jul. 1, 2010.
PCT International Preliminary Report on Patentability, issued in International Application No. PCT/US2007/078859, mailed Apr. 2, 2009.
PCT International Preliminary Report on Patentability, issued in International Application No. PCT/US2007/078894, mailed Apr. 2, 2009.
PCT International Preliminary Report on Patentability, issued in International Application No. PCT/US2007/078936, mailed Apr. 2, 2009.
PCT International Preliminary Report on Patentability issued in International Application No. PCT/US2007/078952, mailed Feb. 11, 2010.
PCT International Preliminary Report on Patentability issued in International Application No. PCT/US2008/066025, mailed Dec. 23, 2009.
PCT International Preliminary Report on Patentability issued in International Application No. PCT/US2008/076246, mailed Mar. 16, 2010.
PCT International Preliminary Report on Patentability issued in International Application No. PCT/US2009/033556, mailed Aug. 19, 2010.
PCT International Preliminary Report on Patentability issued in International Application No. PCT/US2009/036195, mailed Sep. 16, 2010.
PCT International Preliminary Report on Patentability issued in International Application No. PCT/US2009/038399, mailed Oct. 7, 2010.
PCT International Preliminary Report on Patentability issued in International Application No. PCT/US2009/039935, mailed Oct. 21, 2010.
PCT International Preliminary Report on Patentability issued in International Application No. PCT/US2009/043361, mailed Nov. 18, 2010.
PCT International Search Report and Written Opinion, issued in International Application No. PCT/US2005/036799, mailed Jun. 22, 2006.
PCT International Search Report and Written Opinion, issued in International Application No. PCT/US2005/041162, mailed Nov. 16, 2007.
PCT International Search Report and Written Opinion, issued in International Application No. PCT/US2007/078859, mailed Mar. 25, 2008.
PCT International Search Report and Written Opinion, issued in International Application No. PCT/US2007/078894, mailed Apr. 14, 2008.
PCT International Search Report and Written Opinion, issued in International Application No. PCT/US2007/078936, mailed Apr. 14, 2008.
PCT International Search Report and Written Opinion, issued in International Application No. PCT/US2007/078952, mailed Jan. 26, 2010.
PCT International Search Report and Written Opinion, issued in International Application No. PCT/US2007/086396, mailed May 30, 2008.
PCT International Search Report and Written Opinion, issued in International Application No. PCT/US2007/087021, mailed Sep. 3, 2008.
PCT International Search Report and Written Opinion, issued in International Application No. PCT/US2007/087029, mailed Jan. 13, 2009.
PCT International Search Report and Written Opinion, issued in International Application No. PCT/US2007/087031, mailed Jan. 13, 2009.
PCT International Search Report and Written Opinion, issued in International Application No. PCT/US2007/087033, mailed Jan. 13, 2009.
PCT International Search Report and Written Opinion, issued in International Application No. PCT/US2007/087037, mailed Jan. 12, 2009.
PCT International Search Report and Written Opinion, issued in International Application No. PCT/US2007/087038, mailed Oct. 17, 2008.
PCT International Search Report and Written Opinion, issued in International Application No. PCT/US2007/089206, mailed Aug. 26, 2008.
PCT International Search Report and Written Opinion issued in International Application No. PCT/US2008/066025, mailed Sep. 16, 2009.
PCT International Search Report and Written Opinion issued in International Application No. PCT/US2008/076246, mailed Feb. 27, 2009.
PCT International Search Report and Written Opinion issued in International Application No. PCT/US2008/080318, mailed Feb. 9, 2009.
PCT International Search Report and Written Opinion issued in International Application No. PCT/US2008/085178, mailed Aug. 21, 2009.
PCT International Search Report and Written Opinion issued in International Application No. PCT/US2008/087762, mailed Mar. 16, 2010.
PCT International Search Report and Written Opinion issued in International Application No. PCT/US2009/033556, mailed Aug. 4, 2009.
PCT International Search Report and Written Opinion issued in International Application No. PCT/US2009/036195, mailed Sep. 4, 2009.
PCT International Search Report and Written Opinion issued in International Application No. PCT/US2009/038399, mailed Mar. 3, 2010.

(56) References Cited

OTHER PUBLICATIONS

PCT International Search Report and Written Opinion issued in International Application No. PCT/US2009/039935, mailed Sep. 17, 2009.
PCT International Search Report and Written Opinion issued in International Application No. PCT/US2009/043361, mailed Nov. 4, 2009.
PCT International Search Report and Written Opinion issued in International Application No. PCT/US2009/064015, mailed Jul. 26, 2010.
PCT International Search Report, issued in International Application No. PCT/US2002/003169, mailed Feb. 17, 2003.
PCT Invitation to Pay Additional Fees and Partial International Search, issued in International Application No. PCT/US2005/018826, mailed Mar. 20, 2006.
PCT Invitation to Pay Additional Fees and Partial International Search, issued in International Application No. PCT/US2005/041162, mailed Aug. 31, 2007.
PCT Invitation to Pay Additional Fees and Partial International Search, issued in International Application No. PCT/US2007/078859, mailed Jan. 28, 2008.
PCT Invitation to Pay Additional Fees and Partial International Search, issued in International Application No. PCT/US2007/078894, mailed Feb. 11, 2008.
PCT Invitation to Pay Additional Fees and Partial International Search, issued in International Application No. PCT/US2007/078936, mailed Feb. 5, 2008.
PCT Invitation to Pay Additional Fees and Partial International Search, issued in International Application No. PCT/US2007/087021, mailed Jul. 10, 2008.
PCT Invitation to Pay Additional Fees and Partial International Search, issued in International Application No. PCT/US2007/087029, mailed Sep. 10, 2008.
PCT Invitation to Pay Additional Fees and Partial International Search, issued in International Application No. PCT/US2007/087031, mailed Sep. 10, 2008.
PCT Invitation to Pay Additional Fees and Partial International Search, issued in International Application No. PCT/US2007/087033, mailed Sep. 5, 2008.
PCT Invitation to Pay Additional Fees and Partial International Search, issued in International Application No. PCT/US2007/087037, mailed Aug. 25, 2008.
PCT Invitation to Pay Additional Fees and Partial International Search, issued in International Application No. PCT/US2007/087038, mailed Jul. 16, 2008.
PCT Invitation to Pay Additional Fees and Partial International Search, issued in International Application No. PCT/US2007/089206, mailed Jul. 7, 2008.
PCT Invitation to Pay Additional Fees and Partial International Search, issued in International Application No. PCT/US2008/076246, mailed Dec. 30, 2008.
PCT Invitation to Pay Additional Fees and Partial International Search, issued in International Application No. PCT/US2008/085178, mailed May 8, 2009.
PCT Invitation to Pay Additional Fees and Partial International Search, issued in International Application No. PCT/US2009/033556, mailed Jun. 5, 2009.
PCT Invitation to Pay Additional Fees and Partial International Search, issued in International Application No. PCT/US2009/036195, mailed Jul. 2, 2009.
PCT Invitation to Pay Additional Fees and Partial International Search, issued in International Application No. PCT/US2009/043361, mailed Jul. 22, 2009.
PCT Invitation to Pay Additional Fees issued in International Application No. PCT/US2007/078952, mailed Sep. 22, 2009.
PCT Invitation to Pay Additional Fees issued in International Application No. PCT/US2008/087762, mailed Nov. 9, 2009.
Peacock et al. Hedgehog signaling maintains a tumor stem cell compartment in multiple myeloma. Proc. Natl. Acad. Sci. USA, 104(10):4048-53, 2007.
Pendas et al. Worldwide experience with lymphatic mapping for invasive breast cancer. Semin. Oncol., 31(3):318-323, 2004.
Peng et al. Overexpression of microRNA let-7c in prostate cancer. Modern Pathology, Abstract No. 788, 20 (Suppl. 2):169A, 2007.
Peracchi. Prospects for antiviral ribozymes and deoxyribozymes. Rev. Med. Virol., 14:47-64, 2004.
Petit et al. LHFP, a novel translocation partner gene of HMGIC in a lipoma, is a member of a new family of LHFP-like genes. Genomics, 57 (3):438-441, 1999.
Phan et al. Sentinel lymph node biopsy for melanoma: indications and rationale. Cancer Control, 16(3):234-239, 2009.
Phillips et al. Antisense RNA amplification: A linear amplification method for analyzing the mRNA populaion. Methods, a Companion to Methods in Enzymology, 10(3):283-288, 1996.
Pietras et al. PDGF receptors as cancer drug targets. Cancer Cell, 3(5):439-443, 2003.
Poliseno et al. MicroRNAs modulate the angiogenic properties of HUVECs. Blood 108(9):3068-3071, 2006.
Porkka et al. MicroRNA expression profiling in prostate cancer. Cancer Res., 67(13):6130-6135, 2007.
Poster Abstracts, Annals of Surgical Oncology, 15(Suppl1):33-64, 2008.
Pretlow et al. K-ras mutations in putative preneoplastic lesions in human colon. J. Natl Cancer Inst., 85(24):2004-2007, 1993.
Qian et al. Expression profiling of CD34+ hematopoietic stem/progenitor cells reveals distinct subtypes of therapy-related acute myeloid leukemia. Proc Natl Acad Sci USA. 99(23):14925-14930, 2002.
Quan et al. The evolution of lymph node assessment in breast cancer. Journal of Surgical Oncology, 2008.
Rader et al. In vitro differentiation of epithelial cells from cervical neoplasias resembles in vivo lesions. Oncogene, 5(4):571-6, 1990.
Rapp et al. Structure and biological activity of v-raf, a unique oncogene transduced by a retrovirus. Proc Natl Acad Sci USA. 80(14):4218-4222, 1983.
Redston et al. Analysis of micrometastatic disease in sentinel lymph nodes from resectable colon cancer: results of Cancer and Leukemia Group B Trial 80001. J Clin. Oncol. 24(6):878-883, 2006.
Ree et al. Expression of a novel factor in human breast cancer cells with metastatic potential. Cancer Res., 59 (18):4675-4680, 1999.
Reimer et al. Altered regulation of cyclin G in human breast cancer and its specific localization at replication foci in response to DNA damage in p53+/+ cells. Biol. Chem., 274 (16): 11022-11029, 1999.
Reinhart et al. The 21-nucleotide let-7 RNA regulates developmental timing in Caenorhabditis elegans. Nature,. 403:901-906, 2000.
Reintgen et al. Sentinel Node Biopsy in Breast Cancer: An Overview. Breast 1, 6(5):299-305, 2000.
Reiter and Sawyers. Xenograft models and the molecular biology of human prostate cancer. In: Prostate Cancer: Biology, Genetics, and the New Therapeutics, Totowa, NJ, 163-173, 2001.
Reshmi and Pillai. Beyond HPV: oncomirs as new players in cervical cancer. FEBS Letters, 582:4113-4116, 2008.
Richardson et al. CD133, a novel marker for human prostatic epithelial stem cells. J Cell Sci., 117(Pt 16):3539-45, 2004.
Rickert et al. Multiplexed Real-Time PCR Using Universal Reporters. Clin. Chem., 50(9):1680-1683, 2004.
Roberts et al. Interpretive disparity among pathologists in breast sentinel lymph node evaluation. Am. J. Surg., 186:324-329, 2003.
Rosenfeld et al. Ranibizumab: Phase III clinical trial results. Ophthalmol. Clin. North Am. 19(3):361-372, 2006.
Rosenkilde and Schwartz. The chemokine system—a major regulator of angiogenesis in health and disease. Apmis, 112(7-8):481-495, 2004.
Rossi et al. Identification of inactivating mutations in the JAK1, SYNJ2, and CLPTM1 genes in prostate cancer cells using inhibition of nonsense-mediated decay and microarray analysis. Cancer Genet. Cytogenet. 161 (2): 97-103, 2005.
Rous. A sarcoma of the fowl transmissible by an agent separable from the tumor cells. J Exp Med, 13:397-411, 1911.
Rubin and Gutmann. Neurofibromatosis type 1—a model for nervous system tumour formation?. Nat Rev Cancer, 5(7):557-564, 2005.
Ruth et al. RhoC promotes human melanoma invasion in a PI3K/Akt-dependent pathway. J. Invest. Dermatol. 126 (4): 862-868, 2006.

(56) References Cited

OTHER PUBLICATIONS

Ryan et al. MicroRNAs of the mammalian eye display distinct and overlapping tissue specificity. Molecular Vision, 12:1175-1184, 2006.
Sacchi et al. Hu-ets-1 and Hu-ets-2 genes are transposed in acute leukemias with (4;11) and (8;21) translocations. Science, 231 (4736):379-382, 1986.
Saha et al. Historical review of lymphatic mapping in gastrointestinal malignancies. Ann Surg Oncol, 11(3 Suppl):2455-2495, 2004.
Saha et al. Ultrastaging of colorectal cancer by sentinel lymph node mapping technique—a multicenter trial. Ann. Surg. Oncol., 8(9 Suppl):94S-98S, 2001.
Saigusa et al. Overexpressed Skp2 within 5p amplification detected by array-based comparative genomic hybridization is associated with poor prognosis of glioblastomas. Cancer Sci, 96(10):676-683, 2005.
Saitoh et al. Frequent up-regulation of WNT5A mRNA in primary gastric cancer. Int. J. Mol. Med., 9 (5): 515-519, 2002.
Saiz et al. MicroRNA expression profiling in acute myelogenous leukemia. Blood, ASH Annual Meeting Abstracts, 104:320a, Abstract No. 1131, Poster board No. session 285-I, 2004.
Sakai et al. Microarray hybridization with fractionated cDNA: enhanced identification of differentially expressed genes. Analytical Biochemistry, 287(1):32-37, 2000.
Sampson and Uhlenbeck. Biochemical and physical characterization of an unmodified yeast phenylalanine transfer RNA transcribed in vitro. Proc. Natl. Acad. Sci., USA, 85(4):1033-1037, 1988.
Sanger Institute. miRBase miRBase Sequence Database, located at http://microrna.sanger.ac.uk/, printed Jan. 21, 2009.
Sanger Institute, miRBase::SequencesStem loop sequence M10000268, Sep. 2008, [online], The Wellcome Trust Sanger Institute,; [retrieved on Dec. 23, 2008], URL: http://microRNA.sangerac_uk.
Sasaki et al. Expression of the MTA1 mRNA in advanced lung cancer. Lung Cancer, 35(2):149-154, 2002.
Scaria et al. Host-virus genome interactions: macro roles for microRNAs. Cell Microbiol., (12):2784-94 2007.
Scaria et al. Host-virus interaction: a new role for microRNAs. Retrovirology, 3:68, 2006.
Schenborn and Stecha. Ribo m7G cap analog: A reagent for preparing in vitro capped transcripts, Promega Notes, 74:18-20, 2000.
Schepeler et al. Diagnostic and prognostic microRNAs in stage II colon cancer. Cancer Research, 68(15):6416-6424, 2008.
Scherer and Rossi. Approaches for the sequence-specific knockdown of mRNA. Nat. Biotechnol., 21(12):1457-1465, 2003.
Scherr- et al. Lentivirus-mediated antagomir expression for specific inhibition of miRNA function. Nucleic Acids Research, 35(22):e149, 2007.
Scherr et al. Modulation of gene expression by lentiviral-mediated delivery of small interfering RNA. Cell Cycle, 2(3):251-257, 2003.
Schetter et al. MicroRNA expression profiles associated with prognosis and therapeutic outcome in colon adenocarcinoma. JAMA, 299(4):425-436, 2008.
Schouten et al. Relative quantification of 40 nucleic acid sequences by multiplex ligation-dependent probe amplification. Nucleic Acids Research, 30(12):e57, 2002. 0.
Schulze-Bergkamen et al. Suppression of Mc1-1 via RNA interference sensitizes human hepatocellular carcinoma cells towards apoptosis induction. BMC Cancer, 6:232, 2006.
Schurr et al. Lymphatic spread and microinvolvement in adenocarcinoma of the esophago-gastric junction. J. Surg. Oncol., 94:307-315, 2006.
Schuster and Porse. C/EBPalpha: a tumour suppressor in multiple tissues? Biochim Biophys Acta, 1766(1):88-103, 2006.
Schwarz et al., Asymmetry in the assembly of the RNAi enzyme complex. Cell, 115:199-208,2003.
Scoggins et al. Prospective multi-institutional study of reverse transcriptase polymerase chain reaction for molecular staging of melanoma. J Clin. Oncol., 24:2849-2857, 2006.

Scott et al., BCL2 antisense reduces prostate cancer cell survival following irradiation. Cancer Biotherapy & Radiopharmaceuticals, 17(6):647-656, 2002.
Segal et al. A module map showing conditional activity of expression modules in cancer. Nature Genetics, 36(10):1090-1098, 2004.
Seggerson et al. Two genetic circuits repress the Caenorhabditis elegans heterochronic gene lin-28 after translation initiation. Dev. Biol., 243:225, 2002.
Sellner et al. Reverse transcriptase inhibits Taq polymerase activity. Nucleic Acids Research, 20(7):1487-1490, 1992.
Sementchenko et al. ETS2 function is required to maintain the transformed state of human prostate cancer cells. Oncogene, 17 (22):2883-2888, 1998.
Semple and Duncker. ORC-associated replication factors as biomarkers for cancer. Biotechnol Adv, 22(8):621-631, 2004.
Sevignani et al. Mammalian microRNAs: a small world for fine-tuning gene expression. _Hamm. Genome, 17(3):189-202, 2006.
Shah et al. FGFR4 overexpression in pancreatic cancer is mediated by an intronic enhancer activated by HNF1alpha. Oncogene, 21 (54):8251-8261, 2002.
Shelly et al. Epiregulin is a potent pan-ErbB ligand that preferentially activates heterodimeric receptor complexes. J Biol. Chem., 273 (17):10496-10505, 1998.
Shelton et al. MicroRNAs and Human Cancer. Abstract submitted for a Cold Spring Symposium in early Jun., 2006—71st Symposium: Regulatory RNAs.
Shen et al. MicroRNAs regulate ocular neovascularization. Molecular Therapy, 16(7):1208-1216,2008.
Shen et al. Oxidative damage in age-related macular degeneration. Histol. Histopathol. 22(12):1301-1308, 2007.
Shen et al. Suppression of ocular neovascularization with siRNA targeting VEGF receptor 1. Gene Therapy, 13:225-234, 2006.
Shepherd et al. Expression profiling of CD133+ and CD133− epithelial cells from human prostate. Prostate, 68(9):1007-1024, 2008.
Sherr and McCormick. The Bb and p53 pathways in cancer. Cancer Cell, 2(2):103-112, 2002.
Sherr and Roberts. CDK inhibitors: positive and negative regulators of G1-phase progression. Genes Dev, 13(12):1501-1512, 1999.
Shi et al. Facile means for quantifying microRNA expression by real-time PCR. BioTechniques, 39(4):519-524, 2005.
Shibahara et al. Down-regulation of Skp2 is correlated with p27-associated cell cycle arrest induced by phenylacetate in human prostate cancer cells. Anticancer Res., 25 (3b):1881-1888, 2005.
Shigemasa et al. Increased MCL-1 expression is associated with poor prognosis in ovarian carcinomas. Jpn. J. Cancer Res., 93(5):542-550, 2002.
Shimo et al. Connective tissue growth factor as a major angiogenic agent that is induced by hypoxia in a human breast cancer cell line. Cancer Lett. 174(1):57-64, 2001.
Shimoyama et al. Increased serum angiogenin concentration in colorectal cancer is correlated with cancer progression. Clin. Cancer Res., 5 (5):1125-1130, 1999.
Shingara et al. An optimized isolation and labeling platform for accurate microRNA expression profiling. RNA, 11:1461-1470, 2005.
Shipitsin et al. Molecular definition of breast tumor heterogeneity. Cancer Cell, 11(3):259-73, 2007.
Shuldiner et al. RNA template-specific polymerase chain reaction RS-PCR a novel strategy to reduce dramatically false positives. Gene, 91(1):139-142, 1990.
Shyu et al. RARRES3 expression positively correlated to tumour differentation in tissues of colorectal adenocarcinoma. Br. J. Cancer, 89 (1):146-151, 2003.
Si et al. miR-21-mediated tumor growth. Oncogene, 1-5, 2006.
Si et al. miR-21-mediated tumor growth. Oncogene, 26(19):2799-2803, 2007.
Simpson et al. Altered expression of Erg and Ets-2 transcription factors is associated with genetic changes at 21q22.2-22.3 in immortal and cervical carcinoma cell lines. Oncogene, 14 (18):2149-2157, 1997.
Singh et al. Identification of a cancer stem cell in human brain tumors. Cancer Res., 63(18):5821-8, 2003.

(56) References Cited

OTHER PUBLICATIONS

Singh et al. Overexpression of vimentin: role in the invasive phenotype in an androgen-independent model of prostate cancer. Cancer Res, 63(9):2306-2311, 2003.
Sinner et al. Sox17 and Sox4 differentially regulate beta-catenin/T-cell factor activity and proliferation of colon carcinoma cells. Mol. Cell Biol., 27(22):7802-15, 2007.
Sirera et al. The analysis of serum DNA concentration by means of hTERT quantification: A useful prognostic factor in advanced non-small cell lung cancer (NSCLC). Lung Cancer, 49:S74, Abstract PD-026, 2005.
Skotzko et al. Retroviral vector-mediated gene transfer of antisense cyclin G1 (CYCG1) inhibits proliferation of human osteogenic sarcoma cells. Cancer Res., 55 (23):5493-5498, 1995.
Slaby et al. Altered expression of miR-21, miR-31, miR-143 and miR-145 is related to clinicopathologic features of colorectal cancer. Oncology, 72(5-6):397-402, 2007.
Slack. Control of Development by microRNAs. Believed at the time of the filing of this form to have been presented by Frank Slack at IIT Bombay on Jan. 28, 2004.
Slack. Control of Development by microRNAs. Believed at the time of the filing of this form to have been presented by Frank Slack at Keystone miRNAs on Apr. 15, 2005.
Slack. Control of Development by microRNAs. Believed at the time of the filing of this form to have been presented by Frank Slack at UCT on Feb. 17, 2004.
Slack. Control of Development by microRNAs. Believed at the time of the filing of this form to have been presented by Frank Slack at UNMC on Mar. 26, 2004.
Slack. Control of developmental timing by microRNAs. Believed at the time of the filing of this form to have been presented by Frank Slack at Santa Cruz in Aug. 2004.
Slack et al. The lin-41 RBCC gene acts in the C. elegans heterochronic pathway between the let-7 regulatory RNA and the LIN-29 transcription factor. Molec. Cell, 5(4):659-669, 2000.
Slack. Small RNA genes as potential causes and treatments of cancer. Believed at the time of the filing of this form to have been presented by Frank Slack at Jaslok on Feb. 1, 2004.
Slack. MicroRNA control of oncogene expression. Believed at the time of the filing of this form to have been presented by Frank Slack at Slack GTBIO on Nov. 8, 2004.
Slack. MicroRNAs and cancer. Believed at the time of the filing of this form to have presented by Frank Slack at University of Puerto Rico Bayamon on Sep. 22, 2004.
Slack. Multiple, dynamic microRNA ribonucleoprotein complexes with select microRNA cargos in C. elegans. Believed at the time of the filing of this form to have been presented by Frank Slack at Gordon on Jun. 8, 2004.
Slack, Temporal patterning and biological timing, believed at the time of the filing of this form to have been presented by Frank Slack at Dartmouth on Mar. 19, 2004.
Smirnova et al. Regulation of miRNA expression during neural cell specification. Eur J Neurosci, 21(6):1469-1477, 2005.
Smith et al. Exclusive amplification of cDNA template (EXACT) RT-PCR to avoid amplifying contaminating genomic pseudogenes. BioTechniques, 31(4):776-778, 780, 782, 2001.
Smith et al. Human papillomavirus type distribution in invasive cervical cancer and high-grade cervical lesions: a meta-analysis update. Int. J. Cancer, 121(3):621-32, 2007.
Smith et al. Malignant transformation of mammalian cells initiated by constitutive expression of the polo-like kinase. Biochem Biophys Res Commun, 234(2):397-405, 1997.
Smith et al. Overexpression of aurora B kinase (AURKB) in primary non-small cell lung carcinoma is frequent, generally driven from one allele, and correlates with the level of genetic instability. Br J Cancer, 93(6):719-729, 2005.
Smith et al. Oxygen-induced retinopathy in the mouse. Invest. Ophthalmol. Vis. Sci. 35(1):101-111, 1994.

Sommers et al. Loss of epithelial markers and acquisition of vimentin expression in adriamycin- and vinblastine-resistant human breast cancer cell lines. Cancer Res, 52(19):5190-5197, 1992.
Sparmann and Bar-Sagi. Ras-induced interleukin-8 expression plays a critical role in tumor growth and angiogenesis. Cancer Cell, 6(5):447-458, 2004.
Stehelin et al. DNA related to the transforming gene(s) of avian sarcoma viruses is present in normal avian DNA. Nature, 260(5547):170-173, 1976.
Stepinski et al. Synthesis and properties of mRNAs containing the novel 'anti-reverse' cap analogs 7-methyl(3'0-methyl)GpppG and 7-methyl(e'-deoxy)GpppG. RNA, 7:1486-1495, 2001.
Stone et al. Isolation of a human prostate carcinoma cell line (DU 145). Int. J Cancer, 21 (3):274-281, 1978.
Strebhardt and Ullrich. Targeting polo-like kinase 1 for cancer therapy. Nat. Rev. Cancer, 6 (4):321-330, 2006.
Sturniolo et al. A novel tumor suppressor protein promotes keratinocyte terminal differentiation via activation of type I transglutaminase, 1 Biol. Chem., 278 (48):48066- 48073, 2003.
Su et al,. Overexpression of p8 is inversely correlated with apoptosis in pancreatic cancer. Clin. Cancer Res., 7 (5):1320-1324, 2001.
Sueoka et al. Detection of plasma hnRNP B1 mRNA, a new cancer biomarker, in lung cancer patients by quantitative real-time polymerase chain reaction. Lung Cancer, 48(1):77-83, 2005.
Suh et al. Human embryonic stem cells express a unique set of microRNAs. Developmental Biology, 270:488-498, 2004.
Sui et al. Clinical significance of Skp2 expression, alone and combined with Jabl and p27 in epithelial ovarian tumors. Oncol. Rep., 15 (4):765-771, 2006.
Sum et al. Overexpression of LMO4 induces mammary hyperplasia, promotes cell invasion, and is a predictor of poor outcome in breast cancer. Proc Natl Aced Sci U S A, 102(21):7659- 7664, 2005.
Sum et al. The LIM domain protein LMO4 interacts with the cofactor CtIP and the tumor suppressor BRCA1 and inhibits BRCA1 activity. J Biol Chem, 277(10):7849-7856, 2002.
Sun et al. Development of a micro-array to detect human and mouse microRNAs and characterization of expression in human organs. Nucleic Acids Research, 32(22):e188, 2004.
Sun et al. Downregulation of CCND1 and CDK6 by miR-34a induces cell cycle arrest. FEBS Letters, 582:1564-1568, 2008.
Sunpaweravong et al. Epidermal growth factor receptor and cyclin D1 are independently amplified and overexpressed in esophageal squamous cell carcinoma. J Cancer Res Clin Oncol, 131(2):111-119, 2005.
Swanson et al. The prognosis of T3NO colon cancer is dependent on the number of lymph nodes examined. Ann. Surg. Oncol., 10(1):65-71, 2003.
Szafranska et al. A unique microRNA molecular signature for pancreatic carcinoma. AACR-Pancreatic Cancer: Early Detection and Novel Therapeutics, Chapel Hill, NC, Jun. 26- 27, 2006.
Szafranska et al. MicroRNA expression alterations are linked to tumorigenesis and non-neoplastic processes in pancreatic ductal adenocarcinoma. Oncogene, 26:4442-4452, 2007.
Tagawa et al. Genome-wide array-based CGH for mantle cell lymphoma: identification of homozygous deletions of the proapoptoic gene BIM. Oncogene, 24(8):1348-1358, 2005.
Takamizawa et al. Reduced expression of the let-7 microRNAs in human lung cancers in association with shortened postoperative survival. Cancer Research, 64:3753-3756, 2004.
Takanami. The prognostic value of overexpression of Skp2 mRNA in non-small cell lung cancer . Oncol. Rep., 13 (4):727-731, 2005.
Takei et al. A small interfering RNA targeting vascular endothelial growth factor as cancer therapeutics. Cancer Research, 64:3365-3370, 2004.
Takeshita et al. Efficient delivery of small interfering RNA to bone-metastatic tumors by using atelocollagen in vivo. PNAS, 102(34):12177-12182, 2005.
Takeshita et al. Systemic delivery of synthetic microRNA-16 inhibits the growth of metastatic prostate tumors via downregulation of multiple cell-cycle genes. Molecular Therapy, 18(1):181-187, 2010.
Takeuchi et al. Prognostic significance of molecular upstaging of paraffin-embedded sentinel lymph nodes in melanoma patients. J Clin. Oncol., 22:2671-2680, 2004.

(56) References Cited

OTHER PUBLICATIONS

Takimoto et al. Genetic alterations in the retinoblastoma protein-related p107 gene in human hematologic malignancies. Biochem Biophys Res Commun, 251(1):264-268, 1998.
Tanaka et al. A novel frizzled gene identified in human esophageal carcinoma mediates APC/beta-catenin signals. Proc. Natl. Acad. Sci. USA, 95 (17):10164-10169, 1998.
Tang et al. Prostate cancer stem/progenitor cells: identification, characterization, and implications. Mol. Carcinog., 46(1):1-14, 2007.
Tang et al. PS 7-2 microrna expression profile in cervical cancer and its derived cell lines. 23rd International Papillomavirus Conference and Clinical Workshop, Prague, Czech Republic, Sep. 1-7, 2006.
Tang et al. Transforming growth factor-beta can suppress tumorigenesis through effects on the putative cancer stem or early progenitor cell and committed progeny in a breast cancer xenograft model. Cancer Res., 67(18):8643-52, 2007.
Taniwaki et al. Gene expression profiles of small-cell lung cancers: molecular signatures of lung cancer. Int J Oncol, 29(3):567-575, 2006.
Tassi et al. Enhancement of fibroblast growth factor (FGF) activity by an FGF-binding protein. J. Biol. Chem., 276(43):40247-40253, 2001.
Tazawa et al. Tumor-suppressive miR-34a induces senescence-like growth arrest through modulation of the E2F pathway in human colon cancer cells. PNAS, 104(39):15472-15477, 2007.
Thiyagarajan et al. Role of GLI2 transcription factor in growth and tumorigenicity of prostate cells. Cancer Res., 67(22):10642-6, 2007.
Thogersen et al. A subclass of HER1 ligands are prognostic markers for survival in bladder cancer patients. Cancer Res., 61 (16):6227-6233, 2001.
Tijsterman and Plasterk. Dicers at RISC: the mechanism of RNAi. Cell, 117:1-4, 2004.
Tockman et al. Considerations in bringing a cancer biomarker to clinical application. Cancer Research, 52:2711s-2718s, 1992.
Toh et al. A novel candidate metastasis-associated gene, mta1, differentially expressed in highly metastatic mammary adenocarcinoma cell lines. cDNA cloning, expression, and protein analyses. J Biol Chem, 269(37):22958-22963, 1994.
Toh et al. Overexpression of metastasis-associated MTA1 mRNA in invasive oesophageal carcinomas. Br J Cancer, 79(11-12):1723-1726, 1999.
Toh et al. Overexpression of the MTA1 gene in gastrointestinal carcinomas: correlation with invasion and metastasis. Int J Cancer, 74(4):459-463, 1997.
Tomasini-Johansson et al. Vitronectin in colorectal adenocarcinoma—synthesis by stromal cells in culture. Exp. Cell. Res., 214 (1):303-312, 1994.
Torring et al. Increased expression of heparin binding EGF (HB-EGF), amphiregulin, TGF alpha and epiregulin in androgen-independent prostate cancer cell lines. Anticancer Res., 20 (1a):91-95, 2000.
Toyoda et al. Distribution of mRNA for human epiregulin, a differentially expressed member of the epidermal growth factor family. Biochem J, 326 (Pt 1):69-75, 1997.
Trang et al. Regression of marine lung tumors by the let-7 microRNA. Oncogene, 29(11):1580-1587, Epub 2009.
Traub et al. Prognostic impact of Skp2 and p27 in human breast cancer . Breast Cancer Res. Treat., 99 (2):185-191, 2006.
Tricoli et al. MicroRNA: potential for cancer detection, diagnosis, and prognosis. Cancer Res., 67(10):4553-4555, 2007.
Tsai et al. Correlation of intrinsic chemoresistance of non-small-cell lung cancer cell lines with HER-2/neu gene expression but not with ras gene mutations. J Natl Cancer Inst, 85(11):897-901, 1993.
Tsai et al. RIG1 inhibits the Ras/mitogen-activated protein kinase pathway by suppressing the activation of Ras . Cell Signal, 18 (3):349-358, 2006.
Turner et al. Hallmarks of 'BRCAness' in sporadic cancers. Nat Rev Cancer, 4(10):814-819, 2004.
Tuveson et al. BRAF as a potential therapeutic target in melanoma and other malignancies. Cancer Cell, 4(2):95-98, 2003.

Uhm et al. Vitronectin, a glioma-derived extracellular matrix protein, protects tumor cells from apoptotic death. Clin. Cancer Res., 5 (6):1587-1594, 1999.
Ulisse et al. Expression of Aurora kinases in human thyroid carcinoma cell lines and tissues. Int. J. Cancer, 119 (2): 275-282, 2006.
Upton et al. Expression of vimentin in surgically resected adenocarcinomas and large cell carcinomas of lung. Am J Surg Pathol, 10(8):560-567, 1986.
U.S. Appl. No. 10/778,908, entitled Anti-microRNA oligonucleotide molecules. Thomas Tuschl et al., filed Feb. 13, 2004.
U.S. Appl. No. 11/273,640, entitled Methods and compositions involving miRNA and miRNA inhibitors molecules. David Brown et al., filed Nov. 14, 2005.
U.S. Appl. No. 11/855,792, entitled Methods of normalization in microRNA detection assays. By Gary Latham et al., filed Sep. 14, 2007.
U.S. Appl. No. 11/857,948, entitled MicroRNAs differentially expressed in pancreatic diseases and uses thereof. Emmanuel Labourier et al., filed Sep. 19, 2007.
U.S. Appl. No. 11/967,639, entitled Functions and targets ofLET-7 micro RNAs. By Charles Johnson et al., filed Dec. 31, 2007.
U.S. Appl. No. 11/967,663, entitled miR-16 regulated genes and pathways as targets for therapeutic intervention. Mike Byrom et al., filed Dec. 31, 2007.
U.S. Appl. No. 12/112,291, entitled miR-20 Regulated Genes and Pathways as Targets for Therapeutic Intervention. Andreas Bader et al., filed Apr. 30, 2008.
U.S. Appl. No. 12/120,388, entitled miR-21 regulated genes and pathways as targets for therapeutic intervention. Andreas Bader et al., filed May 14, 2008.
U.S. Appl. No. 12/124,394, entitled miR-200 Regulated Genes and Pathways as Targets for Therapeutic Intervention. Andreas Bader et al., filed May 21, 2008.
U.S. Appl. No. 12/125,412, entitled miR-143 regulated genes and pathways as targets for therapeutic intervention. Andreas Bader et al., filed May 22, 2008.
U.S. Appl. No. 12/125,675, entitled miR-126 regulated genes and pathways as targets for therapeutic intervention. Andreas Bader et al., filed May 22, 2008.
U.S. Appl. No. 12/134,932, entitled miR-34 Regulated Genes and Pathways as Targets for Therapeutic Intervention. Andreas Bader et al., filed Jun. 6, 2008.
U.S. Appl. No. 12/167,492, entitled miR-15, miR-26, miR-31, miR-145, miR-147, miR-188, miR215, miR-216, miR-331, mmu-miR-292-3P regulated genes and pathways as targets for therapeutic intervention. Andreas Bader et al., filed Jul. 3, 2008.
U.S. Appl. No. 12/209,822, entitled MicroRNAs idfferentially expressed in cervical cancer and uses thereof. Sylvie Beaudenon et al., filed Sep. 12, 2008.
U.S. Appl. No. 12/253,718, entitled MicroRNAs differentially expressed in lung diseases and uses thereof. By Gary J. Lathan et al., filed Oct. 17, 2008.
U.S. Appl. No. 12/325,917, entitled miR-124 Regulated Genes and Pathways as Targets for Therapeutic Intervention. Andreas Bader et al., filed Dec. 1, 2008.
U.S. Appl. No. 12/340,329, entitled miR-10 Regulated Genes and Pathways as Targets for Therapeutic Intervention. Ovcharenko et al., filed Dec. 19, 2008.
U.S. Appl. No. 12/368,053, entitled miRNAs Differentially Expressed in Lymph Nodes from Cancer Patients. Sylvie Beaudenon et al., filed Feb. 9, 2009.
U.S. Appl. No. 12/398,852, entitled MicroRNA markers for recurrence of colorectal cancer. Elizabeth Mambo et al., filed Mar. 5, 2009.
U.S. Appl. No. 12/412,087, entitled Compositions and methods related to miR-16 and therapy of prostate cancer. Fumitaka Takeshita et al., filed Mar. 26, 2009.
U.S. Appl. No. 12/420,634, entitled Methods and compositions for diagnosing and modulating human papillomavirus (HPV). Sylvie Beaudenon-Huibregtse, filed Apr. 8, 2009.
U.S. Appl. No. 60/575,743, entitled Methods and compositions involving MicroRNA. David Brown et al., filed May 28, 2004.
U.S. Appl. No. 60/649,584, entitled Methods and compositions involving MicroRNA. David Brown et al., filed Feb. 3, 2005.

(56) References Cited

OTHER PUBLICATIONS

U.S. Appl. No. 60/650,807, entitled Compositions and methods involving MDA-7 and COX-2 inhibitors for the treatment of cancer. Sunil Chada et al., filed Feb. 8, 2005.
U.S. Appl. No. 60/906,028, entitled Prostate cancer specific miRNAs. David Brown, filed Mar. 9, 2007.
U.S. Appl. No. 61/113,385, entitled Methods and compositions involving miRNAs in cancer stem cells. Lubna Patrawala et al., filed Nov. 11, 2008.
U.S. Appl. No. 60/869,295 entitiled MicroRNAs Differentially Expressed in Leukemia and Uses Thereof. Tim Davison, et al., submitted Dec. 8, 2006.
Vanhaesebroeck et al. Phosphoinositide 3-kinases: a conserved family of signal transducers. Trends Biochem Sci, 22(7):267-272, 1997.
Vargas-Roig et al. Heat shock protein expression and drug resistance in breast cancer patients treated with induction chemotherapy. Cancer Detection and Prevention, 21(5):441-451, 1997.
Vella et al. Architecture of a validated microRNA::target interaction. Chem. Biol., 11(12):1619-1623, 2004.
Vella et al. The C. elegans microRNA let-7 binds to imperfect let-7 complementary sites from the lin-41 3'UTR. Genes Dev., 18(2):132-7, 2004.
Vermeulen et al. Single-cell cloning of colon cancer stem cells reveals a multi-lineage differentiation capacity. PNAS, 105(360):13427-13432, 2008.
Vezina & Bushman. Hedgehog signaling in prostate growth and benign prostate hyperplasia. Curr. Urol. Rep., 8(4):275-80, 2007.
Visvader et al. The LIM domain gene LMO4 inhibits differentiation of mammary epithelial cells in vitro and is overexpressed in breast cancer. Proc Natl Acad Sci USA. 98(25):14452-14457, 2001.
Visvanathan et al. The microRNA miR-124 antagonizes the anti-neural REST/SCP1 pathway during embryonic CNS development. Genes & Development, 21(7):744-749, 2007.
Vogt et al. Triple layer control: phosphorylation, acetylation and ubiquitination of FOXO proteins. Cell Cycle, 4(7):908-913, 2005.
Volinia et al. A microRNA expression signature of human solid tumors defines cancer gene targets. Proc. Natl. Acad. Sci. USA, 103(7):2257-2261, 2006.
Volloch and Sherman. Oncogenic potential of Hsp72. Oncogene, 18(24):3648-3651, 1999.
Voorhoeve et al. A genetic screen implicates miRNA-372 and miRNA-373 as oncogenes in testicular germ cell tumors. Cell, 124(6):1169-1181, 2006.
Vos et al. RASSF2 is a novel K-Ras-specific effector and potential tumor suppressor. J Biol Chem, 278(30):28045-28051, 2003.
Wade. Transcriptional control at regulatory checkpoints by histone deacetylases: molecular connections between cancer and chromatin. Hum. Mol. Genet., 10(7):693-698, 2001.
Wagner and Sondak. The sentinel lymph node: more than just another blue lymph node. Cancer, 97(8):1821-1823, 2003.
Walboomers et al. Human papillomavirus is a necessary cause of invasive cervical cancer worldwide, 1 Pathol. 189(1):12-9, 1999.
Wang & Dick. Cancer stem cells: lessons from leukemia, Trends Cell Biol., 15(9):494-501, 2005.
Wang and Wang. Systematic identification of microRNA functions by combining target prediction and expression profiling. Nucleic Acids Research, 34(5):1646-1652, 2006.
Wang et al. Aberrant expression of oncogenic and tumor-suppressive microRNAs in cervical cancer is required for cancer cell growth. PLoS One, 3(7):e2557, 2008.
Wang et al. Identification of rat lung-specific microRNAs by micoRNA microarray: valuable discoveries for the facilitation of lung research. BMC Genomics, 8:29-42, 2007.
Wang et al. Increased levels of forkhead box M1B transcription factor in transgenic mouse hepatocytes prevent age-related proliferation defects in regenerating liver. Proc Natl Aced Sci USA. 98(20):11468-11473, 2001.
Wang et al. Oncogenic HPV infection interrupts the expression of tumor-suppressive miR-34a through viral oncoprotein E6. RNA, 15(4):637-647, 2009.
Wang et al. Pten deletion leads to the expansion of a prostatic stem/progenitor cell subpopulation and tumor initiation. Proc. Natl. Acad. Sci. USA, 103(5):1480-1485, 2006.
Watabe et al. Growth, regeneration, and tumorigenesis of the prostate activates the PSCA promoter. Proc Natl Acad Sci USA, 99(1):401-6, 2002.
Weeraratna et al. Wnt5a signaling directly affects cell motility and invasion of metastatic melanoma. Cancer Cell, 1 (3):279-288, 2002.
Weidhaas et al. MicroRNAs as potential agents to alter resistance to cytotoxic anticancer therapy. Cancer Res, 67(23):11111-11116, 2007.
Weil et al. Targeting the kinesin Eg5 to monitor siRNA transfection in mammalian cells. Biotechniques, 33(6):1244-1248, 2002.
Weinstein. Disorders in cell circuitry during multistage carcinogenesis, the role of homeostasis. Carcinogenesis, 21 (5):857-864, 2000.
Weiss and Bohmann. Deregulated repression of c-Jun provides a potential link to its role in tumorigenesis. Cell Cycle, 3 (2):111-113, 2004.
Welsh et al. Fingerprinting genomes using PCR with arbitrary primers. Nucleic Acids Research, Oxford University Press, Surrey, GB, 18(24):7213-7218, 1990.
Welsh et al. Nucleic acid fingerprinting by PCR-based methods: applications to problems in aging and mutagenesis. Mutation Research, 338(1-6):215-229, 1995.
Wheeler and Ridley. Why three Rho proteins? RhoA, RhoB, RhoC, and cell motility. Exp. Cell. Res., 301 (1):43-49, 2004.
Whitcombe et al. A homogeneous fluorescence assay for PCR amplicons: its application to real-time, single-tube genotyping. Clin. Chem., 44(5):918-923, 1998.
Whitcombe et al. Advances in approaches to DNA-based diagnostics. Cum Opin. Biotechnol. 9(6):602-608, 1998.
White et al. Treatment of pulmonary hemangiomatosis with recombinant interferon alfa-2a. N Engl J Med 320:1197-1200, 1989.
Wiemer. The role of microRNAs in cancer: no small matter. Eur J Cancer, 43(10):1529-1544, 2007.
Wikman et al. Identification of differentially expressed genes in pulmonary adenocarcinoma by using cDNA array. Oncogene, 21(37):5804-5813, 2002.
Willert et al. Wnt proteins are lipid-modified and can act as stem cell growth factors. Nature, 423(6938):448-52, 2003.
Wilson and Laimins. Differentiation of HPV-containing cells using organotypic raft culture or methylcellulose. Methods Mol. Med., 119:157-69, 2005.
Wong et al., Clin Cancer Res 2008; 14(9):2588-2592.
Wong et al. Number of nodes examined and staging accuracy in colorectal carcinoma. J. Clin. Oncol. 17(9):2896-2900, 1999.
Wood et al. DNA microarray analysis of vitamin D-induced gene expression in a human colon carcinoma cell line. Physiol. Genomics, 17 (2):122-129, 2004.
Wood et al. One hundred consecutive cases of sentinel lymph node mapping in early colorectal carcinoma: detection of missed micrometastases. J Gastrointest Surg., 6(3):322-330, 2002.
Wooster and Weber. Breast and ovarian cancer. N. Engl. J Med., 348(23):2339-2347, 2003.
Wu et al. Expression of Ephb2 and Ephb4 in breast carcinoma. Pathol. Oncol. Res., 10 (1):26-33, 2004.
Wu et al. MicroRNA and cancer: current status and prospective. International Journal of Cancer, 120:953-960, 2006.
Wu et al. p107 Expression in colorectal tumours rises during carcinogenesis and falls during invasion. Eur J Cancer, 38(14):1838-1848, 2002.
Wu et al. RARRES1 expression is significantly related to tumour differentiation and staging in colorectal adenocarcinoma. Eur. J Cancer, 42(4):557-565, 2006.

(56) References Cited

OTHER PUBLICATIONS

Wu et al. RhoC induces differential expression of genes involved in invasion and metastasis in MCF10A breast cells. Breast Cancer Res., Treat. 84 (1):3-12, 2004.
Wu et al. The prognostic impact of EphB2/B4 expression on patients with advanced ovarian carcinoma. Gynecol. Oncol., 102 (1):15-21, 2006.
Wyatt et al. Synthesis and purification of large amounts of RNA oligonucleotides. Biotechniques, 11(6):764-769, 1991.
Wyttenbach et al. Polyglutamine expansions cause decreased CRE-mediated transcription and early gene expression changes prior to cell death in an inducible cell model of Huntington's disease. Human Molecular Genetics, 10(17):1829-1845, 2001.
Xi et al. A combination of molecular markers accurately detects lymph node metastasis in non-small cell lung cancer patients. Clin. Cancer Res., 12:2484-2491, 2006.
Xi et al. Differentially regulated micro-RNAs and actively translated messenger Rna transcripts by tumor suppressor p53 in colon cancer. Clin Cancer Res., 12:2014-2024, 2006b.
Xi et al. Identification of mRNA markers for molecular staging of lymph nodes in colorectal cancer. Clin. Chem., 52(3):520-523, 2006.
Xi et al. Molecular staging of lymph nodes from patients with esophageal adenocarcinoma. Clin. Cancer Res., 11:1099-1109, 2005.
Xi et al. Prognostic Values of microRNAs in Colorectal Cancer. Biomark Insights, 2:113-121, 2006a.
Xia et al. Positive expression of HIF-2alpha/EPAS1 in invasive bladder cancer. Urology, 59(5):774-778, 2002.
Xia et al. Regulation of vascular endothelial growth factor transcription by endothelial PAS domain protein 1 (EPAS1) and possible involvement of EPAS1 in the angiogenesis of renal cell carcinoma. Cancer, 91(8):1429-1436, 2001.
Xia et al. The Src-suppressed C kinase substrate, SSeCKS, is a potential metastasis inhibitor in prostate cancer. Cancer Res, 61(14):5644-5651, 2001.
Xie et al. Negative feedback regulation of Dicer-Like1 in Arabidopsis by microRNA-guided mRNA degradation. Current Biology, 13:784-789, 2003.
Xie, et al. Systematic discovery of regulatory motifs in human promoters and 3' UTRs by comparison of several mammals. Nature, 434(7031):338-345, 2005.
Xu et al. The *Drosophila* microRNA Mir-14 suppresses cell death and is required for normal fat metabolism. Curr. Biol., 13:790-795, 2003.
Yamamoto et al. Cdk2/cdc2 expression in colon carcinogenesis and effects of cdk2/cdc2 inhibitor in colon cancer cells. Int J Oncol, 13(2):233-239, 1998.
Yamato et al. New highly potent and specific E6 and E7 siRNAs for treatment of HPV16 positive cervical cancer. Cancer Gene Therapy, 15:140-153, 2008.
Yanaihara et al. Unique microRNA molecular profiles in lung cancer diagnosis and prognosis. Cancer Cell, 9:189-198, 2006.
Yang et al. Dicer is required for embryonic angiogenesis during mouse development. J Biol. Chem. 280(10):9330-9335, 2005.
Yang et al. Differential expression of CCAAT/enhancer-binding protein-delta (c/EBPdelta) in rat androgen-dependent tissues and human prostate cancer. J. Androl., 22 (3):471-480, 2001.
Yang et al. Significance of CD90+ cancer stem cells in human liver cancer. Cancer Cell, 13(2):153-66, 2008.
Yang et al. Smad3 reduces susceptibility to hepatocarcinoma by sensitizing hepatocytes to apoptosis through downregulation of Bc1-2. Cancer Cell, 9(6):445-457, 2006.
Yang et al. The transformation suppressor Pdcd4 is a novel eukaryotic translation initiation factor 4A binding protein that inhibits translation. Mol. Cell Biol., 23(1):26-37, 2003.
Yang et al. Stromel expression of connective tissue growth factor promotes angiogenesis and prostate cancer tumorigenesis. Cancer Res., 65(19):8887-8895, 2005.
Yang et al. Tumorigenesis suppressor Pdcd4 down-regulates mitogen-activated protein kinase kinase kinase kinase 1 expression to suppress colon carcinoma cell invasion. Mol Cell Biol, 26(4):1297-1306, 2006.
Yao et al. RhoC GTPase is required for PC-3 prostate cancer cell invasion but not motility. Oncogene, 25 (16):2285-2296, 2006.
Yeatman. A renaissance for SRC. Nat Rev Cancer, 4(6):470-480, 2004.
Yi et al. The association of the expression of MTA1, nm23H1 with the invasion, metastasis of ovarian carcinoma. Chin Med Sci J, 18(2):87-92, 2003.
Yoon and De Micheli. Prediction of regulatory modules comprising microRNAs and target genes. Bioinformatics, 21(Suppl.2):ii93-ii100, 2005.
Yoshida et al. The clinical significance of Cyclin B1 and Wee1 expression in non-small-cell lung cancer. Ann Oncol, 15(2):252-256, 2004.
Yoshimura et al. Prognostic impact of hypoxia-inducible factors 1 alpha and 2alpha in colorectal cancer patients: correlation with tumor angiogenesis and cyclooxygenase-2 expression. Clin. Cancer Res., 10(24):8554-8560, 2004.
Yoshioka et al. A role for LIM kinase in cancer invasion. Proc. Natl. Acad. Sci. USA, 100 (12):7247-7252, 2003.
Youssef et al. Hypermethylation and silencing of the putative tumor suppressor, Tazarotene-induced gene 1 in human cancers. Cancer Res., 64 (7):2411-2417, 2004.
Yu et al. Crosstalk between cancer and immune cells: role of STAT3 in the tumour microenvironment. Nat Rev Immunol, 7(1):41-51, 2007.
Yu et al,. Global assessment of promoter methylation in a mouse model of cancer identifies ID4 as a putative tumor-suppressor gene in human leukemia. Nat. Genet., 37 (3):265-274, 2005.
Yu et al. let-7 regulates self renewal and tumorigenicity of breast cancer cells. Cell, 131:1109-1123, 2007.
Zangemeister-Wittke and Huwiler. Antisense targeting of Mc1-1 has therapeutic potential in gastric cancer. Cancer Biol. Ther., 5(10):1355-1356, 2006.
Zeng et al. Both natural and designed micro RNAs can inhibit the expression of cognate mRNAs when expressed in human cells. Mol Cell. 9, 1327-33, 2002.
Zeng et al. MicroRNAs and small interfering RNAs can inhibit mRNA expression by similar mechanisms. Proc. Natl. Acad. Sci. 100:9779-9784, 2003.
Zhang et al. Enhancement of hematopoietic stem cell repopulating capacity and self-renewal in the absence of the transcription factor C/EBP alpha. Immunity, 21(6):853-863, 2004.
Zhang et al. Identification and characterization of ovarian cancer-initiating cells from primary human tumors. Cancer Res., 68(11):4311-20, 2008.
Zhang et al. Involvement of programmed cell death 4 in transforming growth factor-beta1-induced apoptosis in human hepatocellular carcinoma. Oncogene, 25(45):6101-6112, 2006.
Zhang et al. Methylation of the retinoid response gene TIG1 in prostate cancer correlates with methylation of the retinoic acid receptor beta gene. Oncogene, 23 (12):2241-2249, 2004.
Zhang et al. microRNAs as oncogenes and tumor suppressors. Dev. Biol., 302(1):1-12, 2007.
Zhang et al. NANOGP8 is a retrogene expressed in cancers. FEBS 1, 273(8):1723-30, 2006.
Zhao et al. Cyclin G1 has growth inhibitory activity linked to the ARF-Mdm2-p53 and pRb tumor suppressor pathways. Mol Cancer Res, 1(3):195-206, 2003.
Zhou et al. Activation of the PTEN/mTOR/STAT3 pathway in breast cancer stem-like cells is required for viability and maintenance. Proc. Natl. Acad. Sci. USA, 104(41):16158-63, 2007.
Zhou et al. The ABC transporter Bcrpl/ABCG2 is expressed in a wide variety of stem cells and is a molecular determinant of the side-population phenotype. Nat. Med. 7(9):1028-1034, 2001.
Zhu et al. Epiregulin is Up-regulated in pancreatic cancer and stimulates pancreatic cancer cell growth. Biochem. Biophys. Res. Commun., 273 (3):1019-1024, 2000.

(56) References Cited

OTHER PUBLICATIONS

Zhu et al. MicroRNA-21 targets the tumor suppressor gene tropomyosin 1 (TIPM1). The Journal of Biological Chemistry, 282(19):14328-14336, 2007.

Zimmerman et al. Technical aspects of quantitative competitive PCR. Biotechniques, 21(2):268-279, 1996.

Beg, et al. Presented at 26th EORTC-NCI-AACR Symposium on Molecular Targets and Cancer Therapeutics Barcelona, Spain on Nov. 19, 2015.

Hong, et al. Presented at 2015 Annual Meeting of American Association for Cancer Research held in Philadelphia, P on Apr. 21, 2015.

\* cited by examiner
† cited by third party

| | | |
|---|---|---|
| Pdgfb | 3'-uccguucaaccguauaaaucc-5' | (SEQ ID NO:122) |
| mmu-miR-31 | 5'-aggcaagaugcuggcauagcug-3' | (SEQ ID NO:123) |
| Hif1α | 3'-ccguucuccagccggucuuga-5' | (SEQ ID NO:124) |
| Frizzled4 | 3'-uccguucaccauacaccggaag-5' | (SEQ ID NO:125) |
| mmu-miR-31 | 5'-aggcaagaugcuggcauagcug-3' | (SEQ ID NO:126) |
| Vegf | 3'-ugaggguuguguucaggugucg-5' | (SEQ ID NO:127) |
| mmu-miR-150 | 5'-ucucccaacccuuguaccagug-3' | (SEQ ID NO:128) |
| Pdgfb | 3'-agaggguuccgagaucccgag-5' | (SEQ ID NO:129) |
| Notch4 | 3'-uuguaccggaguagguggucac-5' | (SEQ ID NO:130) |
| mmu-miR-150 | 5'-ucucccaacccuuguaccagug-3' | (SEQ ID NO:131) |
| Pdgfa | 3'-agaggguccguggaacugaac-5' | (SEQ ID NO:132) |
| Frizzled4 | 3'-uccgucguggugaauucccca-5' | (SEQ ID NO:133) |
| mmu-miR-184 | 5'-uggacggagaacugauaagggu-3' | (SEQ ID NO:134) |

SEQUENCE LISTING

```
<160> NUMBER OF SEQ ID NOS: 121

<210> SEQ ID NO 1
<211> LENGTH: 84
<212> TYPE: RNA
<213> ORGANISM: Homo sapiens

<400> SEQUENCE: 1
ccagucacgu ccccuuauca cuuuccagc ccagcuuugu gacuguaagu guuggacgga      60
gaacugauaa ggguaggugaa uuga                                           84

<210> SEQ ID NO 2
<211> LENGTH: 22
<212> TYPE: RNA
<213> ORGANISM: Homo sapiens

<400> SEQUENCE: 2
uggacggaga acugauaagg gu                                              22

<210> SEQ ID NO 3
<211> LENGTH: 71
```

```
<212> TYPE: RNA
<213> ORGANISM: Homo sapiens

<400> SEQUENCE: 3
ggagaggagg caagaugcug gcauagcugu ugaacuggga accugcuaug ccaacauauu    60
gccaucuuuc c                                                        71

<210> SEQ ID NO 4
<211> LENGTH: 21
<212> TYPE: RNA
<213> ORGANISM: Homo sapiens

<400> SEQUENCE: 4
aggcaagaug cuggcauagc u                                             21

<210> SEQ ID NO 5
<211> LENGTH: 84
<212> TYPE: RNA
<213> ORGANISM: Homo sapiens

<400> SEQUENCE: 5
cuccccaugg cccugucucc caacccuugu accagugcug ggcucagacc cugguacagg    60 ccuggggac agggaccugg ggac                                           84

<210> SEQ ID NO 6
<211> LENGTH: 22
<212> TYPE: RNA
<213> ORGANISM: Homo sapiens

<400> SEQUENCE: 6
ucucccaacc cuuguaccag ug                                            22

<210> SEQ ID NO 7
<211> LENGTH: 79
<212> TYPE: RNA
<213> ORGANISM: Homo sapiens

<400> SEQUENCE: 7
ugguacucgg ggagagguua cccgagcaac uuugcaucug gacgacgaau guugcucggu    60 gaacccuuu ucgguauca                                                 79

<210> SEQ ID NO 8
<211> LENGTH: 23
<212> TYPE: RNA
<213> ORGANISM: Homo sapiens

<400> SEQUENCE: 8 agguacccg agcaacuuug cau                                            23

<210> SEQ ID NO 9
<211> LENGTH: 64
<212> TYPE: RNA
<213> ORGANISM: Homo sapiens

<400> SEQUENCE: 9
ccccgcgacg agccccucgc acaaaccgga ccugagcguu uuguucguuc ggcucgcgug    60
aggc                                                                64

<210> SEQ ID NO 10
<211> LENGTH: 22
<212> TYPE: RNA
```

<213> ORGANISM: Homo sapiens

<400> SEQUENCE: 10
uuuguucguu cggcucgcgu ga                                        22

<210> SEQ ID NO 11
<211> LENGTH: 72
<212> TYPE: RNA
<213> ORGANISM: Homo sapiens

<400> SEQUENCE: 11
ggaucuuuuu gcggucuggg cuugcuguuc cucucaacag uagucaggaa gcccuuaccc    60
caaaaaguau cu                                                       72

<210> SEQ ID NO 12
<211> LENGTH: 21
<212> TYPE: RNA
<213> ORGANISM: Homo sapiens

<400> SEQUENCE: 12
cuuuuugcgg ucugggcuug c                                         21

<210> SEQ ID NO 13
<211> LENGTH: 91
<212> TYPE: RNA
<213> ORGANISM: Danio rerio

<400> SEQUENCE: 13
cguacagugc agucauccau aaaguagaaa gcacuacuaa accccucgcc acagguagu     60 guuccuacu uuauggauga guguacuguu g                                   91

<210> SEQ ID NO 14
<211> LENGTH: 21
<212> TYPE: RNA
<213> ORGANISM: Homo sapiens

<400> SEQUENCE: 14
cauaaaguag aaagcacuac u                                         21

<210> SEQ ID NO 15
<211> LENGTH: 64
<212> TYPE: RNA
<213> ORGANISM: Homo sapiens

<400> SEQUENCE: 15
augacugauu ucuuuuggug uucagaguca auauaauuuu cuagcaccau cugaaaucgg    60
uuau                                                                64

<210> SEQ ID NO 16
<211> LENGTH: 22
<212> TYPE: RNA
<213> ORGANISM: Homo sapiens

<400> SEQUENCE: 16
uagcaccauc ugaaaucggu ua                                        22

<210> SEQ ID NO 17
<211> LENGTH: 90
<212> TYPE: RNA
<213> ORGANISM: Homo sapiens

<400> SEQUENCE: 17

```
ugcccuucgc gaaucuuuuu gcggucuggg cuugcuguac auaacucaau agccggaagc    60
ccuuacccca aaaagcauuu gcggagggcg                                    90
```

<210> SEQ ID NO 18
<211> LENGTH: 21
<212> TYPE: RNA
<213> ORGANISM: Homo sapiens

<400> SEQUENCE: 18

```
cuuuuugcgg ucugggcuug c                                             21
```

<210> SEQ ID NO 19
<211> LENGTH: 110
<212> TYPE: RNA
<213> ORGANISM: Homo sapiens

<400> SEQUENCE: 19

```
ccagagguug uaacguuguc uauauauacc cuguagaacc gaauugugu gguauccgua    60 uagucacaga uucgauucua ggggaauaua uggucgaugc aaaaacuuca             110
```

<210> SEQ ID NO 20
<211> LENGTH: 23
<212> TYPE: RNA
<213> ORGANISM: Homo sapiens

<400> SEQUENCE: 20

```
uacccuguag aaccgaauuu gug                                           23
```

<210> SEQ ID NO 21
<211> LENGTH: 78
<212> TYPE: RNA
<213> ORGANISM: Homo sapiens

<400> SEQUENCE: 21

```
uggccgauuu uggcacuagc acauuuuugc uugugucucu ccgcucugag caaucaugug    60
cagugccaau augggaaa                                                 78
```

<210> SEQ ID NO 22
<211> LENGTH: 23
<212> TYPE: RNA
<213> ORGANISM: Homo sapiens

<400> SEQUENCE: 22

```
uuuggcacua gcacauuuuu gcu                                           23
```

<210> SEQ ID NO 23
<211> LENGTH: 110
<212> TYPE: RNA
<213> ORGANISM: Homo sapiens

<400> SEQUENCE: 23

```
ccgcagagug ugacuccugu ucuguguaug gcacugguag aauucacugu gaacagucuc    60
agucagugaa uuaccgaagg gccauaaaca gagcagagac agauccacga             110
```

<210> SEQ ID NO 24
<211> LENGTH: 22
<212> TYPE: RNA
<213> ORGANISM: Homo sapiens

<400> SEQUENCE: 24

```
uauggcacug guagaauuca cu                                              22

<210> SEQ ID NO 25
<211> LENGTH: 89
<212> TYPE: RNA
<213> ORGANISM: Homo sapiens

<400> SEQUENCE: 25
gucagcagug ccuuagcagc acguaaauau uggcguuaag auucuaaaau uaucuccagu     60
auuaacugug cugcugaagu aagguugac                                       89

<210> SEQ ID NO 26
<211> LENGTH: 22
<212> TYPE: RNA
<213> ORGANISM: Homo sapiens

<400> SEQUENCE: 26
uagcagcacg uaaauauugg cg                                              22

<210> SEQ ID NO 27
<211> LENGTH: 110
<212> TYPE: RNA
<213> ORGANISM: Homo sapiens

<400> SEQUENCE: 27
gagcugcuug ccuccccccg uuuuuggcaa ugguagaacu cacacuggug agguaacagg     60 auccggruggu ucuagacuug ccaacuaugg ggcgaggacu cagccggcac              110

<210> SEQ ID NO 28
<211> LENGTH: 24
<212> TYPE: RNA
<213> ORGANISM: Homo sapiens

<400> SEQUENCE: 28
uuuggcaaug guagaacuca cacu                                            24

<210> SEQ ID NO 29
<211> LENGTH: 92
<212> TYPE: RNA
<213> ORGANISM: Homo sapiens

<400> SEQUENCE: 29
cggcuggaca gcgggcaacg gaaucccaaa agcagcuguu gucuccagag cauuccagcu     60
gcgcuuggau uucgucccu gcucuccugc cu                                    92

<210> SEQ ID NO 30
<211> LENGTH: 23
<212> TYPE: RNA
<213> ORGANISM: Homo sapiens

<400> SEQUENCE: 30
caacggaauc ccaaaagcag cug                                             23

<210> SEQ ID NO 31
<211> LENGTH: 88
<212> TYPE: RNA
<213> ORGANISM: Homo sapiens

<400> SEQUENCE: 31
aucucuuaca caggcugacc gauuucuccu ggguucaga gucuguuuuu gucuagcacc      60
auuugaaauc gguuaugaug uaggggga                                        88
```

```
<210> SEQ ID NO 32
<211> LENGTH: 22
<212> TYPE: RNA
<213> ORGANISM: Homo sapiens

<400> SEQUENCE: 32
uagcaccauu ugaaaucggu ua                                              22

<210> SEQ ID NO 33
<211> LENGTH: 110
<212> TYPE: RNA
<213> ORGANISM: Homo sapiens

<400> SEQUENCE: 33
cggaaaauuu gccaaggguu uggggaaca uucaaccugu cggugaguuu gggcagcuca      60
ggcaaaccau cgaccguuga guggacccug aggccuggaa uugccauccu                110

<210> SEQ ID NO 34
<211> LENGTH: 22
<212> TYPE: RNA
<213> ORGANISM: Homo sapiens

<400> SEQUENCE: 34
aacauucaac cugucgguga gu                                              22

<210> SEQ ID NO 35
<211> LENGTH: 94
<212> TYPE: RNA
<213> ORGANISM: Homo sapiens

<400> SEQUENCE: 35 uguuugagc ggggucaag agcaauaacg aaaaauguuu gucauaaacc guuuuucauu       60
auugcuccug accuccucuc auuugcuaua uuca                                 94

<210> SEQ ID NO 36
<211> LENGTH: 23
<212> TYPE: RNA
<213> ORGANISM: Homo sapiens

<400> SEQUENCE: 36
ucaagagcaa uaacgaaaaa ugu                                             23

<210> SEQ ID NO 37
<211> LENGTH: 21
<212> TYPE: RNA
<213> ORGANISM: Homo sapiens

<400> SEQUENCE: 37
aaagugcacc caguuuuggg g                                               21

<210> SEQ ID NO 38
<211> LENGTH: 110
<212> TYPE: RNA
<213> ORGANISM: Homo sapiens

<400> SEQUENCE: 38
acccggcagu gccuccaggc gcagggcagc cccugcccac cgcacacugc gcugcccag      60 acccacugug cgugugacag cggcugaucu gugccugggc agcgcgaccc                110

<210> SEQ ID NO 39
```

```
<211> LENGTH: 22
<212> TYPE: RNA
<213> ORGANISM: Homo sapiens

<400> SEQUENCE: 39
cugugcgugu gacagcggcu ga                                               22

<210> SEQ ID NO 40
<211> LENGTH: 84
<212> TYPE: RNA
<213> ORGANISM: Homo sapiens

<400> SEQUENCE: 40
ucucagucug uggcacucag ccuugagggc acuuucuggu gccagaauga aagugcuguc      60
auagcugagg uccaaugacu gagg                                             84

<210> SEQ ID NO 41
<211> LENGTH: 23
<212> TYPE: RNA
<213> ORGANISM: Homo sapiens

<400> SEQUENCE: 41
cacucagccu ugagggcacu uuc                                              23

<210> SEQ ID NO 42
<211> LENGTH: 101
<212> TYPE: RNA
<213> ORGANISM: Homo sapiens

<400> SEQUENCE: 42
ccgcccccgc gucuccaggg caaccguggc uuucgauugu acuguggga acuggaggua       60 acagucuaca gccauggucg ccccgcagca cgcccacgcg c                         101

<210> SEQ ID NO 43
<211> LENGTH: 22
<212> TYPE: RNA
<213> ORGANISM: Homo sapiens

<400> SEQUENCE: 43
uaacagucua cagccauggu cg                                               22

<210> SEQ ID NO 44
<211> LENGTH: 84
<212> TYPE: RNA
<213> ORGANISM: Homo sapiens

<400> SEQUENCE: 44 gcuccccuc ucuaauccuu gcuaccuggg ugagagugcu gucugaaugc aaugcaccug       60
ggcaaggauu cugagagcga gagc                                             84

<210> SEQ ID NO 45
<211> LENGTH: 23
<212> TYPE: RNA
<213> ORGANISM: Homo sapiens

<400> SEQUENCE: 45
uaauccuugc uaccuggguc aga                                              23

<210> SEQ ID NO 46
<211> LENGTH: 94
<212> TYPE: RNA
<213> ORGANISM: Homo sapiens
```

<400> SEQUENCE: 46
cggggcggcc gcucucccug uccuccagga gcucacgugu gccugccugu gagcgccucg    60
acgacagagc cggcgccugc cccagugucu gcgc    94

<210> SEQ ID NO 47
<211> LENGTH: 23
<212> TYPE: RNA
<213> ORGANISM: Homo sapiens

<400> SEQUENCE: 47
ucccuguccu ccaggagcuc acg    23

<210> SEQ ID NO 48
<211> LENGTH: 87
<212> TYPE: RNA
<213> ORGANISM: Homo sapiens

<400> SEQUENCE: 48
caauagacac ccaucguguc uuuugcucug cagucaguaa auauuuuuuu gugaaugugu    60
agcaaaagac agaauggugg uccauug    87

<210> SEQ ID NO 49
<211> LENGTH: 21
<212> TYPE: RNA
<213> ORGANISM: Homo sapiens

<400> SEQUENCE: 49
gugucuuuug cucugcaguc a    21

<210> SEQ ID NO 50
<211> LENGTH: 77
<212> TYPE: RNA
<213> ORGANISM: Homo sapiens

<400> SEQUENCE: 50
ccgggaccca guucaaguaa uucaggauag guugugugcu guccagccug uucuccauua    60
cuuggcucgg ggaccgg    77

<210> SEQ ID NO 51
<211> LENGTH: 21
<212> TYPE: RNA
<213> ORGANISM: Homo sapiens

<400> SEQUENCE: 51
uucaaguaau ucaggauagg u    21

<210> SEQ ID NO 52
<211> LENGTH: 88
<212> TYPE: RNA
<213> ORGANISM: Homo sapiens

<400> SEQUENCE: 52
accaaguuuc aguucaugua aacauccuac acucagcugu aauacaugga uuggcuggga    60
gguggauguu uacuucagcu gacuugga    88

<210> SEQ ID NO 53
<211> LENGTH: 22
<212> TYPE: RNA
<213> ORGANISM: Homo sapiens

```
<400> SEQUENCE: 53
uguaaacauc cuacacucag cu                                              22

<210> SEQ ID NO 54
<211> LENGTH: 83
<212> TYPE: RNA
<213> ORGANISM: Homo sapiens

<400> SEQUENCE: 54
ccuuggagua aaguagcagc acauaauggu uuguggauuu ugaaaaggug caggccauau     60
ugugcugccu caaaaauaca agg                                            83

<210> SEQ ID NO 55
<211> LENGTH: 22
<212> TYPE: RNA
<213> ORGANISM: Homo sapiens

<400> SEQUENCE: 55
uagcagcaca uaaugguuug ug                                              22

<210> SEQ ID NO 56
<211> LENGTH: 72
<212> TYPE: RNA
<213> ORGANISM: Homo sapiens

<400> SEQUENCE: 56
cuugggaaug gcaaggaaac cguuaccauu acugaguuua guaaugguaa ugguucucuu     60
gcuauaccca ga                                                        72

<210> SEQ ID NO 57
<211> LENGTH: 22
<212> TYPE: RNA
<213> ORGANISM: Homo sapiens

<400> SEQUENCE: 57
aaaccguuac cauuacugag uu                                              22

<210> SEQ ID NO 58
<211> LENGTH: 98
<212> TYPE: RNA
<213> ORGANISM: Homo sapiens

<400> SEQUENCE: 58
cgagggauua cagcagcaau ucauguuuug aaguguucua aaugguucaa aacgugaggc     60
gcugcuauac ccccucgugg ggaagguaga aggugggg                            98

<210> SEQ ID NO 59
<211> LENGTH: 22
<212> TYPE: RNA
<213> ORGANISM: Homo sapiens

<400> SEQUENCE: 59
cagcagcaau ucauguuuug aa                                              22

<210> SEQ ID NO 60
<211> LENGTH: 99
<212> TYPE: RNA
<213> ORGANISM: Homo sapiens

<400> SEQUENCE: 60
ccgaugugua uccucagcuu ugagaacuga auuccauggg uugugucagu gucagaccuc     60
```
ugaaauucag uucuucagcu gggauaucuc ugucaucgu                  99

<210> SEQ ID NO 61
<211> LENGTH: 22
<212> TYPE: RNA
<213> ORGANISM: Homo sapiens

<400> SEQUENCE: 61
ugagaacuga auccaugggg uu                                    22

<210> SEQ ID NO 62
<211> LENGTH: 110
<212> TYPE: RNA
<213> ORGANISM: Homo sapiens

<400> SEQUENCE: 62
ggccuggcug dacagaguug ucaugugucu gccugucuac acuugcugug cagaacaucc   60
gcucaccugu acagcaggca cagacaggca gucacaugac aacccagccu              110

<210> SEQ ID NO 63
<211> LENGTH: 22
<212> TYPE: RNA
<213> ORGANISM: Homo sapiens

<400> SEQUENCE: 63
acagcaggca cagacaggca gu                                    22

<210> SEQ ID NO 64
<211> LENGTH: 71
<212> TYPE: RNA
<213> ORGANISM: Homo sapiens

<400> SEQUENCE: 64
gccaacccag uguucagacu accuguucag gaggcucuca auguguacag uagucugcac   60
auugguuagg c                                                71

<210> SEQ ID NO 65
<211> LENGTH: 23
<212> TYPE: RNA
<213> ORGANISM: Homo sapiens

<400> SEQUENCE: 65
cccaguguuc agacuaccug uuc                                   23

<210> SEQ ID NO 66
<211> LENGTH: 110
<212> TYPE: RNA
<213> ORGANISM: Homo sapiens

<400> SEQUENCE: 66
ugaguuuuga gguugcuuca gugaacauuc aacgcugucg gugaguuugg aauuaaaauc   60
aaaaccaucg accguugauu guacccuaug gcuaaccauc aucuacucca              110

<210> SEQ ID NO 67
<211> LENGTH: 23
<212> TYPE: RNA
<213> ORGANISM: Homo sapiens

<400> SEQUENCE: 67
aacauucaac gcugucgguG agu                                   23

```
<210> SEQ ID NO 68
<211> LENGTH: 99
<212> TYPE: RNA
<213> ORGANISM: Mus musculus

<400> SEQUENCE: 68
agaugccuug cccuacaag aguaaagugc augcgcuuug ggacagugag gaaaauaaug    60
uucacaaagc ccauacacuu ucacccuuua ggagaguug                          99

<210> SEQ ID NO 69
<211> LENGTH: 22
<212> TYPE: RNA
<213> ORGANISM: Mus musculus

<400> SEQUENCE: 69
uucacaaagc ccauacacuu uc                                            22

<210> SEQ ID NO 70
<211> LENGTH: 72
<212> TYPE: RNA
<213> ORGANISM: Homo sapiens

<400> SEQUENCE: 70 ugucgguag cuuaucagac ugauguugac uguugaaucu cauggcaaca ccagucgaug    60
ggcugucuga ca                                                       72

<210> SEQ ID NO 71
<211> LENGTH: 22
<212> TYPE: RNA
<213> ORGANISM: Homo sapiens

<400> SEQUENCE: 71
uagcuuauca gacugauguu ga                                            22

<210> SEQ ID NO 72
<211> LENGTH: 110
<212> TYPE: RNA
<213> ORGANISM: Homo sapiens

<400> SEQUENCE: 72
gugauaaugu agcgagauuu ucuguugugc uugaucuaac caugugguug cgagguauga    60
guaaaacaug guccgucaa gcaccaugga acgucacgca gcuuucuaca              110

<210> SEQ ID NO 73
<211> LENGTH: 21
<212> TYPE: RNA
<213> ORGANISM: Homo sapiens

<400> SEQUENCE: 73
uugugcuuga ucuaaccaug u                                             21

<210> SEQ ID NO 74
<211> LENGTH: 99
<212> TYPE: RNA
<213> ORGANISM: Homo sapiens

<400> SEQUENCE: 74
caagcacgau uagcauuuga ggugaaguuc uguuauacac ucaggcugug gcucucugaa    60
agucagugca ucacagaacu uugucucgaa agcuuucua                          99
```

```
<210> SEQ ID NO 75
<211> LENGTH: 22
<212> TYPE: RNA
<213> ORGANISM: Homo sapiens

<400> SEQUENCE: 75
ucagugcauc acagaacuuu gu                                              22

<210> SEQ ID NO 76
<211> LENGTH: 81
<212> TYPE: RNA
<213> ORGANISM: Homo sapiens

<400> SEQUENCE: 76
ccuuggccau guaaaagugc uuacagugca gguagcuuuu ugagaucuac ugcaauguaa     60
gcacuucuua cauuaccaug g                                               81

<210> SEQ ID NO 77
<211> LENGTH: 23
<212> TYPE: RNA
<213> ORGANISM: Homo sapiens

<400> SEQUENCE: 77
aaaagugcuu acagugcagg uag                                             23

<210> SEQ ID NO 78
<211> LENGTH: 110
<212> TYPE: RNA
<213> ORGANISM: Homo sapiens

<400> SEQUENCE: 78
aaagauccuc agacaaucca ugugcuucuc uuguccuuca uuccaccgga gucugucuca     60
uacccaacca gauuucagug gagugaaguu caggaggcau ggagcugaca              110

<210> SEQ ID NO 79
<211> LENGTH: 22
<212> TYPE: RNA
<213> ORGANISM: Homo sapiens

<400> SEQUENCE: 79
uccuucauuc caccggaguc ug                                              22

<210> SEQ ID NO 80
<211> LENGTH: 87
<212> TYPE: RNA
<213> ORGANISM: Homo sapiens

<400> SEQUENCE: 80
accgcaggga aaugaggga cuuuuggggg cagaugugu uccauccac uaucauaaug        60 ccccuaaaaa uccuuauugc ucuugca                                         87

<210> SEQ ID NO 81
<211> LENGTH: 22
<212> TYPE: RNA
<213> ORGANISM: Homo sapiens

<400> SEQUENCE: 81
uaaugccccu aaaaauccuu au                                              22

<210> SEQ ID NO 82
<211> LENGTH: 63
<212> TYPE: RNA
```

```
<213> ORGANISM: Homo sapiens

<400> SEQUENCE: 82
aagaaauggu uuaccguccc acauacauuu ugaauaugua ugugggaugg uaaaccgcuu    60
cuu                                                                  63

<210> SEQ ID NO 83
<211> LENGTH: 22
<212> TYPE: RNA
<213> ORGANISM: Homo sapiens

<400> SEQUENCE: 83
ugguuuaccg ucccacauac au                                             22

<210> SEQ ID NO 84
<211> LENGTH: 22
<212> TYPE: RNA
<213> ORGANISM: Homo sapiens

<400> SEQUENCE: 84
aauugcacgg uauccaucug ua                                             22

<210> SEQ ID NO 85
<211> LENGTH: 90
<212> TYPE: RNA
<213> ORGANISM: Homo sapiens

<400> SEQUENCE: 85
ccgggccccu gugagcaucu uaccggacag ugcuggauuu cccagcuuga cucuaacacu    60
gucugguaac gauguucaaa ggugacccgc                                     90

<210> SEQ ID NO 86
<211> LENGTH: 22
<212> TYPE: RNA
<213> ORGANISM: Homo sapiens

<400> SEQUENCE: 86
uaacacuguc ugguaacgau gu                                             22

<210> SEQ ID NO 87
<211> LENGTH: 99
<212> TYPE: RNA
<213> ORGANISM: Mus musculus

<400> SEQUENCE: 87
cauggcaccu ccguucccu gaggagcccu uugagccugg agugaaaaaa aaaaacaggu     60
caagaggcgc cugggaacug gagaagagug uuaaacuuc                           99

<210> SEQ ID NO 88
<211> LENGTH: 24
<212> TYPE: RNA
<213> ORGANISM: Mus musculus

<400> SEQUENCE: 88
ucccugagga gcccuuugag ccug                                           24

<210> SEQ ID NO 89
<211> LENGTH: 80
<212> TYPE: RNA
<213> ORGANISM: Homo sapiens

<400> SEQUENCE: 89
```
gguaccugaa gagagguuuu cuggguuucu guuucuuuaa ugaggacgaa acacaccugg    60
uuaaccucuu uuccaguauc                                                80

<210> SEQ ID NO 90
<211> LENGTH: 22
<212> TYPE: RNA
<213> ORGANISM: Homo sapiens

<400> SEQUENCE: 90
aacacaccug guuaaccucu uu                                             22

<210> SEQ ID NO 91
<211> LENGTH: 85
<212> TYPE: RNA
<213> ORGANISM: Macaca mulatta

<400> SEQUENCE: 91
ccuuagcaga gcugugagu gugacaaugg uguuuguguc uaaacuauca aacgccauua    60
ucacacuaaa uagcuacuac uaggc                                          85

<210> SEQ ID NO 92
<211> LENGTH: 22
<212> TYPE: RNA
<213> ORGANISM: Macaca mulatta

<400> SEQUENCE: 92
uggaguguga caauguguu ug                                              22

<210> SEQ ID NO 93
<211> LENGTH: 71
<212> TYPE: RNA
<213> ORGANISM: Homo sapiens

<400> SEQUENCE: 93
guagcacuaa agugcuuaua gugcaggguag uguuuaguua ucuacugcau uaugagcacu    60
uaaaguacug c                                                         71

<210> SEQ ID NO 94
<211> LENGTH: 23
<212> TYPE: RNA
<213> ORGANISM: Homo sapiens

<400> SEQUENCE: 94
uaaagugcuu auagugcagg uag                                            23

<210> SEQ ID NO 95
<211> LENGTH: 88
<212> TYPE: RNA
<213> ORGANISM: Homo sapiens

<400> SEQUENCE: 95
ucccaugcug ugacccucua gaggaagcac uuucuguuug uugucugaga aaaacaaag    60 ugcuucccuu uagaguuacu guuuggga                                       88

<210> SEQ ID NO 96
<211> LENGTH: 22
<212> TYPE: RNA
<213> ORGANISM: Homo sapiens

<400> SEQUENCE: 96

```
acaaagugcu ucccuuuaga gu                                              22

<210> SEQ ID NO 97
<211> LENGTH: 87
<212> TYPE: RNA
<213> ORGANISM: Homo sapiens

<400> SEQUENCE: 97
gacagugcag ucacccauaa aguagaaagc acuacuaaca gcacuggagg guguagoguu      60 uccuacuuua uggaugagug uacugug                                         87

<210> SEQ ID NO 98
<211> LENGTH: 21
<212> TYPE: RNA
<213> ORGANISM: Homo sapiens

<400> SEQUENCE: 98
cauaaaguag aaagcacuac u                                               21

<210> SEQ ID NO 99
<211> LENGTH: 110
<212> TYPE: RNA
<213> ORGANISM: Homo sapiens

<400> SEQUENCE: 99
guguugggga cucgcgcgcu ggguccagug guucuuaaca guucaacagu ucguagcgc       60 aauugugaaa uguuuaggac cacuagaccc ggcgggcgcg gcgacagcga                110

<210> SEQ ID NO 100
<211> LENGTH: 22
<212> TYPE: RNA
<213> ORGANISM: Homo sapiens

<400> SEQUENCE: 100
gugaaauguu uaggaccacu ag                                              22

<210> SEQ ID NO 101
<211> LENGTH: 110
<212> TYPE: RNA
<213> ORGANISM: Homo sapiens

<400> SEQUENCE: 101
ucaccuggcc augugacuug ugggcuuccc uuugucaucc uucgccuagg gcucugagca      60
gggcagggac agcaaagggg ugcucaguug ucacuuccca cagcacggag               110

<210> SEQ ID NO 102
<211> LENGTH: 22
<212> TYPE: RNA
<213> ORGANISM: Homo sapiens

<400> SEQUENCE: 102
uucccuuugu cauccuucgc cu                                              22

<210> SEQ ID NO 103
<211> LENGTH: 88
<212> TYPE: RNA
<213> ORGANISM: Homo sapiens

<400> SEQUENCE: 103
caccuugucc ucacggucca guuucccag gaaucccuua gaugcuaaga uggggauucc       60
uggaaauacu guucuugagg ucaugguu                                        88
```

-continued

```
<210> SEQ ID NO 104
<211> LENGTH: 23
<212> TYPE: RNA
<213> ORGANISM: Homo sapiens

<400> SEQUENCE: 104
guccaguuuu cccaggaauc ccu                                                23

<210> SEQ ID NO 105
<211> LENGTH: 83
<212> TYPE: RNA
<213> ORGANISM: Homo sapiens

<400> SEQUENCE: 105
cggggugagg uaguagguug ugugguuuca gggcagugau guugcccuc ggaagauaac         60 uauacaaccu acugccuucc cug                                                83

<210> SEQ ID NO 106
<211> LENGTH: 22
<212> TYPE: RNA
<213> ORGANISM: Homo sapiens

<400> SEQUENCE: 106
ugagguagua gguugugugg uu                                                 22

<210> SEQ ID NO 107
<211> LENGTH: 80
<212> TYPE: RNA
<213> ORGANISM: Homo sapiens

<400> SEQUENCE: 107
cugggggcuc caaagugcug uucgugcagg uagugugauu acccaaccua cugcugagcu        60
agcacuuccc gagccccgg                                                     80

<210> SEQ ID NO 108
<211> LENGTH: 23
<212> TYPE: RNA
<213> ORGANISM: Homo sapiens

<400> SEQUENCE: 108
caaagugcug uucgugcagg uag                                                23

<210> SEQ ID NO 109
<211> LENGTH: 110
<212> TYPE: RNA
<213> ORGANISM: Homo sapiens

<400> SEQUENCE: 109
gccgagaccg agugcacagg gcucugaccu augaauugac agccagugcu cucgucuccc        60
cucuggcugc caauuccaua ggucacaggu auguucgccu caaugccagc                  110

<210> SEQ ID NO 110
<211> LENGTH: 21
<212> TYPE: RNA
<213> ORGANISM: Homo sapiens

<400> SEQUENCE: 110
cugaccuaug aauugacagc c                                                  21

<210> SEQ ID NO 111
```

```
<211> LENGTH: 83
<212> TYPE: RNA
<213> ORGANISM: Homo sapiens

<400> SEQUENCE: 111
cgccggccga ugggcgucuu accagacaug guuagaccug gcccucuguc uaauacuguc     60
ugguaaaacc guccauccgc ugc                                             83

<210> SEQ ID NO 112
<211> LENGTH: 22
<212> TYPE: RNA
<213> ORGANISM: Homo sapiens

<400> SEQUENCE: 112
uaauacuguc ugguaaaacc gu                                              22

<210> SEQ ID NO 113
<211> LENGTH: 71
<212> TYPE: RNA
<213> ORGANISM: Homo sapiens

<400> SEQUENCE: 113
uguucuaagg ugcaucuagu gcagauagug aaguagauua gcaucuacug cccuaagugc     60
uccuucuggc a                                                          71

<210> SEQ ID NO 114
<211> LENGTH: 23
<212> TYPE: RNA
<213> ORGANISM: Homo sapiens

<400> SEQUENCE: 114
uaaggugcau cuagugcaga uag                                             23

<210> SEQ ID NO 115
<211> LENGTH: 84
<212> TYPE: RNA
<213> ORGANISM: Rattus norvegicus

<400> SEQUENCE: 115
gucaggauaa ugucaaagug cuuacagugc agguaguggu gugugcaucu acugcaguga     60
aggcacuugu ggcauugugc ugac                                            84

<210> SEQ ID NO 116
<211> LENGTH: 23
<212> TYPE: RNA
<213> ORGANISM: Rattus norvegicus

<400> SEQUENCE: 116
caaagugcuu acagugcagg uag                                             23

<210> SEQ ID NO 117
<211> LENGTH: 22
<212> TYPE: RNA
<213> ORGANISM: Homo sapiens

<400> SEQUENCE: 117
acaagucagg cucuugggac cu                                              22

<210> SEQ ID NO 118
<211> LENGTH: 82
<212> TYPE: RNA
<213> ORGANISM: Homo sapiens
```

```
<400> SEQUENCE: 118
ccugccgggg cuaaagugcu gacagugcag auaguggucc ucuccgugcu accgcacugu    60
ggguacuugc ugcuccagca gg                                             82

<210> SEQ ID NO 119
<211> LENGTH: 21
<212> TYPE: RNA
<213> ORGANISM: Homo sapiens

<400> SEQUENCE: 119
uaaagugcug acagugcaga u                                              21

<210> SEQ ID NO 120
<211> LENGTH: 110
<212> TYPE: RNA
<213> ORGANISM: Homo sapiens

<400> SEQUENCE: 120
ccuggccucc ugcagugcca cgcuccgugu auuugacaag cugaguugga cacuccaugu    60
gguagagugu caguuuguca aauacaaa gugcggcaca ugcuuaccag                110

<210> SEQ ID NO 121
<211> LENGTH: 22
<212> TYPE: RNA
<213> ORGANISM: Homo sapiens

<400> SEQUENCE: 121
ugucaguuug ucaaauaccc ca                                             22
```

COMPOSITIONS AND METHODS RELATED TO MIRNA MODULATION OF NEOVASCULARIZATION OR ANGIOGENESIS

RELATED APPLICATIONS

This application is a continuation of U.S. application Ser. No. 13/602,933, filed Sep. 4, 2012, which is divisional of U.S. application Ser. No. 12/437,899, filed May 8, 2009, now issued as U.S. Pat. No. 8,258,111 on Sep. 4, 2012, which claims priority to U.S. Provisional Application Ser. No. 61/051,519, filed May 8, 2008, all of which are incorporated herein by reference in their entireties.

SEQUENCE LISTING

The present application contains a Sequence Listing which has been submitted in ASCII format via EFS-Web and is hereby incorporated by reference in its entirety. Said ASCII copy, created Jul. 13, 2015, is named "48436716301.txt" and is 23,028 bytes in size.

BACKGROUND OF THE INVENTION

I. Field of the Invention

The present invention relates generally to the fields of molecular biology and medicine. More particularly, it concerns methods and compositions involving microRNA (miR-NAs) molecules and disease treatment. Certain aspects of the invention include applications of miRNA therapy for diseases or conditions that involve neovascularization and/or angiogenesis.

II. Background

Pathologic neovascularization refers to the proliferation of blood vessels in tissue not normally containing them, or proliferation of blood vessels of a different kind than usual in a tissue. It includes angiogenesis in tumor growth, diabetic retinopathy, haemangiomas, arthritis, and psoriasis to name a few.

Angiogenesis is the process of forming new blood vessels from pre-existing capillaries. Angiogenesis is tightly regulated and normally does not occur except during development, wound healing, and the formation of the corpus luteum during the female reproductive cycle. This strict regulation is manifested by a balanced production of positive and negative factors, which keep angiogenesis in check. However, this balance becomes abrogated under various pathological conditions, such as cancer, diabetes, and age-related macular degeneration (AMD), resulting in the growth of new blood vessels. It is now well accepted that the progressive growth and metastasis of many solid tumors and loss of vision with diabetes are dependent on the growth of new blood vessels.

Vascular diseases of the eye and tumors of the central nervous system, such as retinoblastoma and primitive neuroectodermal tumors (PNETs), have significant neovascular components. Some tumors of the central nervous system and ocular vascular diseases share similar pathogenesis having a choroidal neovascularization and/or retinal neovascularization component.

Vascular diseases of the eye comprise a major cause of blindness. These diseases include various retinopathies and macular degeneration. Existing treatments include laser ablation of various regions of the retina; vitrectomy or removal of the cloudy vitreous humor and its replacement with a saline solution; and administration of antioxidant vitamins E and C, but none of these methods can cure the disease. Further, existing invasive treatment methods often result in significant loss of vision. Non-invasive methods of treatment are experimental and have not been shown to substantially reduce the risk of blindness or loss of sight.

There is a need for additional compositions and/or methods for treatment of diseases associated with neovascularization and angiogenesis.

SUMMARY OF THE INVENTION

The present invention provides additional diagnostic, prognostic, and/or therapeutic methods by identifying miRNAs that are differentially expressed or mis-regulated in various states of diseased, normal, cancerous, and/or abnormal tissues, including but not limited to diseases characterized by or associated with vascularization and angiogenesis that result in a pathological condition or disease.

A physician may choose to treat a condition associated with neovascularization and/or angiogenesis by surgery, chemotherapy, radiation therapy, immunotherapy, monoclonal antibody therapy and/or other methods. The choice of therapy depends upon the location and severity of the disease, as well as the general state of the patient. Certain aspects of the invention include methods for reducing vascularization in a subject or tissue comprising administering to the subject or tissue in need of such a reduction, in an amount sufficient to reduce vascularization and/or result in a beneficial response, one or more nucleic acid molecule comprising (a) a nucleic acid sequence that is at least 80%, 85%, 90%, 95%, 96%, 97%, 98%, 99% or 100% identical to one or more miR-184, miR-31, miR-150, miR-409, miR-375, miR-129-5p, miR-142a, miR-29a, miR-129-3p, miR-10b, miR-96, miR-183, miR-16, miR-182, miR-191, miR-29c, miR-181c, miR-335, miR-7026, miR-210, miR-512-3p, miR-132, miR-500, miR-339, miR-511, miR-26b, miR-30b, or miR-15a, or complement thereof; and/or (b) an inhibitor of miR-451, miR-424, miR-146, miR-214, miR-199a, miR-181, miR-350, miR-21, miR-218, miR-148b, miR-106a, miR-205, miR-365, miR-299-5p, ambi-miR-7079, miR-200a, miR-351, miR-329, miR-122a, miR-20a, miR-520 h, miR-142-5p, miR-203, miR-211, miR-145, let-7b, miR-93, miR-192, miR-201, miR-18a, miR-17-5p, miR-7085, miR-106b, or miR-223. In certain aspects, a nucleic acid is administered topically, enterally, parenterally or intravitreally. In a further aspect, the nucleic acid molecule is an RNA, DNA, or comprises all or portions of nucleotide analogs or mimetics. An RNA can comprise a complementary RNA region, such as, but not limited to a hairpin structure or multiple (e.g., two) RNA strands. The RNA or DNA molecule can include a nucleotide analog or a modified nucleotide. In still a further aspect, the nucleic acid molecule or miRNA inhibitor is a DNA molecule or is produced from a DNA molecule. An miRNA inhibitor can be an antisense oligonucleotide. The oligonucleotide can comprise all or a portion of nucleotide analogs. In other aspects the DNA is comprised in an expression cassette, such as a plasmid expression vector or a viral expression vector. The nucleic acid molecule can also be comprised in a lipid or viral delivery vehicle.

In certain aspects the subject has, is at risk of developing, or is suspected of having ocular or retinal/choroidal neovascular diseases, cancer, diabetic nephropathy, rheumatoid arthritis, atherosclerotic plaques, endometriosis, Crohn's disease, uterine fibroids, benign prostatic hyperplasia, or psoriasis. The nucleic acids or nucleic acid analogs disclosed herein are useful for treating and/or preventing a variety of angiogenic, microvascular, and macular disorders including macular degeneration (such as wet or neovascular age-related macular degeneration (AMD) and dry or atrophic AMD), macular edema, and secondary indications for inhibiting tumor vascularization, and corneal and iris neovascularization, for example.

A further aspect of the invention includes methods of stimulating vascularization in a subject or tissue comprising administering to a subject in need of such stimulation, in an amount sufficient to stimulate vascularization, one or more nucleic acid molecule comprising (a) a miRNA sequence that is at least 80%, 85%, 90%, 95%, 96%, 97%, 98%, 99% or 100% identical to one or more of miR-451, miR-424, miR-146, miR-214, miR-199a, miR-181, miR-350, miR-21, miR-218, miR-148b, miR-106a, miR-205, miR-365, miR-299-5p, ambi-miR-7079, miR-200a, miR-351, miR-329, miR-122a, miR-20a, miR-520 h, miR-142-5p, miR-203, miR-211, miR-145, let-7b, miR-93, miR-192, miR-201, miR-18a, miR-17-5p, miR-7085, miR-106b, and/or miR-223; and/or (b) an inhibitor of miR-184, miR-31, miR-150, miR-409, miR-375, miR-129-5p, miR-142a, miR-29a, miR-129-3p, miR-10b, miR-96, miR-183, miR-16, miR-182, miR-191, miR-29c, miR-181c, miR-335, miR-7026, miR-210, miR-512-3p, miR-132, miR-500, miR-339, miR-511, miR-26b, miR-30b, and/or miR-15a. In further aspects of the invention the subject has, is at risk of developing, or is suspected of having coronary artery disease (CAD), cardiac failure, tissue injury, or ischemia.

In yet another aspect the invention includes methods for selecting a vascular therapy for a patient comprising (a) measuring an expression profile of one or more of miR-184, miR-31, miR-150, miR-409, miR-375, miR-129-5p, miR-142a, miR-29a, miR-129-3p, miR-10b, miR-96, miR-183, miR-16, miR-182, miR-191, miR-29c, miR-181c, miR-335, miR-7026, miR-210, miR-512-3p, miR-132, miR-500, miR-339, miR-511, miR-26b, miR-30b, miR-15a, miR-451, miR-424, miR-146, miR-214, miR-199a, miR-181, miR-350, miR-21, miR-218, miR-148b, miR-106a, miR-205, miR-365, miR-299-5p, ambi-miR-7079, miR-200a, miR-351, miR-329, miR-122a, miR-20a, miR-520 h, miR-142-5p, miR-203, miR-211, miR-145, let-7b, miR-93, miR-192, miR-201, miR-18a, miR-17-5p, miR-7085, miR-106b, and/or miR-223 in a sample; and (b) selecting a therapy based on a comparison of the miRNA expression profile in the patient sample to an expression profile of a normal or non-pathogenic sample, wherein a difference between the expression profiles is indicative of a pathological condition. The altered expression for any of the miRNAs indicates that the patient should be treated with a corresponding therapeutic directed toward the altered miRNA or condition indicated by such altered miRNA.

In some embodiments, it may be useful to know whether a cell expresses a particular miRNA endogenously or whether such expression is affected under particular conditions or when it is in a particular disease state. Thus, in some embodiments of the invention, methods include assaying a cell or a sample containing a cell for the presence of one or more miRNA. Consequently, in some embodiments, methods include a step of generating a miRNA profile for a sample. The term "miRNA profile" refers to data regarding the expression pattern of miRNAs in the sample (e.g., one or more miRNA described herein). It is contemplated that the miRNA profile can be obtained using a set of miRNAs, using for example nucleic acid amplification or hybridization techniques well known to one of ordinary skill in the art. In certain embodiments, expression of one or more miRNA described herein is evaluated.

In some embodiments of the invention, an miRNA profile is generated by steps that include one or more of: (a) labeling miRNA in the sample; (b) hybridizing miRNA to a number of probes, or amplifying a number of miRNAs, and/or (c) determining miRNA hybridization to the probes or detecting miRNA amplification products, wherein miRNA expression levels are determined or evaluated. See U.S. Provisional Patent Applications 60/575,743 and 60/649,584, and U.S. patent application Ser. Nos. 11/141,707 and 11/855,792, all of which are hereby incorporated by reference.

Methods of the invention include determining a diagnosis or prognosis for a patient based on miRNA expression or expression levels. In certain embodiments, the elevation or reduction in the level of expression of a particular miRNA or set of miRNAs in a cell is correlated with a disease state as compared to the expression level of that miRNA or set of miRNAs in a normal cell or a reference sample or digital reference. This correlation allows for diagnostic methods to be carried out when the expression level of a miRNA is measured in a biological sample being assessed.

In certain embodiments a method for evaluating a patient includes the steps of determining expression levels of one or more of miR-451, miR-424, miR-146, miR-214, miR-199a, miR-181, miR-350, miR-21, miR-218, miR-148b, miR-106a, miR-205, miR-365, miR-299-5p, ambi-miR-7079, miR-200a, miR-351, miR-329, miR-122a, miR-20a, miR-520 h, miR-142-5p, miR-203, miR-211, miR-145, let-7b, miR-93, miR-192, miR-201, miR-18a, miR-17-5p, miR-7085, miR-106b, miR-223, miR-184, miR-31, miR-150, miR-409, miR-375, miR-129-5p, miR-142a, miR-29a, miR-129-3p, miR-10b, miR-96, miR-183, miR-16, miR-182, miR-191, miR-29c, miR-181c, miR-335, miR-7026, miR-210, miR-512-3p, miR-132, miR-500, miR-339, miR-511, miR-26b, miR-30b, and/or miR-15a in a biological sample comprising a portion of a tissue or fluid associated with a condition associated with aberrant vascularization, and/or determining a diagnosis or prognosis for the aberrant vascularization condition based on the miRNA expression levels. In a further aspect of the invention, a patient is suspected of having a condition associated with aberrant vascularization. Determining a diagnosis includes, but is not limited to screening for a pathological condition, staging a pathological condition, or assessing response of a pathological condition to therapy. In certain aspects, determining a diagnosis is determining if the patient has a condition associated with aberrant neovascularization or aberrant angiogenesis.

Methods can further comprise normalizing the expression levels of miRNA. Normalizing includes, but is not limited to adjusting expression levels of miRNA relative to expression levels of one or more nucleic acid in the sample.

It is specifically contemplated that miRNA profiles for patients, particularly those suspected of having or at risk of developing a particular disease or condition associated or related to vascularization and/or angiogenesis, can be generated by evaluating any miR or set of miRs discussed in this application. The miRNA profile that is generated from the patient will be one that provides information regarding the particular disease or condition. In certain aspects, a party evaluating miR expression may prepare a recommendation, report and/or summary conveying processed or raw data to a diagnosing physician. In certain aspects, a miRNA profile can be used in conjunction with other diagnostic tests.

Embodiments of the invention include methods for diagnosing, assessing a condition, and/or prognosing a disease or condition associated with or having an accompanying aberrant vascularization in a patient comprising evaluating or determining the expression or expression levels of one or more miRNAs in a sample from the patient. The difference in the expression in the sample from the patient and a reference, such as expression in a normal or non-pathologic sample, is indicative of a pathologic or diseased condition associated with neovascularization and/or angiogenesis. In certain aspects the miRNA expression level is compared to the expression level of a normal cell or a reference sample or a digital reference. Comparing miRNA expression levels includes comparing miRNA expression levels in a sample to miRNA expression levels in a normal tissue sample or reference tissue sample. A normal tissue sample can be taken from the patient being evaluated and can be a normal adjacent tissue to the area being assessed or evaluated.

In certain embodiments the expression of the miRNA is determined by an amplification assay or a hybridization assay. An amplification assay is a quantitative amplification assay, such as, but not limited to quantitative RT-PCR. Hybridization assays include, but are not limited to an array hybridization assay or a solution hybridization assay. An miRNA, amplification product, or probe set can comprise a segment of or be complementary to a corresponding miRNA including all or part of an miRNA sequence described herein. In certain aspects of the invention, a segment can comprise at least or about 5, 6, 7, 8, 9, 10, 11, 12 or more nucleic acid sequences of a miRNA. Other amplification or hybridization sequences may also be included for normalization purposes. The use of an miRNA quantification assay as a clinically relevant diagnostic tool can be enhanced by using an appropriate normalization control. The methods of normalization correct for sample-to-sample variability by comparing a target measurement in a sample to one or more internal controls. Normalization of miRNA quantification assays reduces systematic (non-biological) and non-systematic differences between samples, and can enhance the accurate measurement of differential miRNA expression, for example. The accurate measurement of biologically hardwired differential expression between two groups of samples is the goal of many miRNA qRT-PCR assays. Yet, miRNA levels in qRT-PCR reactions can vary from one sample to the next for reasons that may be technical or biological. Technical reasons may include variability in tissue procurement or storage, inconsistencies in RNA extraction or quantification, or differences in the efficiency of the reverse transcription and/or PCR steps. Biological reasons may include sample-to-sample heterogeneity in cellular populations, differences in bulk transcriptional activity, or alterations in specific miRNA expression that is linked to an aberrant biological program (e.g., a disease state). Given the multiplicity of sources that can contribute to differences in miRNA quantification, results from qRT-PCR assays can be normalized against a relevant endogenous target or targets to minimize controllable variation, and permit definitive interpretations of nominal differences in miRNA expression.

Because conditions related to neovascularization and/or angiogenesis, such as cancer, refer to a class of diseases, it is unlikely that there will be a single treatment and aspects of the invention can be used to determine which treatment will be most effective or most harmful and provide a guide for the physician in evaluating, assessing, and formulating a treatment strategy for a patient. A sample may be taken from a patient having or suspected of having a disease or pathological condition. In certain aspects, the sample can be, but is not limited to tissue (e.g., biopsy, particularly fine needle biopsy), sputum, lavage fluid, blood, serum, plasma, lymph node or other tissue or fluid that may contain cells associated with a neovascular or angiogenic condition. The sample can be fresh, frozen, fixed (e.g., formalin fixed), or embedded (e.g., paraffin embedded).

The methods can further comprise or exclude one or more steps including: (a) obtaining a sample from the patient, (b) isolating or obtaining nucleic acids from the sample, (c) reverse transcribing nucleic acids from the sample, (d) labeling the nucleic acids isolated from the sample or an amplification product thereof, (e) hybridizing the labeled nucleic acids to one or more probes or detecting the amplified nucleic acids, (f) analyzing and normalizing data by statistical methods, and/or (g) creating and/or supplying a report of the analysis. Nucleic acids of the invention may include one or more nucleic acids comprising at least one segment having a sequence or complementary sequence of one or more miRNA described herein. In certain aspects, the nucleic acids identify one or more miRNA described herein. Nucleic acids of the invention may be coupled to a support. Such supports are well known to those of ordinary skill in the art and include, but are not limited to glass, plastic, metal, or latex. In particular aspects of the invention, the support can be planar or in the form of a bead or other geometric shapes or configurations.

Embodiments of the invention include kits for analysis of a pathological sample by assessing a miRNA profile for a sample comprising, in suitable container means, one or more miRNA probes and/or amplification primers, wherein the miRNA probes detect or primer amplify one or more miRNA described herein. In certain embodiments the kit contains two or more miRNA hybridization or amplification reagents comprising one or more probe or amplification primer for one or more miRNA selected from miR-451, miR-424, miR-146, miR-214, miR-199a, miR-181, miR-350, miR-21, miR-218, miR-148b, miR-106a, miR-205, miR-365, miR-299-5p, ambi-miR-7079, miR-200a, miR-351, miR-329, miR-122a, miR-20a, miR-520 h, miR-142-5p, miR-203, miR-211, miR-145, let-7b, miR-93, miR-192, miR-201, miR-18a, miR-17-5p, miR-7085, miR-106b, miR-223, miR-184, miR-31, miR-150, miR-409, miR-375, miR-129-5p, miR-142a, miR-29a, miR-129-3p, miR-10b, miR-96, miR-183, miR-16, miR-182, miR-191, miR-29c, miR-181c, miR-335, miR-7026, miR-210, miR-512-3p, miR-132, miR-500, miR-339, miR-511, miR-26b, miR-30b, and/or miR-15a. The kit can further comprise reagents for labeling miRNA in the sample. The kit may also include labeling reagents comprising at least one amine-modified nucleotide, poly(A) polymerase, and poly(A) polymerase buffer. Labeling reagents can include an amine-reactive dye.

The present invention also concerns kits containing compositions of the invention or compositions to implement methods of the invention. In some embodiments, kits can be used to evaluate one or more miRNA molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more miRNA probes, synthetic miRNA molecules or miRNA inhibitors, or any range and combination derivable therein. In some embodiments, there are kits for evaluating miRNA activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more, including all values and ranges there between.

Kits for using miRNA probes, synthetic miRNAs, nonsynthetic, and/or miRNA inhibitors of the invention for therapeutic, prognostic, or diagnostic applications are included as part of the invention.

The term "miRNA" or "miR" is used according to its ordinary and plain meaning and refers to a microRNA molecule found in eukaryotes that is involved in RNA-based gene regulation. See, e.g., Carrington et al., 2003, which is hereby incorporated by reference. The term will be used to refer to the single-stranded RNA molecule processed from a precursor. Names of miRNAs and their sequences related to the present invention are provided herein.

Corresponding miRNA sequences that can be used in the context of the invention include, but are not limited to, all or a portion of those sequences in the sequence listing provided herein, as well as the miRNA precursor sequence, or complement of one or more of these miRNAs.

Any embodiment of the invention involving specific miRNAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA. In other aspects, miRNA of the invention may include additional nucleotides at the 5', 3', or both 5' and 3' ends of at least, at most or about 1, 2, 3, 4, 5, 6, 7, 8, 9, 10 or more nucleotides.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs. Typically, the synthetic miRNA is exposed to the proper conditions to allow it to become or function, at least in part, as a mature miRNA under physiological circumstances.

The claims originally filed are contemplated to cover claims that are multiply dependent on any filed claim or combination of filed claims.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Any embodiment discussed with respect to a particular condition can be applied or implemented with respect to a different condition. Furthermore, compositions and kits of the invention can be used to achieve methods of the invention.

Throughout this application, the term "about" may be used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Putative binding regions for mmu-miR-31, -150, and -184 in 3'-untranslated regions (UTRs) of predicted target mRNAs.

(FIG. 4A) VEGF levels in homogenates of experimental miRNA-treated and control miRNA-treated retinas, measured by ELISA. Each bar represents the mean VEGF level (±standard error of mean) calculated from three separate experiments. Asterisks indicate levels of VEGF significantly different from control-treated retinas. (FIG. 4B) HIF-1$\alpha$, PDGFB, VEGF, and Frizzled4 levels in homogenates of experimental miRNA-treated and control miRNA-treated retinas, measured by immunoblot analysis. Each immunoblot was repeated at least once with similar results.

FIG. 5A. Mouse eyes were injected with negative control miRNA. FIG. 5B. Mouse eyes were injected with a mixture of synthetic mmu-miR-31, -150, and -184. Brightly fluorescent areas are areas of neovascularization.

(FIG. 7A) Mouse eyes were injected with negative control miRNA. (FIG. 7B) Mouse eyes were injected with a mixture of synthetic mmu-miR-31, -150, and -184. Brightly fluorescent areas are areas of neovascularization.

DETAILED DESCRIPTION OF THE INVENTION

Figures 1A, 1B:
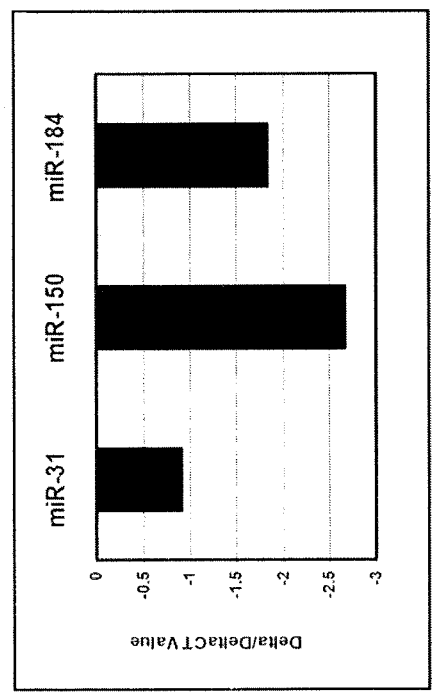
FIGS. 1A-1B. QRT-PCR quantification of mmu-miR-31, mmu-miR-150, and mmu-miR-184 in mouse retinas undergoing neovascularization. Mean threshold cycle numbers ($\Delta$CT) were determined for RNA from ischemic and control retinas (n=5 each) and the mean difference ($\Delta\Delta$CT) ranged from about −1.0 (miR-31) to −2.5 (miR-150) (FIG. 1A). Statistical comparisons confirmed that the quantity of each miRNA was significantly reduced in ischemic compared to control retinas (FIG. 1B).

The present invention is directed to compositions and methods relating to preparation and characterization of miRNAs, as well as use of miRNAs for therapeutic, prognostic, and/or diagnostic applications, particularly those methods and compositions related to assessing and/or identifying conditions associated with aberrant or abnormal vascularization and/or angiogenesis.

I. Neovascularization and Angiogenesis

Neovascularization refers to the proliferation of blood vessels that are atypical for tissues containing them or the proliferation of blood vessels distinct from those that are normally found in the tissue. Neovascularization occurs through a complex process called angiogenesis. Angiogenesis is regulated by a mixture of stimulators and inhibitors that are balanced to ensure the proper development of blood vessels in the body. Mis-regulated angiogenesis is the underlying cause of numerous diseases and a contributor to many more.

Inhibition of angiogenesis can be a useful therapy for diseases such as diabetic nephropathy, rheumatoid arthritis, atherosclerotic plaques, endometriosis, Crohn's disease, uterine fibroids, benign prostatic hyperplasia, psoriasis, and cancer. In 1988, interferon α2a was first used as an antiangiogenic drug to treat children with life-threatening hemangiomas, a nonmalignant vascular tumor (White et al., 1989; Folkman, 1989). Several hundred angiogenesis inhibitors have since been discovered and many of these have been evaluated for therapeutic utility in clinical trials. Many of these compounds have not proved useful for disease therapy. However, some cancer patients have experienced dramatic regression of their tumors from antiangiogenic therapy, and others have experienced stabilization of their disease. The first FDA-approved blood vessel therapy for eye disease was Visudyne (QLT Therapeutics/CibaVision), which has shown effectiveness for treating macular degeneration. Additional angiogenesis inhibitors have since been approved for the treatment of macular degeneration.

In contrast, stimulation of angiogenesis can be a useful therapy for the treatment of coronary artery disease (CAD), cardiac failure, tissue injury, and ischemic diseases such as ischemic CAD, critical limb ischemia with various etiologies, and decubitus. The first FDA-approved device to stimulate growth of new blood vessels in diseased hearts was a laser used in a technique referred to as direct myocardial revascularization (DMR) or transmyocardial revascularization (TMR). The first angiogenesis-stimulating medicine was a prescription gel called Regranex (recombinant human platelet-derived growth factor-BB, Ortho-McNeil Pharmaceuticals) that is approved for treatment of diabetic foot ulcers. Numerous angiogenic growth factors and angiogenic gene therapies are now being developed or tested in humans for growing new blood vessels to heal wounds and for restoring blood flow to the heart, limbs, and brain.

Although differences exist among vascular beds throughout the body, the genes and molecules involved in stimulating or inhibiting neovascularization tend to be common. Animal models for retinal and choroidal neovascularization (CNV) have proved useful in understanding the molecular events leading to blood vessel formation (Campochiaro and Hackett, 2003). Consistent with neovascularization in other tissues, retinal and choroidal neovascularization is stimulated by vascular endothelial growth factor (VEGF) (Aiello et al., 1995; Miller et al., 1994; Ozaki et al., 2000; Kwak et al., 2000). Intraocular injections of ranibizumab, an Fab that binds all isoforms of VEGF-A, resulted in significant visual improvement in 35-40% of patients with CNV caused by age-related macular degeneration (AMD) (Rosenfeld et al., 2006; Brown and Regillo, 2007). While this has benefited many patients with CNV, the remaining 60-65% of CNV patients will need another type of treatment to realize vision improvement.

Transcriptional regulation of many genes is clearly important for determining the balance of stimulators and inhibitors of neovascularization. In addition, mounting evidence now suggests that microRNAs may play a complementary role in regulation of neovascularization. MicroRNAs (miRNAs) are small non-coding RNAs, comprising an evolutionarily conserved class of regulatory nucleic acids ranging in size from 14-35 nucleotides in their mature form. miRNA precursors are processed by cellular proteins, including Drosha and Dicer, to generate a short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA to its target mRNA (Bagga et al., 2005; Lim et al., 2005). In mice, targeted disruption of Dicer, results in death during the embryonic growth phase, due to disruption of vascular development (Yang et al., 2005). More recently, two miRNAs (miR-221 and miR-222) have been shown to modulate the angiogenic properties of human umbilical vein endothelial cells (Poliseno et al., 2006).

Compositions and methods of the present invention can be used to inhibit neovascularization. Accordingly, the present invention discloses methods of using miRNA or miRNA inhibitor for treating a variety of diseases with a neovascularization component (hereinafter collectively referred to as "neovascularization diseases" or "conditions associated with aberrant vascularization or angiogenesis") or other similar phrases. In one embodiment, the present invention provides a method of treating pathological conditions resulting from angiogenesis or neovascularization comprising administration of an effective amount of an miRNA or an miRNA inhibitor.

Diseases of the eye treatable using the present invention include, but are not limited to retinopathy of prematurity (ROP), age-related macular degeneration (AMD), diabetic retinopathy, hypertensive retinopathy, central retinal vein occlusion (CRVO), branch vein occlusion (BRVO), neovascular glaucoma, ocular ischemic syndrome, occlusive vasculitis, polypoidal choroidal vasculopathy, myopic choroidal neovascularization, radiation retinopathy, chorioretinitis, central serous choroidopathy, central retinal artery occlusion, uveitic macular edema, idiopathic juxtafoveal telangiectasia, angioid streaks, sickle cell retinopathy, and pseudophakic cystoid macular edema. All of these diseases share the same mechanism of choroidal neovascularization and/or retinal neovascularization, the inhibition of which will result in treatment of the diseases.

Other diseases of the eye treatable by the present invention include, but are not limited to, primary ocular tumors, such as uveal melanomas, melanocytomas, retinocytomas, retinal hamartomas and choristomas, retinal angiomas, retinal gliomas and astrocytomas, choroidal hemangiomas, choroidal neurofibromas, choroidal hamartomas and choristomas, ocular lymphomas and ocular phakomatoses; and metastatic ocular tumors related to choroidal and retinal neovascularization.

In addition, the present invention is suitable for the treatment of cancers such as, but not limited to medulloblastoma, pineoblastoma, non-pineal supratententorial, and Ewings sarcoma.

II. Mirna Based Therapy

Embodiments of the invention concern nucleic acids that perform the activities of or inhibit endogenous miRNAs when introduced into cells. In certain aspects, nucleic acids are synthetic or non-synthetic miRNA. Sequence-specific miRNA or miRNA inhibitors can be used to inhibit sequentially or in combination the activities of one or more endogenous miRNAs in cells, as well those genes and associated pathways modulated by the endogenous miRNA.

Methods of the invention include supplying or enhancing the activity of one or more miRNAs in a cell. The present invention also concerns inducing certain cellular characteristics by providing to a cell a particular nucleic acid, such as a specific synthetic miRNA molecule. However, in methods of the invention, the miRNA molecule or miRNA inhibitor need not be synthetic. They may have a sequence that is identical to a naturally occurring miRNA or they may not have any design modifications. In certain embodiments, the miRNA molecule is synthetic, as discussed herein.

The particular nucleic acid molecule provided to the cell is understood to correspond to a particular miRNA in the cell, and thus, the miRNA in the cell is referred to as the "corresponding miRNA." In situations in which a named miRNA molecule is introduced into a cell, the corresponding miRNA will be understood to be the induced or inhibited miRNA or induced or inhibited miRNA function. It is contemplated, however, that the miRNA molecule introduced into a cell is not a mature miRNA but is capable of becoming or functioning as a mature miRNA under the appropriate physiological conditions. It is contemplated that multiple corresponding miRNAs may be involved. A miRNA may have a minimal adverse effect on a subject or patient while supplying a sufficient therapeutic effect, such as amelioration of a condition, growth inhibition of a cell, death of a targeted cell, alteration of cell phenotype or physiology, slowing of cellular growth, sensitization to a second therapy, sensitization to a particular therapy, and the like. Methods include identifying a cell or patient in need of inducing those cellular characteristics. Also, it will be understood that an amount of a synthetic nucleic acid that is provided to a cell or organism is an "effective amount" or "amount sufficient" for a particular result, which refers to an amount needed (or a sufficient amount) to achieve a desired goal, such as inducing a particular cellular characteristic(s), inhibiting vascularization or stimulating vascularization. In certain embodiments of the methods include providing or introducing to a cell a nucleic acid molecule corresponding to a mature miRNA in the cell in an amount effective to achieve a desired physiological result. Moreover, methods can involve providing synthetic or nonsynthetic miRNA molecules. Furthermore, any method articulated using a list of miRNAs using Markush group language may be articulated without the Markush group language and a disjunctive article (i.e., or) instead, and vice versa.

In some embodiments, there is a method for reducing or inhibiting vascularization comprises introducing into or providing a subject, tissue, or cell an effective amount of a synthetic or nonsynthetic miRNA molecule that corresponds to a miRNA sequence disclosed herein, or a complement or inhibitor thereof.

Certain embodiments of the invention include methods of treating a pathologic condition. In one aspect, the method comprises contacting a target cell with one or more nucleic acid, synthetic miRNA, or miRNA comprising at least one nucleic acid segment having all or a portion of a miRNA sequence. The segment may be 5, 6, 7, 8, 9, 10, 11, 12, 13, 14, 15, 16, 17, 18, 19, 20, 21, 22, 23, 24, 25, 30 or more nucleotides or nucleotide analog including all integers there between. In certain aspects, one or more nucleotide of a nucleic acid can be modified. An aspect of the invention includes the modulation of gene expression, miRNA expression or function, or mRNA expression or function within a target subject, tissue, or cell.

Typically, an endogenous gene, miRNA or mRNA is modulated in the cell. In particular embodiments, the nucleic acid sequence comprises at least one segment that is at least 70, 75, 80, 85, 90, 95, 96, 97, 98, 99, or 100% identical in nucleic acid sequence to one or more miRNA or gene sequence. Modulation of the expression or processing of an endogenous gene, miRNA, or mRNA can be through modulation of the processing of a mRNA, such processing including transcription, transportation and/or translation in a cell. Modulation may also be effected by the inhibition or enhancement of miRNA activity in a cell, tissue, or organ. Such processing may affect the expression of an encoded product or the stability of the mRNA. In still other embodiments, a nucleic acid sequence can comprise a modified nucleic acid sequence. In certain aspects, one or more miRNA sequence may include or comprise a modified nucleobase or nucleic acid sequence.

It will be understood in methods of the invention that a cell or other biological matter such as an organism (including patients or subjects) can be provided a miRNA or miRNA molecule corresponding to a particular miRNA by administering to the cell or organism a nucleic acid molecule that functions as the corresponding miRNA once inside the cell. In certain embodiments, it is specifically contemplated that the miRNA molecule provided to the biological matter is not a mature miRNA molecule but a nucleic acid molecule that can be processed into the mature miRNA once it is accessible to miRNA processing machinery. The term "nonsynthetic" in the context of miRNA means that the miRNA is not "synthetic," as defined herein. Furthermore, it is contemplated that in embodiments of the invention that concern the use of synthetic miRNAs, the use of corresponding nonsynthetic miRNAs is also considered an aspect of the invention, and vice versa. It will be understand that the term "providing" an agent is used to include "administering" the agent to a patient.

In certain methods of the invention, there is a further step of administering the selected miRNA modulator to a cell, tissue, organ, or organism (collectively "biological matter") in need of treatment related to modulation of the targeted miRNA or in need of the physiological or biological results discussed herein (such as with respect to a particular cellular pathway or result like inhibition of vascularization or angiogenesis, or stimulation or promotion of vascularization or angiogenesis).

Consequently, in some methods of the invention there is a step of identifying a patient in need of treatment that can be provided by the miRNA modulator(s). It is contemplated that an effective amount of a miRNA modulator can be administered in some embodiments. In particular embodiments, there is a therapeutic benefit conferred on the biological matter, where a "therapeutic benefit" refers to an improvement in the one or more conditions or symptoms associated with a disease or condition or an improvement in the prognosis, duration, or status with respect to the disease. It is contemplated that a therapeutic benefit includes, but is not limited to, a decrease in pain, a decrease in morbidity, a decrease in a symptom. For example, with respect to cancer, it is contemplated that a therapeutic benefit can be inhibition of tumor growth, prevention of metastasis, reduction in number of metastases, inhibition of cancer cell proliferation, induction of cell death in cancer cells, inhibition of angiogenesis near cancer cells, induction of apoptosis of cancer cells, reduction in pain, reduction in risk of recurrence, induction of chemo- or radiosensitivity in cancer cells, prolongation of life, and/or delay of death directly or indirectly related to cancer.

Furthermore, it is contemplated that the miRNA compositions may be provided as part of a therapy to a patient, in conjunction with traditional therapies or preventative agents. Moreover, it is contemplated that any method discussed in the context of therapy may be applied as a preventative measure, particularly in a patient identified to be potentially in need of the therapy or at risk of the condition or disease for which a therapy is needed.

A nucleic acid of the invention can enhance the effect or efficacy of a drug, reduce any side effects or toxicity, modify its bioavailability, and/or decrease the dosage or frequency needed. In certain embodiments, the therapeutic drug is a anti-vascularization, pro-vascularization, and/or a cancer therapeutic. Consequently, in some embodiments, there is a method of treating a patient comprising administering to the patient the therapeutic and an effective amount of a miRNA molecule that improves the efficacy of a second therapeutic or protects non-targeted cells from a detrimental affect of a drug. Therapies also include a variety of combination therapies with both chemical and radiation based treatments. Combination chemotherapies include but are not limited to, for example, 5-fluorouracil, alemtuzumab, amrubicin, bevacizumab, bleomycin, bortezomib, busulfan, camptothecin, capecitabine, cisplatin (CDDP), carboplatin, cetuximab, chlorambucil, cisplatin (CDDP), EGFR inhibitors (gefitinib and cetuximab), procarbazine, mechlorethamine, cyclophosphamide, camptothecin, COX-2 inhibitors (e.g., celecoxib), cyclophosphamide, cytarabine) ifosfamide, melphalan, chlorambucil, busulfan, nitrosurea, dactinomycin, dasatinib, daunorubicin, dexamethasone, docetaxel, doxorubicin (adriamycin), EGFR inhibitors (gefitinib and cetuximab), erlotinib, estrogen receptor binding agents, bleomycin, plicomycin, mitomycin, etoposide (VP16), everolimus, tamoxifen, raloxifene, estrogen receptor binding agents, taxol, taxotere, gemcitabien, navelbine, farnesyl-protein transferase inhibitors, gefitinib, gemcitabine, gemtuzumab, ibritumomab, ifosfamide, imatinib mesylate, larotaxel, lapatinib, lonafarnib, mechlorethamine, melphalan, transplatinum, 5-fluorouracil, vincristin, vinblastin and methotrexate, mitomycin, navelbine, nitrosurea, nocodazole, oxaliplatin, paclitaxel, plicomycin, procarbazine, raloxifene, rituximab, sirolimus, sorafenib, sunitinib, tamoxifen, taxol, taxotere, temsirolimus, tipifarnib, tositumomab, transplatinum, trastuzumab, vinblastin, vincristin, or vinorelbine or any analog or derivative variant of the foregoing.

III. Nucleic Acids

The present invention concerns nucleic acids, modified nucleic acids, nucleic acid mimetics, miRNAs, and segments thereof that can be employed in therapeutic applications, particularly those applications related to pathological conditions. The molecules may have been endogenously produced by a cell and isolated, or synthesized or produced chemically or recombinantly. They may be isolated and/or purified. Each of the miRNAs described herein includes the corresponding SEQ ID NO and accession numbers for these miRNA sequences. The name of a miRNA is often abbreviated and referred to without a "hsa-" prefix and will be understood as such, depending on the context. Unless otherwise indicated, miRNAs referred to in the application are human sequences identified as miR-X or let-X, where X is a number and/or letter.

In certain aspects, a miRNA designated by a suffix "5P" or "3P" can be used. "5P" indicates that the mature miRNA derives from the 5' end of the precursor and a corresponding "3P" indicates that it derives from the 3' end of the precursor, as described on the world wide web at sanger.ac.uk. Moreover, in some embodiments, a miRNA probe is used that does not correspond to a known human miRNA. It is contemplated that these non-human miRNA probes may be used in embodiments of the invention or that there may exist a human miRNA that is homologous to the non-human miRNA. In other embodiments, any mammalian cell, biological sample, or preparation thereof may be employed.

The present invention concerns, in some embodiments, short nucleic acid molecules that function as miRNAs in a cell. The term "short" refers to a length of a single polynucleotide that is at least, at most, or about 6, 7, 8, 9, 10, 11, 12, 13, 14, 15, 16, 17, 18, 19, 20, 21, 22, 23, 24, 25, 50, 100, or 150 nucleotides, including all integers or ranges derivable there between. The nucleic acid molecules are typically synthetic. The term "synthetic" refers to a nucleic acid molecule that is isolated and not produced naturally in a cell. In certain aspects the sequence (the entire sequence) and/or chemical structure deviates from a naturally-occurring nucleic acid molecule, such as an endogenous precursor miRNA or miRNA molecule or complement thereof. While in some embodiments, nucleic acids of the invention do not have an entire sequence that is identical or complementary to a sequence of a naturally-occurring nucleic acid, such molecules may encompass all or part of a naturally-occurring sequence or a complement thereof. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA or an inhibitor thereof.

The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together. In certain aspects, synthetic miRNA of the invention are RNA or RNA analogs. miRNA inhibitors may be DNA or RNA, or analogs thereof.

In some embodiments, there is a miRNA or a synthetic miRNA having a length of between 10 and 130 residues. The present invention concerns miRNA or synthetic miRNA molecules that are, are at least, or are at most 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range there between.

In certain embodiments, synthetic miRNA have (a) a "miRNA region" whose sequence or binding region from 5' to 3' is identical or complementary to all or a segment of a mature miRNA sequence, and (b) a "complementary region" whose sequence from 5' to 3' is between 60% and 100% complementary to the miRNA sequence in (a). In certain embodiments, these synthetic miRNA are also isolated, as defined above. The term "miRNA region" or complement thereof refers to a region on the synthetic miRNA that is at least 75, 80, 85, 90, 95, or 100% identical, including all integers there between, to the entire sequence of a mature, naturally occurring miRNA sequence or a complement thereof. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA or complement thereof. In certain aspects, a double stranded RNA can comprise a miR sequence that is 90 to 100% identical to sequences described herein, as described directly above, and a second nucleic acid that is complementary to the miR sequence and is 60, 65, 70, 75, 80, 85, 90, 95, or 100% identical, including all integers there between, to the miR sequence.

The term "complementary region" or "complement" refers to a region of a nucleic acid or mimetic that is or is at least 60% complementary to the mature, naturally occurring miRNA sequence. The complementary region can be at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9 or 100% complementary including all values and ranges there between. With single polynucleotide sequences, there may be a hairpin loop structure as a result of chemical bonding between the miRNA region and the complementary region. In other embodiments, the complementary region is on a different nucleic acid molecule than the miRNA region, in which case the complementary region is on the complementary strand and the miRNA region is on the active strand.

In some embodiments of the invention a synthetic miRNA contains one or more design element(s). These design elements include, but are not limited to: (i) a replacement group for the phosphate or hydroxyl of the nucleotide at the 5' terminus of the complementary region; (ii) one or more sugar modifications in the first or last 1 to 6 residues of the complementary region; or, (iii) noncomplementarity between one or more nucleotides in the last 1 to 5 residues at the 3' end of the complementary region and the corresponding nucleotides of the miRNA region. A variety of design modifications are known in the art, see below.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2' oxygen-methyl), DMTO (4,4'-dimethoxytrityl with oxygen), fluoroscein, a thiol, or acridine, though other replacement groups are well known to those of skill in the art and can be used as well. This design element can also be used with a miRNA inhibitor.

Additional embodiments concern a synthetic miRNA having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there are one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification, a 2'F modification, a 2'H modification, a 2' amino modification, a 4'thioribose modification or a phosphorothioate modification on the carboxy group linked to the carbon at position 6'. In further embodiments, there are one or more sugar modifications in the first or last 2 to 4 residues of the complementary region or the first or last 4 to 6 residues of the complementary region. This design element can also be used with a miRNA inhibitor. Thus, a miRNA inhibitor can have this design element and/or a replacement group on the nucleotide at the 5' terminus, as discussed above.

In other embodiments of the invention, there is a synthetic miRNA in which one or more nucleotides in the last 1 to 5 residues at the 3' end of the complementary region are not complementary to the corresponding nucleotides of the miRNA region ("noncomplementarity") (referred to as the "noncomplementarity design"). The noncomplementarity may be in the last 1, 2, 3, 4, and/or 5 residues of the complementary miRNA. In certain embodiments, there is noncomplementarity with at least 2 nucleotides in the complementary region.

It is contemplated that synthetic miRNA of the invention have one or more of the replacement, sugar modification, or noncomplementarity designs. In certain cases, synthetic RNA molecules have two of them, while in others these molecules have all three designs in place.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there can be a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

In some embodiments of the invention, methods and compositions involving miRNA may concern nucleic acids comprising miRNA nucleotide sequences. Nucleic acids may be, be at least, or be at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length. Such lengths cover the lengths of processed miRNA, precursor miRNA, miRNA containing vectors, and therapeutic miRNA. In many embodiments, miRNA are 14-35 nucleotides in length. miRNA precursors are generally between 62 and 110 nucleotides in humans.

It is understood that some nucleic acids are derived from genomic sequences or a gene. In this respect, the term "gene" is used for simplicity to refer to the genomic sequence encoding the precursor nucleic acid or miRNA for a given miRNA or gene. However, embodiments of the invention may involve genomic sequences of a miRNA that are involved in its expression, such as a promoter or other regulatory sequences.

The term "recombinant" may be used and this generally refers to a molecule that has been manipulated in vitro or that is a replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, miRNA nucleic acids may encompass a molecule that comprises one or more complementary or self-complementary strand(s) or "complement(s)" of a particular sequence. For example, precursor miRNA may have a self-complementary region, which is up to 100% complementary. miRNA probes or nucleic acids of the invention can include, can be or can be at least 60, 65, 70, 75, 80, 85, 90, 95, 96, 97, 98, 99 or 100% complementary to their target.

It is understood that a "synthetic nucleic acid" of the invention means that the nucleic acid does not have all or part of a chemical structure or sequence of a naturally occurring nucleic acid or was made by man and not a biologic cell or organism. Consequently, it will be understood that the term "synthetic miRNA" refers to a "synthetic nucleic acid" that functions in a cell or under physiological conditions as a naturally occurring miRNA.

While embodiments of the invention may involve synthetic miRNAs or synthetic nucleic acids, in some embodiments of the invention, the nucleic acid molecule(s) need not be "synthetic." In certain embodiments, a non-synthetic nucleic acid or miRNA employed in methods and compositions of the invention may have the entire sequence and structure of a naturally occurring mRNA or miRNA precursor or the mature mRNA or miRNA. For example, non-synthetic miRNAs used in methods and compositions of the invention may not have one or more modified nucleotides or nucleotide analogs. In these embodiments, the non-synthetic miRNA may or may not be recombinantly produced. In particular embodiments, the nucleic acid in methods and/or compositions of the invention is specifically a synthetic miRNA and not a non-synthetic miRNA (that is, not a miRNA that qualifies as "synthetic"); though in other embodiments, the invention specifically involves a non-synthetic miRNA and not a synthetic miRNA. Any embodiments discussed with respect to the use of synthetic miRNAs can be applied with respect to non-synthetic miRNAs, and vice versa.

It will be understood that the term "naturally occurring" refers to something found in an organism without any intervention by a person; it could refer to a naturally-occurring wildtype or mutant molecule. In some embodiments a synthetic miRNA molecule does not have the sequence of a naturally occurring miRNA molecule. In other embodiments, a synthetic miRNA molecule may have the sequence of a naturally occurring miRNA molecule, but the chemical structure of the molecule, particularly in the part unrelated specifically to the precise sequence (non-sequence chemical structure) differs from chemical structure of the naturally occurring miRNA molecule with that sequence. In some cases, the synthetic miRNA has both a sequence and non-sequence chemical structure that are not found in a naturally-occurring miRNA. Moreover, the sequence of the synthetic molecules will identify which miRNA is effectively being provided; the endogenous miRNA will be referred to as the "corresponding miRNA." Corresponding miRNA sequences that can be used in the context of the invention include, but are not limited to, all or a portion of those sequences in the SEQ IDs provided herein, as well as any other miRNA sequence, miRNA precursor sequence, or any sequence complementary thereof. In some embodiments, the sequence is or is derived from or contains all or part of a sequence identified herein to target a particular miRNA (or set of miRNAs) that can be used with that sequence. Any 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130 140, 150, 160, 170, 180, 190, 200, 210, 220, 230, 240, 250, 260 or any number or range of sequences there between may be selected to the exclusion of all non-selected sequences.

1. Nucleobase, Nucleoside, Nucleotide, and Modified Nucleotides

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or nonnaturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moiety. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring. Different types of covalent attachment(s) of a nucleobase to a nucleobase linker moiety are known in the art (Kornberg and Baker, 1992).

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids include those in: U.S. Pat. Nos. 5,681, 947, 5,652,099 and 5,763,167, 5,614,617, 5,670,663, 5,872, 232, 5,859,221, 5,446,137, 5,886,165, 5,714,606, 5,672,697, 5,466,786, 5,792,847, 5,223,618, 5,470,967, 5,378,825, 5,777,092, 5,623,070, 5,610,289, 5,602,240, 5,858,988, 5,214,136, 5,700,922, 5,708,154, 5,728,525, 5,637,683, 6,251,666, 5,480,980, and 5,728,525, each of which is incorporated herein by reference in its entirety.

Labeling methods and kits of the invention specifically contemplate the use of nucleotides that are both modified for attachment of a label and can be incorporated into a miRNA molecule. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Modified nucleotides for use in the invention are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments is alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, Biosearch Technologies and NEN. Functional groups may be prepared according to ways known to those of skill in the art, including the representative information found in U.S. Pat. Nos. 4,404,289; 4,405,711; 4,337,063 and 5,268, 486, and U.K. Patent 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; N6-(4-amino)butyl-ATP, N6-(6-amino)butyl-ATP, N4-[2,2-oxy-bis-(ethylamine)]-CTP; N6-

(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N6-(4-amino)butyl-dATP, N6-(6-amino)butyl-dATP, N4-[2,2-oxy-bis-(ethylamine)]-dCTP; N6-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

B. Preparation of Nucleic Acids

A nucleic acid may be made by any technique known to one of ordinary skill in the art, such as for example, chemical synthesis, enzymatic production, or biological production. It is specifically contemplated that miRNA probes of the invention are chemically synthesized.

In some embodiments of the invention, miRNAs are recovered or isolated from a biological sample. The miRNA may be recombinant or it may be natural or endogenous to the cell (produced from the cell's genome). It is contemplated that a biological sample may be treated in a way so as to enhance the recovery of small RNA molecules such as miRNA. U.S. patent application Ser. No. 10/667,126 describes such methods and it is specifically incorporated by reference herein. Generally, methods involve lysing cells with a solution having guanidinium and a detergent.

Alternatively, nucleic acid synthesis is performed according to standard methods. See, for example, Itakura and Riggs (1980) and U.S. Pat. Nos. 4,704,362, 5,221,619, and 5,583, 013, each of which is incorporated herein by reference. Non-limiting examples of a synthetic nucleic acid (e.g., a synthetic oligonucleotide), include a nucleic acid made by in vitro chemical synthesis using phosphotriester, phosphite, or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705, 629, each incorporated herein by reference. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. See also Sambrook et al., 2001, incorporated herein by reference).

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Recombinant methods for producing nucleic acids in a cell are well known to those of skill in the art. These include the use of vectors (viral and non-viral), plasmids, cosmids, and other vehicles for delivering a nucleic acid to a cell, which may be the target cell (e.g., a cancer cell) or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

C. Isolation of Nucleic Acids

Nucleic acids may be isolated using techniques well known to those of skill in the art, though in particular embodiments, methods for isolating small nucleic acid molecules, and/or isolating RNA molecules can be employed. Chromatography is a process often used to separate or isolate nucleic acids from protein or from other nucleic acids. Such methods can involve electrophoresis with a gel matrix, filter columns, alcohol precipitation, and/or other chromatography. If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix is prepared using polyacrylamide, though agarose can also be used. The gels may be graded by concentration or they may be uniform. Plates or tubing can be used to hold the gel matrix for electrophoresis. Usually one-dimensional electrophoresis is employed for the separation of nucleic acids. Plates are used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased, such as from C.B.S. Scientific Co., Inc. or Scie-Plas.

Methods may involve the use of organic solvents and/or alcohol to isolate nucleic acids, particularly miRNA used in methods and compositions of the invention. Some embodiments are described in U.S. patent application Ser. No. 10/667,126, which is hereby incorporated by reference. Generally, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column has worked particularly well for such isolation procedures.

In specific embodiments, miRNA isolation processes include: (a) lysing cells in the sample with a lysing solution comprising guanidinium, wherein a lysate with a concentration of at least about 1 M guanidinium is produced; (b) extracting miRNA molecules from the lysate with an extraction solution comprising phenol; (c) adding to the lysate an alcohol solution for forming a lysate/alcohol mixture, wherein the concentration of alcohol in the mixture is between about 35% to about 70%; (d) applying the lysate/alcohol mixture to a solid support; (e) eluting the miRNA molecules from the solid support with an ionic solution; and, (f) capturing the miRNA molecules. Typically the sample is dried and resuspended in a liquid and volume appropriate for subsequent manipulation.

IV. Pharmaceutical Formulations and Delivery

Methods of the present invention include the delivery of an effective amount of a miRNA or an expression construct encoding the same. An "effective amount" of the pharmaceutical composition, generally, is defined as that amount sufficient to detectably achieve a desired result, for example, to ameliorate, reduce, minimize or limit the extent of a disease or its symptoms. Other more rigorous definitions may apply, including elimination, eradication or cure of disease.

A. Administration

In certain embodiments, it is desired to inhibit vascularization, stimulate vascularization, kill cells, inhibit cell growth, inhibit metastasis, decrease tumor or tissue size, and/or reverse or reduce the malignant or disease phenotype of cells. The routes of administration will vary, naturally, with the location and nature of the lesion or site to be targeted, and include, e.g., intradermal, subcutaneous, regional, parenteral, intravenous, intramuscular, intranasal, systemic, and oral administration and formulation. Direct injection, local injection, or injection into vasculature at a target site is specifically contemplated for target areas. Local, regional, or systemic administration also may be appropriate.

Multiple injections delivered as a single dose comprise about 0.1 to about 0.5 ml volumes. Compositions of the invention may be administered in multiple injections to a tumor or a targeted site. In certain aspects, injections may be spaced at approximately 1 cm intervals.

In the case of surgical intervention, the present invention may be used preoperatively, to render an inoperable target area subject to resection. Alternatively, the present invention may be used at the time of surgery, and/or thereafter, to treat residual or recurring disease. For example, a resected tumor bed may be injected or perfused with a formulation comprising a miRNA or combinations thereof. Administration may be continued post-resection, for example, by leaving a catheter implanted at the site of the surgery. Periodic post-surgical treatment also is envisioned. Continuous perfusion of an expression construct or a viral construct also is contemplated.

Continuous administration also may be applied where appropriate, for example, where a tumor or other undesired affected area is excised and the tumor bed or targeted site is treated to eliminate residual, microscopic disease. Delivery via syringe or catherization is contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs.

Treatment regimens may vary as well and often depend on lesion type, tumor type, location, immune condition, target site, disease progression, and health and age of the patient. Certain tumor types will require more aggressive treatment. The clinician will be best suited to make such decisions based on the known efficacy and toxicity (if any) of the therapeutic formulations.

In certain embodiments, the tumor or affected area being treated may not, at least initially, be resectable or operable. Treatments with compositions of the invention may increase the respectability of the tumor or target site due to shrinkage at the margins or by elimination of certain particularly invasive portions. Following treatments, resection may be possible. Additional treatments subsequent to resection may serve to eliminate microscopic residual disease at the tumor or targeted site.

Treatments may include various "unit doses." A unit dose is defined as containing a predetermined quantity of a therapeutic composition(s). The quantity to be administered, and the particular route and formulation, are within the skill of those in the clinical arts. A unit dose need not be administered as a single injection but may comprise continuous infusion over a set period of time. With respect to a viral component of the present invention, a unit dose may conveniently be described in terms of μg or mg of miRNA or miRNA mimetic. Alternatively, the amount specified may be the amount administered as the average daily, average weekly, or average monthly dose.

miRNA can be administered to the patient in a dose or doses of about or of at least about 0.005, 0.05, 0.5, 1, 5, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 μg, ng, or mg, or more, or any range derivable therein. Alternatively, the amount specified may be the amount administered as the average daily, average weekly, or average monthly dose, or it may be expressed in terms of mg/kg, where kg refers to the weight of the patient and the mg is specified above. In other embodiments, the amount specified is any number discussed above but expressed as $mg/m^2$ (with respect to tumor size or patient surface area).

B. Injectable Compositions and Formulations

In some embodiments, the method for the delivery of a miRNA or an expression construct encoding such or combinations thereof is via systemic administration. However, the pharmaceutical compositions disclosed herein may also be administered topically, parenterally, subcutaneously, directly, intratracheally, intravenously, intradermally, intramuscularly, or even intraperitoneally as described in U.S. Pat. Nos. 5,543,158; 5,641,515 and 5,399,363 (each specifically incorporated herein by reference in its entirety).

Injection of nucleic acids may be delivered by syringe or any other method used for injection of a solution, as long as the nucleic acid and any associated components can pass through the particular gauge of needle required for injection. A syringe system has also been described for use in gene therapy that permits multiple injections of predetermined quantities of a solution precisely at any depth (U.S. Pat. No. 5,846,225).

Solutions of the active compounds are typically sterile and must be fluid to the extent that easy syringability exists. It must be sufficiently stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

In certain formulations, a water-based formulation is employed while in others, it may be lipid-based. In particular embodiments of the invention, a composition comprising a tumor suppressor protein or a nucleic acid encoding the same is in a water-based formulation. In other embodiments, the formulation is lipid based.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral, intralesional, and intraperitoneal administration. In this connection, sterile aqueous media which can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety, and purity standards as required by FDA Office of Biologics standards.

As used herein, a "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human.

The nucleic acid(s) are administered in a manner compatible with the dosage formulation, and in such amount as will be therapeutically effective. The quantity to be administered depends on the subject to be treated, including, e.g., the aggressiveness of the disease or cancer, the size of any tumor(s) or lesions, the previous or other courses of treatment. Precise amounts of active ingredient required to be administered depend on the judgment of the practitioner. Suitable regimes for initial administration and subsequent administration are also variable, but are typified by an initial administration followed by other administrations. Such administration may be systemic, as a single dose, continuous over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration.

C. Combination Treatments

In certain embodiments, the compositions and methods of the present invention involve a miRNA, or miRNA inhibitor, or expression construct encoding such. These miRNA compositions can be used in combination with a second therapy to enhance the effect of the miRNA therapy, or increase the therapeutic effect of another therapy being employed. These compositions would be provided in a combined amount effective to achieve the desired effect, such as inhibiting or stimulating vascularization, killing of a cancer cell and/or inhibition of cellular hyperproliferation. This process may involve contacting the cells with the miRNA or second therapy at the same or different time. This may be achieved by contacting the cell with one or more compositions or pharmacological formulation that includes or more of the agents, or by contacting the cell with two or more distinct compositions or formulations, wherein one composition provides (1) miRNA; and/or (2) a second therapy. A second composition or method may be administered that includes an antiangiogenic or pro-angiogenic therapy, chemotherapy, radiotherapy, surgical therapy, immunotherapy, or gene therapy.

It is contemplated that one may provide a patient with the miRNA therapy and the second therapy within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

Various combinations may be employed, for example miRNA therapy is "A" and a second therapy is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of any compound or therapy of the present invention to a patient will follow general protocols for the administration of such compounds, taking into account the toxicity, if any, of the vector or any protein or other agent. Therefore, in some embodiments there is a step of monitoring toxicity that is attributable to combination therapy. It is expected that the treatment cycles would be repeated as necessary. It also is contemplated that various standard therapies, as well as surgical intervention, may be applied in combination with the described therapy. Cancer therapeutics can involve the application of multiple targeted therapies that include Tarceva, Iressa, Herceptin, and other targeted therapeutics along with radiation and chemotherapies.

In specific aspects, it is contemplated that a second therapy, such as chemotherapy, radiotherapy, immunotherapy, surgical therapy or other gene therapy, is employed in combination with the miRNA therapy, as described herein.

1. Antiangiogenic Therapy

Antiangiogenic therapy includes, but is not limited to Macugen, Visudyne, and Photodynamic Therapy (PDT) for macular degeneration and other diseases of the eye.

Angiogenesis inhibitors which inhibit angiogenesis in treated tissues can be used in the compositions and methods of the invention. Angiogenesis inhibitors include $\alpha_v$ antagonist, and in particular a $\alpha_v\beta_3$ antagonist. An angiogenesis inhibiting (anti-angiogenesis) $\alpha_v\beta_3$ antagonist can be a peptide, a RGD-containing peptide, an anti-$\alpha_v\beta_3$ antibody, an anti-$\alpha_v\beta_3$ receptor antibody, or an $\alpha_v\beta_3$ mimetic. Exemplary antiangiogenic substances are described in the teachings of U.S. Pat. Nos. 5,753,230, 5,766,591, and U.S. Patent publications 20080039384, 20080014196, 20080096795, 20080090750, International Publication No. WO 97/45137, the disclosures of which are specifically incorporated herein by reference.

Other compounds have been identified on the basis of the ability for the compound to inhibit angiogenesis and include but are not limited to prostate specific antigen (PSA); soluble VEGFR-1 and NRP-1; Angiopoietin 2; TSP-1 and TSP-2; angiostatin and related molecules; endostatin; vasostatin; calreticulin; platelet factor-4; TIMP and CDAI; Meth-1 and Meth-2; IFN-$\alpha$, -$\beta$ and -$\gamma$; CXCL10; IL-4, -12 and -18; prothrombin (kringle domain-2); antithrombin III fragment; prolactin; VEGI; SPARC; osteopontin; maspin; canstatin; proliferin-related protein; restin; bevacizumab; carboxyamidotriazole; TNP-470; CM101; suramin; SU5416; thrombospondin; VEGFR antagonists; angiostatic steroids+ heparin; Cartilage-Derived Angiogenesis Inhibitory Factor; matrix metalloproteinase inhibitors; 2-methoxyestradiol; tecogalan; thrombospondin; prolactin; $\alpha V\beta 3$ inhibitors; and linomide.

2. Chemotherapy

A wide variety of chemotherapeutic agents may be used in accordance with the present invention. The term "chemotherapy" refers to the use of drugs to treat cancer or other hyperproliferative diseases. A "chemotherapeutic agent" is used to connote a compound or composition that is administered in the treatment of cancer or other hyperproliferative disease. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

a. Alkylating Agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (cytoxan), dacarbazine, ifosfamide, mechlorethamine (mustargen), and melphalan. Troglitazone can be used to treat cancer in combination with any one or more of these alkylating agents.

b. Antimetabolites

Antimetabolites disrupt DNA and RNA synthesis. Unlike alkylating agents, they specifically influence the cell cycle during S phase. They have been used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate.

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

c. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (Adriamycin), and idarubicin, some of which are discussed in more detail below. Widely used in clinical setting for the treatment of neoplasms, these compounds are administered through bolus injections intravenously at doses ranging from 25-75 m g/m$^2$ at 21 day intervals for adriamycin, to 35-100 mg/m$^2$ for etoposide intravenously or orally.

d. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, taxol, taxotere, vinblastine, vincristine, and vinorelbine.

e. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

3. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of $\gamma$-rays, X-rays, and/or the directed delivery of radioisotopes to tumor cells. Other forms of DNA damaging factors are also contemplated such as microwaves, proton beam irradiation (U.S. Pat. Nos. 5,760,395 and 4,870,287) and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. Radiotherapy may comprise the use of radiolabeled antibodies to deliver doses of radiation directly to the cancer site (radioimmunotherapy). Once injected into the body, the antibodies actively seek out the cancer cells, which are destroyed by the cell-killing (cytotoxic) action of the radiation. This approach can minimize the risk of radiation damage to healthy cells.

4. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a target cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a target cell target. Various effector cells include cytotoxic T cells and NK cells.

In one aspect of immunotherapy, the tumor or disease cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, gamma-IFN, and chemokines such as MIP-1, MCP-1, IL-8 and growth factors such as FLT3 ligand. Antibodies against any of these compounds can be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739,169; Hui and Hashimoto, 1998; Christodoulides et al., 1998), cytokine therapy, e.g., interferons α, β and γ; IL-1, GM-CSF and TNF (Bukowski et al., 1998; Davidson et al., 1998; Hellstrand et al., 1998) gene therapy e.g., TNF, IL-1, IL-2, p53 (Qin et al., 1998; Austin-Ward and Villaseca, 1998; U.S. Pat. Nos. 5,830,880 and 5,846,945) and monoclonal antibodies e.g., anti-ganglioside GM2, anti-HER-2, anti-p185; Pietras et al., 1998; Hanibuchi et al., 1998; U.S. Pat. No. 5,824,311). A non-limiting list of several known anti-cancer immunotherapeutic agents and their targets includes, but is not limited to (Generic Name (Target)) Cetuximab (EGFR), Panitumumab (EGFR), Trastuzumab (erbB2 receptor), Bevacizumab (VEGF), Alemtuzumab (CD52), Gemtuzumab ozogamicin (CD33), Rituximab (CD20), Tositumomab (CD20), Matuzumab (EGFR), Ibritumomab tiuxetan (CD20), Tositumomab (CD20), HuPAM4 (MUC1), MORAb-009 (Mesothelin), G250 (carbonic anhydrase IX), mAb 8H9 (8H9 antigen), M195 (CD33), Ipilimumab (CTLA4), HuLuc63 (CS1), Alemtuzumab (CD53), Epratuzumab (CD22), BC8 (CD45), HuJ591 (Prostate specific membrane antigen), hA20 (CD20), Lexatumumab (TRAIL receptor-2), Pertuzumab (HER-2 receptor), Mik-beta-1 (IL-2R), RAV12 (RAAG12), SGN-30 (CD30), AME-133v (CD20), HeFi-1 (CD30), BMS-663513 (CD137), Volociximab (anti-α5β1 integrin), GC1008 (TGFβ), HCD122 (CD40), Siplizumab (CD2), MORAb-003 (Folate receptor alpha), CNTO 328 (IL-6), MDX-060 (CD30), Ofatumumab (CD20), or SGN-33 (CD33). It is contemplated that one or more of these therapies may be employed with the miRNA therapies described herein.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

5. Gene Therapy

In yet another embodiment, a combination treatment involves gene therapy in which a therapeutic polynucleotide is administered before, after, or at the same time as one or more therapeutic miRNA. Delivery of a therapeutic polypeptide or encoding nucleic acid in conjunction with a miRNA may have a combined therapeutic effect on target tissues. A variety of proteins are encompassed within the invention, some of which are described below. Various genes that may be targeted for gene therapy of some form in combination with the present invention include, but are not limited to inducers of cellular proliferation, inhibitors of cellular proliferation, regulators of programmed cell death, cytokines and other therapeutic nucleic acids or nucleic acid that encode therapeutic proteins.

The tumor suppressor oncogenes function to inhibit excessive cellular proliferation. The inactivation of these genes destroys their inhibitory activity, resulting in unregulated proliferation. The tumor suppressors (e.g., therapeutic polypeptides) p53, FHIT, p16 and C-CAM can be employed.

Other genes that may be employed according to the present invention include Rb, APC, DCC, NF-1, NF-2, WT-1, MEN-I, MEN-II, zac1, p'73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

6. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Also, as described herein, inventive therapies can be used in conjunction with surgeries to the eye.

7. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

This application incorporates U.S. application Ser. No. 11/349,727 filed on Feb. 8, 2006 claiming priority to U.S. Provisional Application Ser. No. 60/650,807 filed Feb. 8, 2005 herein by references in its entirety.

V. Evaluation of Mirna Levels

It is contemplated that a number of assays could be employed to analyze miRNAs, their activities, and their effects. Such assays include, but are not limited to, array hybridization, solution hybridization, nucleic acid amplification, polymerase chain reaction, quantitative PCR, RT-PCR, in situ hybridization, Northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and/or Oligo Ligation Assay (OLA), hybridization, and array analysis. U.S. patent application Ser. No. 11/141,707, filed May 31, 2005; Ser. No. 11/857,948, filed Sep. 19, 2007; Ser. No. 11/273,640, filed Nov. 14, 2005 and provisional patent application 60/869,295, filed Dec. 8, 2006 are incorporated by reference in their entirety.

A. Sample Preparation

While endogenous miRNA is contemplated for use with compositions and methods of the invention, recombinant or synthetic miRNA—including nucleic acids that are complementary or identical to endogenous miRNA or precursor miRNA—can also be handled and analyzed as described herein. Samples may be biological samples, in which case, they can be from lavage, biopsy, fine needle aspirates, exfoliates, blood, sputum, tissue, organs, semen, saliva, tears, urine, cerebrospinal fluid, body fluids, hair follicles, skin, or any sample containing or constituting biological cells. In certain embodiments, samples may be, but are not limited to, fresh, frozen, fixed, formalin-fixed, preserved, RNAlater-preserved, paraffin-embedded, or formalin-fixed and paraffin-embedded. Alternatively, the sample may not be a biological sample, but be a chemical mixture, such as a cell-free reaction mixture (which may contain one or more biological enzymes).

B. Differential Expression Analyses

Methods of the invention can be used to detect differences in miRNA expression or levels between two samples, or a sample and a reference (e.g., a tissue reference or a digital reference representative of a non-cancerous state). Specifically contemplated applications include identifying and/or quantifying differences between miRNA from a sample that is normal and from a sample that is not normal, between a cancerous condition and a non-cancerous condition, between two differently treated samples (e.g., a pretreatment versus a posttreatment sample) or between samples having differing prognosis. Also, miRNA may be compared between a sample believed to be susceptible to a particular therapy or disease and one believed to be not susceptible or resistant to that therapy or disease. A sample that is not normal is one exhibiting phenotypic trait(s) of a disease or condition or one believed to be not normal with respect to that disease or condition. It may be compared to a cell and/or tissue that is normal with respect to that disease or condition. Phenotypic traits include symptoms of a disease or condition of which a component is or may or may not be genetic or caused by a neovascular and/or angiogenic condition. It is specifically contemplated that the invention can be used to evaluate differences between stages of a disease.

Phenotypic traits also include characteristics such as longevity, morbidity, susceptibility or receptivity to particular drugs or therapeutic treatments (drug efficacy), and risk of drug toxicity.

In certain embodiments, miRNA profiles may be generated to evaluate and correlate those profiles with pharmacokinetics. For example, miRNA profiles may be created and evaluated for patient samples prior to the patient's being treated or during treatment to determine if there are miRNAs whose expression correlates with the outcome of treatment. Identification of differential miRNAs can lead to a diagnostic assay that can be used to evaluate samples to determine what drug regimen the patient should be provided. In addition, it can be used to identify or select patients suitable for a particular clinical trial. If a miRNA profile is determined to be correlated with drug efficacy or drug toxicity that may be relevant to whether that patient is an appropriate patient for receiving the drug or for a particular dosage of the drug.

A diagnostic assay can be created based on the profiles that doctors can use to identify individuals with a disease or who are at risk to develop a disease. Alternatively, treatments can be designed based on miRNA profiling.

C. Amplification

Many methods exist for evaluating miRNA levels by amplifying all or part of miRNA nucleic acid sequences such as mature miRNAs, precursor miRNAs, and primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method may be used, such as reverse transcription followed by real time PCR (Chen et al., 2005 and/or U.S. patent application Ser. No. 11/567,082, filed Dec. 5, 2006, which are incorporated herein by reference in their entirety).

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length. In additional embodiments, a primer is at least 35 nucleotides in length.

In a further aspect, a forward primer can comprise at least one sequence that anneals to a target miRNA and alternatively can comprise an additional 5' noncomplementary region. In another aspect, a reverse primer can be designed to anneal to the complement of a reverse transcribed miRNA. The reverse primer may be independent of the miRNA sequence, and multiple miRNAs may be amplified using the same reverse primer. Alternatively, a reverse primer may be specific for a miRNA.

In some embodiments, two or more miRNAs or nucleic acids are amplified in a single reaction volume or multiple reaction volumes. In certain aspects, one or more miRNA or nucleic may be used as a normalization control or a reference nucleic acid for normalization. Normalization may be performed in separate or the same reaction volumes as other amplification reactions. One aspect includes multiplex q-PCR, such as qRT-PCR, which enables simultaneous amplification and quantification of at least one miRNA of interest and at least one reference nucleic acid in one reaction volume by using more than one pair of primers and/or more than one probe. The primer pairs comprise at least one amplification primer that uniquely binds each nucleic acid, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

A single combined reaction for q-PCR, may be used to: (1) decrease risk of experimenter error, (2) reduce assay-to-assay variability, (3) decrease risk of target or product contamination, and (4) increase assay speed. The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619, each incorporated herein by reference in its entirety). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341, each incorporated herein by reference in its entirety).

To assess the expression of microRNAs, real-time RT-PCR detection can be used to screen nucleic acids or RNA isolated from samples of interest and a related reference such as normal adjacent tissue (NAT) samples.

A panel of amplification targets is chosen for real-time RT-PCR quantification. The selection of the panel or targets can be based on the results of microarray expression analyses, such as mirVana™ miRNA Bioarray V1, Ambion. In one aspect, the panel of targets includes one or more miRNA described herein. One example of a normalization target is 5S rRNA and others can be included. Reverse transcription (RT) reaction components are typically assembled on ice prior to the addition of RNA template. Total RNA template is added and mixed. RT reactions are incubated in an appropriate PCR System at an appropriate temperature (15-70° C., including all values and ranges there between) for an appropriate time, 15 to 30 minutes or longer, then at a temperature of 35 to 42 to 50° C. for 10 to 30 to 60 minutes, and then at 80 to 85 to 95° C. for 5 minutes, then placed on wet ice. Reverse Transcription reaction components typically include nuclease-free water, reverse transcription buffer, dNTP mix, RT Primer, RNase Inhibitor, Reverse Transcriptase, and RNA.

PCR reaction components are typically assembled on ice prior to the addition of the cDNA from the RT reactions. Following assembly of the PCR reaction components a portion of the RT reaction is transferred to the PCR mix. PCR reaction are then typically incubated in an PCR system at an elevated temperature (e.g., 95° C.) for 1 minute or so, then for a number of cycles of denaturing, annealing, and extension (e.g., 40 cycles of 95° C. for 5 seconds and 60° C. for 30 seconds). Results can be analyzed, for example, with SDS V2.3 (Applied Biosystems). Real-time PCR components typically include Nuclease-free water, $MgCl_2$, PCR Buffer, dNTP mix, one or more primers, DNA Polymerase, cDNA from RT reaction and one or more detectable label.

Software tools such as NormFinder (Andersen et al., 2004) are used to determine targets for normalization with the targets of interest and tissue sample set. For normalization of the real-time RT-PCR results, the cycle threshold (CO value (a log value) for the microRNA of interest is subtracted from the geometric mean $C_t$ value of normalization targets. Fold change can be determined by subtracting the $dC_t$ normal reference (N) from the corresponding $dC_t$ sample being evaluated (T), producing a $ddC_t$(T-N) value for each sample. The average $ddC_t$(T-N) value across all samples is converted to fold change by $2^{ddCt}$. The representative p-values are determined by a two-tailed paired Student's t-test from the $dC_t$ values of sample and normal reference.

D. Nucleic Acid Arrays

Certain aspects of the present invention concern the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference. Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

E. Hybridization

After an array or a set of miRNA probes is prepared and the miRNA in the sample is labeled, the population of target nucleic acids is contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

VI. Kits

Any of the compositions or components described herein may be comprised in a kit. In a non-limiting example, reagents for isolating miRNA, labeling miRNA, and/or evaluating a miRNA population using an array, nucleic acid amplification, and/or hybridization can be included in a kit, as well reagents for preparation of samples from A subject. The kit may further include reagents for creating or synthesizing miRNA probes or therapeutics. The kits will thus typically comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, magnetic beads, and the like, and/or reagents for coupling any probes and/or target nucleic acids. It may also include one or more buffers, such as pharmaceutical buffer, reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits for implementing methods of the invention described herein are specifically contemplated. In some embodiments, there are kits for preparing miRNA for multi-labeling and kits for preparing miRNA probes and/or miRNA arrays. In these embodiments, kit comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits of the invention include an array containing miRNA probes, as described in the application. An array may have probes corresponding to all known miRNAs of an organism or a particular tissue or organ in particular conditions, or to a subset of such probes. The subset of probes on arrays of the invention may be or include those identified as relevant to a particular diagnostic, therapeutic, or prognostic application. For example, the array may contain one or more probes that is indicative or suggestive of (1) a disease or condition (neovascularization or aberrant angiogenesis), (2) susceptibility or resistance to a particular drug or treatment; (3) susceptibility to toxicity from a drug or substance; (4) the stage of development or severity of a disease or condition (one aspect of prognosis); (5) the likelihood of recurrence (one aspect of prognosis) and (6) genetic predisposition to a disease or condition.

For any kit embodiment, including an array, there can be nucleic acid molecules that contain or can be used to amplify a sequence that is a variant of, identical to or complementary to all or part of any of SEQ ID NOs described herein. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquotted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent or buffer. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNase-free or protect against RNases. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits of the invention. Such kits, however, are not limited to the particular items identified above and may include any reagent used for the manipulation or characterization of miRNA.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1 miRNAs Altered During Ischemic Retinopathy-Induced Neovascularization

To examine miRNA expression during retinal neovascularization, the inventors used a murine model of oxygen-induced, ischemic retinopathy that results in reproducible, proliferative retinal neovascularization (Smith et al., 1994.). C57BL/6J mice were placed in 75% oxygen on postnatal day 7 and returned to room air on postnatal day 12. On postnatal day 15, mice were euthanized, eyes were removed, and retinas dissected. Small RNAs were isolated from retinas using the mirVana™ miRNA Isolation Kit (cat. no. AM1561; Ambion Inc., Austin, Tex., USA) according to the manufacturer's instructions. Small RNAs (5 µg), pooled from ten ischemic retinas or from ten age-matched control retinas, were identified and quantified by microarray analysis. Microarray hybridizations were performed by LC Sciences (Houston, Tex., USA). Small RNAs from ischemic retinas were labeled with Cy3 and small RNAs from control retinas were labeled with Cy5 and hybridized to an array of murine microRNA (mmu-miR) probes with six redundant complementary sequences for each of the mmu-miR transcripts in the Sanger miRBase Release 7.0 (August 2005) (Griffiths-Jones et al., 2006). Red and green fluorescence intensities were determined for each probe. Statistical comparisons were made between the mean differences in intensity for the probes and the intensity differences for control probes. A p value of <0.01 was used to identify differentially expressed microRNAs (Table 1). Ten miRNAs (mmu-miR-451, -214, -424, -199a, -146, -106a, -350, -21, -218, and -148b) had increased expression during neovascularization of ischemic retinas, and six (mmu-miR-451, -214, -424, -199a, -146, and -106a) were increased more than two-fold. Nine miRNAs (mmu-miR-184, -31, -150, -409, -375, -129-5p, -124a, -29a, and -129-3p) had significantly reduced expression during neovascularization of ischemic retinas, and three (mmu-miR-184, -31, and -150) were decreased more than two-fold.

The miRNAs in Table 1 represent particularly useful therapeutic targets for treating conditions associated with vascularization

TABLE 1

MicroRNAs Differentially Expressed During Neovascularization of Mouse Retinas. Log ratio, the log(2) normalized signal for miRNA from ischemic mice divided by the log(2) normalized signal for miRNA from control mice. Positive log ratio values indicate miRNAs with increased levels during neovascularization. Negative log ratio values indicate miRNAs with decreased levels during neovascularization.

| miRNA | Log Ratio (ischemia/control) |
|---|---|
| miR-451 | 2.31 |
| miR-214 | 2.08 |
| miR-424 | 2.01 |
| miR-199a | 1.52 |
| miR-146 | 1.50 |
| miR-106a | 1.25 |
| miR-350 | 0.95 |
| miR-21 | 0.91 |
| miR-218 | 0.83 |
| miR-148b | 0.80 |
| miR-184 | −3.50 |
| miR-31 | −2.50 |
| miR-150 | −2.01 |
| miR-409 | −0.81 |
| miR-375 | −0.80 |
| miR-129-5p | −0.75 |
| miR-124a | −0.65 |
| miR-29a | −0.63 |
| miR-129-3p | −0.61 |

Example 2

Quantification of miRNAs Altered During Neovascularization by QRT-PCR

The inventors validated microarray data for specific miRNAs identified in Example 1. Using small RNAs isolated from retinas as described in Example 1 above, the inventors measured miRNA levels by qRT-PCR as previously described (Raymond et al., 2005), with minor modifications. Briefly, small RNAs were reverse-transcribed with SuperScript™ III Reverse Transcriptase (Invitrogen Corp.; Carlsbad, Calif., USA) into cDNAs, using either (1) microRNA-specific primers containing a 36 bp 5' tail from C. elegans genomic sequence or (2) random hexamer-priming. For miRNA amplifications, a miRNA-specific, 16-nucleotide upstream primer and a 19-nucleotide universal primer complementary to the C. elegans tail sequence were used. For standardization, a fragment of 5S rRNA was amplified and quantified. Amplifications were performed in a LightCycler® (Roche Diagnostics Corp., Indianapolis, Ind., USA) using the LightCycler® FastStart DNA Master SYBR Green I reaction mix (Roche). For negative controls, cDNA generated from random hexamer priming was used. The mean threshold cycle numbers ($\Delta CT$) for mmu-miR-31, -150, and -184 amplified from ischemic and control retinas (n=5 for each) were determined, and the mean differences between the two values ($\Delta\Delta CT$) were calculated. $\Delta\Delta CT$ values ranged from about −1.0 (miR-31) to −2.5 (miR-150) (FIG. 1A). Statistical comparisons confirmed that each of the miRs were significantly reduced in ischemic compared to control retinas (FIG. 1B).

Example 3

Predicted Gene Targets of mmu-miR-184, mmu-miR-31, and mmu-miR-150

The inventors searched selected mRNA transcripts for sequences that might represent target binding sites for the microRNAs shown in Table 1 above. Searches were performed in the 5'- and 3'-untranslated regions (UTR) from a group of genes encoding angiogenic factors and their receptors (VEGF, HGF, FGF-2, P1GF, IGF-1, TGF-beta, PDGF-A, PDGF-B, VG5q, Delta-like 4, SEMA3a, Sema3F, Notch4, EphA2, Roundabout, HIF-1alpha, Frizzed-4, SDF-1, PEDF, endostatin, vasohibin-1, thrombspodin-1, Ang-1, Ang-2, Flt-1, KDR, neuropilin-1, neuropilin-2, CXCR4, Tie1, Tie2, angiostatin). UTR sequences were obtained from the *Mus musculus* genome sequence at the Ensembl Project (Birney et al., 2004) (at the World Wide Web address ensembl.org/index.html) and were searched for possible microRNA target sites using several target site prediction systems, including miRBase Targets (at World Wide Web address microrna.sanger.ac.uk/targets/v4/), the miRanda algorithm (John et al., 2005; Betel et al., 2008) (at the World Wide Web address microrna.org), RNAhybrid (Rehmsmeier et al., 2004) (at the internet address bibiserv.techfak.uni-bielefeld.de/rnahybrid), and PicTar (Krek et al., 2005) (at internet address pictar.bio.nyu.edu). Previously reported criteria (Lewis et al., 2005; Sethupathy et al., 2006) for predicting microRNA targets were used as a guide and included (1) a conserved seed match, i.e., perfect Watson-Crick complementarity between nucleotides 2-7 of the microRNA and a 6 nucleotide section of the 3'-UTR of the mRNA that occurs at corresponding positions for multiple species, (2) a conserved anchoring A, which is an A nucleotide on the 3'-UTR just downstream of the seed match that also occurs in the UTRs of the genes from multiple species, and (3) a conserved m8-t8 match, which is an A:U or G:C match between the eighth nucleotide of the microRNA and the corresponding position in the 3'-UTR in multiple species. Conservation analyses between the mouse UTRs and corresponding UTRs for humans, rats, and dogs were performed using applications at the University of Santa Cruz Genome Bioinformatics internet site, on the World Wide Web at genome.ucsc.edu.

The inventors identified possible gene targets for mmu-miR-31, -150, and -184 (FIG. 2). Predicted target sequences for mmu-miR-31 were identified in Pdgfb, Hif1α, and Frizzled4. Predicted target sequences for mmu-miR-150 were identified in Vegf, Pdgfb, Pdgfa, and Notch4. Predicted target sequences for mmu-miR-184 were identified in Frizzled4. No predicted target genes were identified for up-regulated miRNAs in Table 1.

The predicted gene targets of mmu-miR-31, -150, and -184 represent particularly useful therapeutic targets for treating conditions associated with vascularization, through manipulation of their expression levels.

Example 4

Verification of miRNA Target Genes

The inventors utilized luciferase gene reporter assays to assess the validity of putative miRNA target regulatory sequences in Pdgfb, Frizzled4, Hif1α, Vegf, and Notch4. Putative miRNA target sequences were amplified by PCR using retinal cDNA as template and amplification primers that included restriction sites for SpeI and HindIII. PCR products were cloned into a TOPO TA Cloning® vector (Invitrogen). Recombinant plasmid inserts (miRNA target sequences) were verified by DNA sequencing. For validation of miRNA target sequences in Pdgfb, Frizzled4, Hif1α, and Notch4, the cloned target sequences were excised and subcloned into a luciferase microRNA expression reporter vector (pMIR-REPORT™, Ambion). For validation of miRNA target sequences in Vegf, the inventors used a pGL2-CMV vector containing a 1.7 kb mouse Vegf 3'-UTR coupled to a luciferase gene (R. C. Nichols, Department of Microbiology and Immunology, Dartmouth School of Medicine, Hanover, N.H.).

Luciferase reporter assays were conducted in human retinal pigment epithelial cells (ARPE-19; American Type Culture Collection, Manassas, Va., USA) cultured in DMEM/F12 medium (HyClone; Logan, Utah, USA) supplemented with 10% fetal bovine serum. After reaching 70% confluence, cells were co-transfected with a synthetic microRNA (mmu-miR-31, -150, or -184; pre-miR™ miRNA Precursor Molecule; Ambion) (25 nmol), 1 µg of reporter vector (pMIR-REPORT™ or pGL2-CMV) containing one of the possible target 3'-UTRs, and 2.5 ng of Renilla luciferase vector (Promega Corp.; Madison, Wis., USA). For negative controls, ARPE-19 cells were co-transfected with a scrambled synthetic microRNA (25 nmol), 1 µg of reporter vector containing one of the possible target 3'-UTRs, and 2.5 ng of Renilla luciferase vector. After 48 hours, cells were harvested and luciferase expression assays were performed using the Dual-Luciferase® Reporter Assay System (Promega). Luciferase expression assays were performed in triplicate for each miRNA/target 3'-UTR combination. Statistical comparisons with negative control assays were made by paired t-test.

Figures 3A, 3B, 3C, 3D, 3E, 3F:
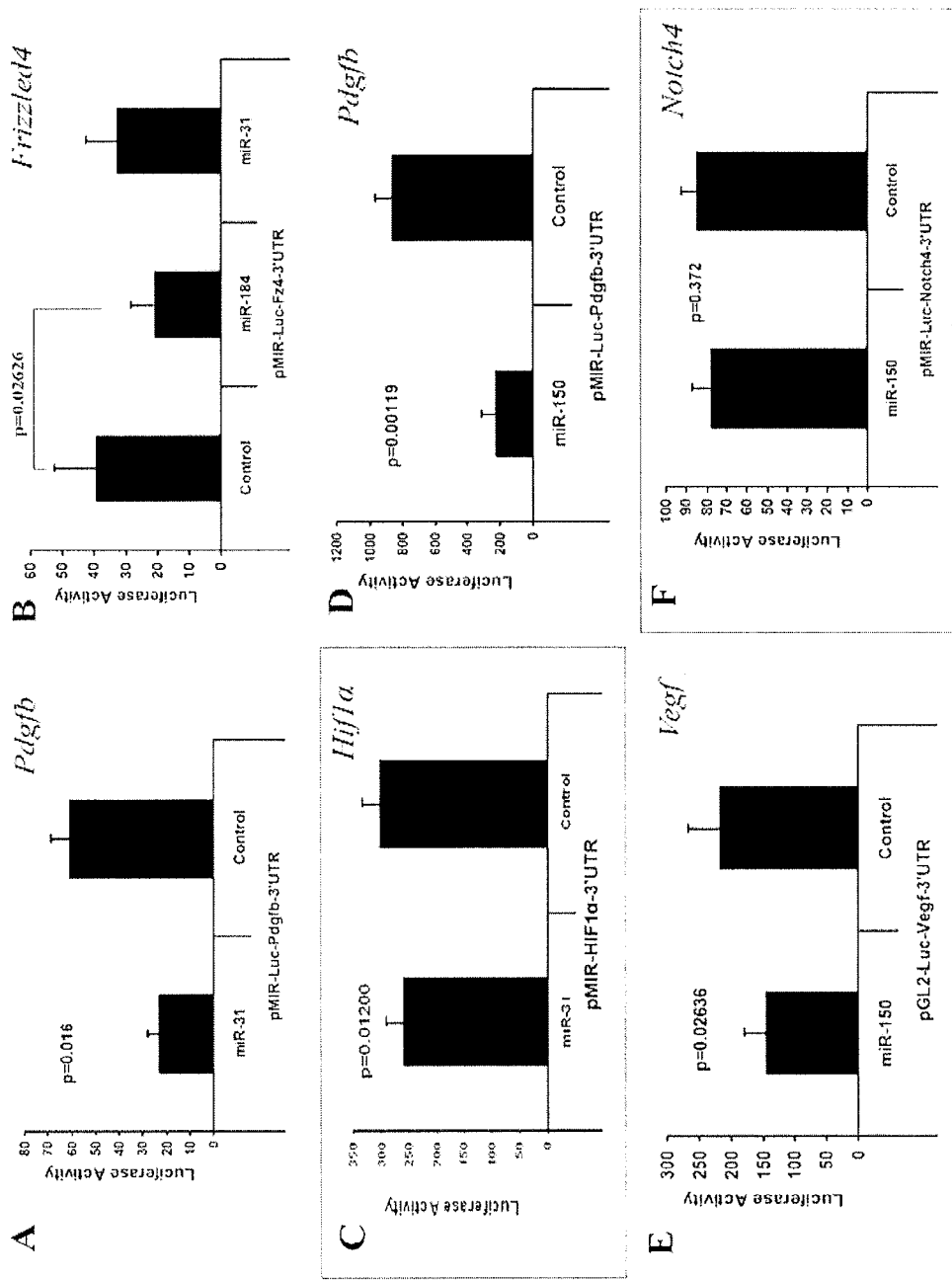
FIGS. 3A-3F. Effect of different microRNAs on luciferase activity from reporter genes harboring putative miRNA binding sites. Luciferase reporter assays were performed as described in Example 4. Each bar represents the mean luciferase activity (±standard error of mean) calculated from three experiments. pMIR-Luc-Pdgfb-3'UTR (FIGS. 3A and 3D); pMIR luciferase reporter vector containing 3'-UTR from Pdgfb. pMIR-Luc-HIF1$\alpha$-3'UTR (FIG. 3C); pMIR luciferase reporter vector containing 3'-UTR from Hif1$\alpha$. pMIR-Luc-Fz4-3'UTR (FIG. 3B); pMIR luciferase reporter vector containing 3'-UTR from Frizzled4. pGL2-Luc-Vegf-3'UTR (FIG. 3E); pGL2-CMV luciferase reporter vector containing 3'-UTR from Vegf. pMIR-Luc-Notch4-3'UTR (FIG. 3F); pMIR luciferase reporter vector containing 3'-UTR from Notch4.

Co-transfection of ARPE-19 cells with synthetic mmu-miR-31 and a pMIR vector with the Pdgfb or Hif1α 3'-UTR, significantly reduced luciferase levels expressed by the reporter (FIG. 3A, 3C), verifying that Pdgfb and Hif1α are targets for regulation by mmu-miR-31. Co-transfection with synthetic mmu-miR-31 and a pMIR vector with the Frizzled4 3'-UTR had no effect on luciferase levels from the reporter (FIG. 3B).

Co-transfection or ARPE-19 cells with synthetic mmu-miR-150 and a pMIR vector with the Pdgfb 3'-UTR or with synthetic mmu-miR-150 and a pGL2-CMV vector with the Vegf 3'-UTR, significantly reduced luciferase levels expressed by the reporter (FIG. 3D, 3E), verifying that Pdgfb and Vegf are targets for regulation by mmu-miR-150. Co-transfection with synthetic mmu-miR-150 and a pMIR vector with the Notch4 3'-UTR had no effect on luciferase levels from the reporter (FIG. 3F).

Co-transfection or ARPE-19 cells with synthetic mmu-miR-184 and a pMIR vector with the Frizzled4 3'-UTR significantly reduced luciferase levels expressed by the reporter (FIG. 3B), verifying that Frizzled4 is a target for regulation by mmu-miR-184.

Example 5

Effect of miRNAs on Target Gene Product Levels in Neovascularizing Retinas In Vivo The inventors evaluated the effects of mmu-miR-31, -250, and -184 on target gene product levels in vivo, during retinal neovascularization induced by ischemic retinopathy. C57/BL6 mice were placed in 75% oxygen on postnatal day 7. On postnatal day 12, mice were returned to room air and given an intraocular injection of a synthetic experimental microRNA (0.005 μmol in 1 μl) (pre-miR™ miRNA Precursor Molecule; Ambion) in one eye and a synthetic control microRNA (0.005 μmol in 1 μl; scrambled microRNA sequence) in the other eye. Synthetic miRNAs were injected with a Harvard Pump Microinjection System (Harvard Apparatus, Holliston, Mass., USA) and pulled glass micropipettes as previously described (Mori et al., 2001). Mice were euthanized at postnatal day 15, eyes were removed, and retinas were dissected and homogenized. Retinas were placed in 200 μl of lysis buffer (50 μl 1M Tris-HCl (pH 7.4), 50 μl of 10% sodium dodecyl sulfate, 5 μl of 100 nM phenylmethanesulfonyl, and 5 ml of sterilized, de-ionized water), homogenized, sonicated at 4° C. for 5 seconds, and centrifuged at 10,000 g for 5 minutes at 4° C. The protein concentration of the supernatants was measured with a bicinchoninic acid protein assay kit (Pierce; Rockford, Ill., USA). Retinal homogenates were used to assess HIF-1α, PDGF-B, and Frizzled 4 by immunoblot analysis and VEGF by both immunoblot analysis and ELISA. For immunoblots, 20 μg of protein were separated by SDS-PAGE on 8-12% acrylamide gels and transferred to a nitrocellulose membrane. Non-specific binding was blocked by incubation in Tris-buffered saline (TBS) containing 5% skim milk, and membranes were hybridized with 0.5 μg/ml rabbit anti-mouse VEGF polyclonal antibody (Abcam Inc.; Cambridge, Mass., USA), rabbit anti-mouse Frizzled 4 antibody (R&D Systems Inc.; Minneapolis, Minn., USA), rabbit anti-mouse PDGF-B or HIF1-α antibody (Santa Cruz Biotechnology® Inc.; Santa Cruz, Calif., USA), or in TBS containing 0.05% Tween 20 and 2.5% skim milk, at 4° C. overnight. After three washes with TBS-Tween-20, the membrane was incubated in horseradish peroxidase (HRP)-conjugated goat anti-rabbit polyclonal antibody (1:5000) (GE Healthcare Bio-Sciences Corp.; Piscataway, N.J., USA). For signal development, membranes were incubated in ECL Plus™ Western Blotting Detection Reagent (GE Healthcare Bio-Sciences) and exposed to X-ray film. ELISAs were performed using a Quantikine VEGF assay kit (R&D Systems Inc.) according to the manufacturer's instructions. Serial dilutions of recombinant VEGF were assayed to generate a standard curve. The limit of detection was 125 pg/ml of VEGF.

Figures 4A, 4B:
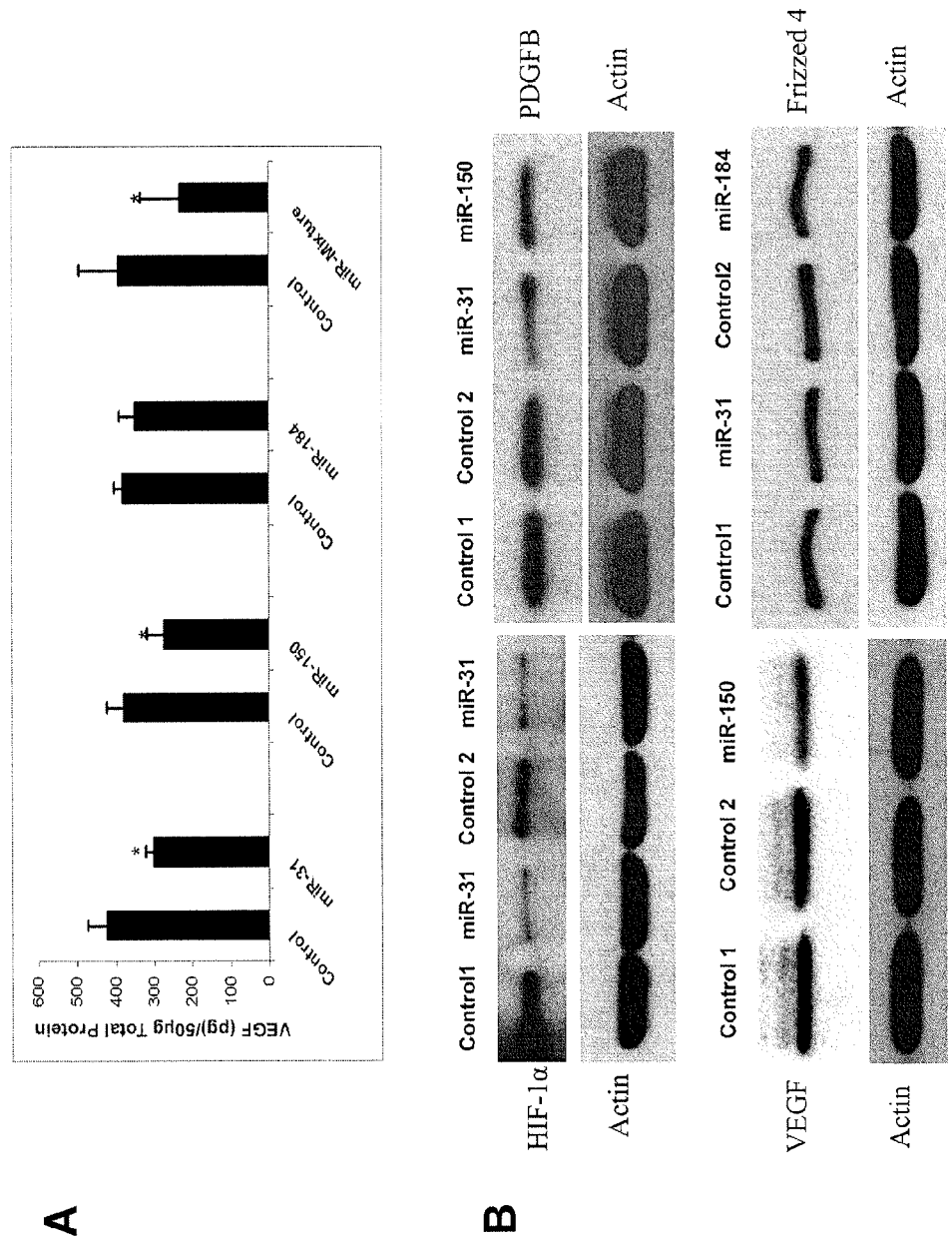
FIGS. 4A-4B. Effect of microRNAs on target gene product levels in neovascularizing retinas in vivo.

Injection of synthetic mmu-miR-31 or -150, but not synthetic mmu-miR-184, caused a significant reduction in VEGF levels in homogenates of neovascularizing retinas (FIG. 4A, FIG. 4B). Since mmu-miR-31 does not target Vegf directly, it is likely that its effect occurs indirectly through one of its actual targets, probably Hif1α. Injection of 1 μl containing 1.66 pmol each of the three synthetic microRNAs also caused a significant reduction in VEGF (FIG. 4A). Intraocular injection of synthetic mmu-miR-31 caused reductions in retinal HIF1-c' and PDGF-B (FIG. 4B). Injection of synthetic mmu-miR-150 caused reductions in PDGF-B and VEGF (FIG. 4B). Injections of synthetic mmu-miR-31 or synthetic mmu-miR-184 failed to cause reductions in Frizzled 4 protein in the retinas (FIG. 4B).

Example 6 miRNA Therapy in Mice with Oxygen-Induced Ischemic Retinopathy

Ischemic retinopathy was generated in mice as described above in Example 1. Mice were returned to room air at postnatal day 12 and given a 1 μl intraocular injection containing 2 μg of experimental synthetic microRNA in one eye or 2 μg of control synthetic microRNA in the other eye. Injections were given as described above in Example 5. On postnatal day 17, areas of neovascularization on the surfaces of the mouse retinas were measured as previously described (Lima e Silva et al., 2007). Briefly, mice were given an intraocular injection of 1 μl of rat anti-mouse PECAM-1 antibody (BD Biosciences; San Jose, Calif., USA) and were euthanized twelve hours after antibody injection. Mouse eyes were dissected and fixed in 10% formalin for 4 hours. Intact retinas were dissected, incubated for 40 minutes in a 1:500 dilution of goat anti-rat IgG conjugated with Alexa488 (Invitrogen), washed, and whole mounted. This technique provides selective staining of retinal neovascularization on the surface of the retina (Shen et al., 2007). An observer, masked with respect to treatment groups, examined the slides by fluorescence microscopy and measured the area of neovascularization per retina using computerized image analysis and Image-Pro® PLUS software (Media Cybernetics, Inc.; Bethesda, Md., USA).

Figures 5A, 5B:
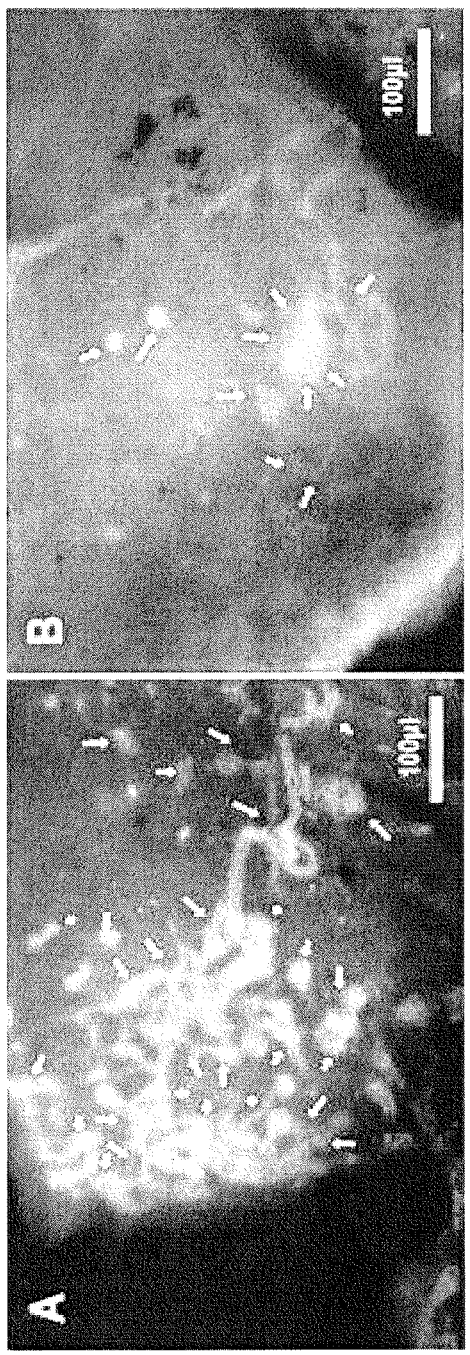
FIGS. 5A-5B. Neovascularization in retinas from mouse eyes following ischemia-induced retinopathy.
Figures 6A, 6B, 6C, 6D:
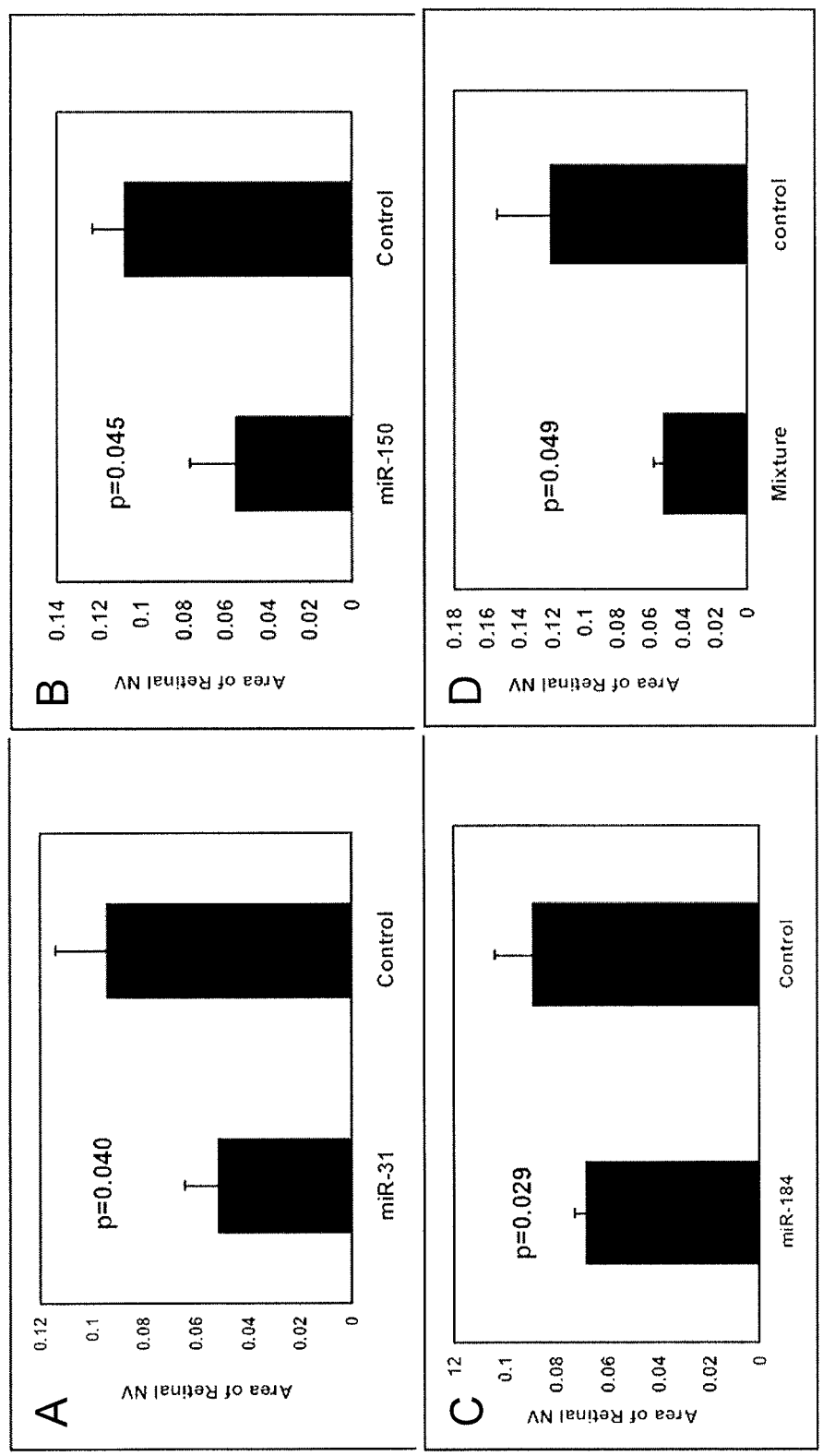
FIGS. 6A-6D. Effect of microRNAs on ischemia-induced retinal neovascularization. Each bar represents the mean area of neovascularization (±standard deviation) calculated from eight mice. Statistical comparisons were made by paired t-test.

Retinas from mouse eyes injected with negative control miRNA showed extensive neovascularization (FIG. 5A). In contrast, retinas from mouse eyes injected with 2 μg of synthetic mmu-miR-31, -150, or -184 showed very little neovascularization on the surface of the retina (FIG. 5B). Computerized image analysis confirmed a significant reduction in mean area of neovascularization per retina in eyes injected with synthetic mmu-miR-31, -150, or -184 (FIG. 6A, FIG. 6B, FIG. 6C) or with a mixture of all three synthetic miRs (FIG. 6D) as compared to eyes injected with negative control miRNA.

Example 7 miRNA Therapy in Mice with Choroidal Neovascularization

The inventors used a model of choroidal neovascularization to further evaluate miRNA therapy. The choroid, also known as the choroidea or choroid coat, is the vascular layer of the eye lying between the retina and the sclera (the fibrous, protective outer layer of the eye). The choroid provides oxygen and nourishment to the outer layers of the retina.

Choroidal neovascularization was generated by modification of a previously described technique (Tobe, et al., 1998). Briefly, 4 to 5 week old female C57BL/6J mice were anesthetized and the pupils were dilated with 1% tropicamide. Three burns of 532 nm diode laser photocoagulation (75 μm spot size, 0.1 second duration, 120 mW) were delivered to each retina using the slit lamp delivery system of an OcuLight GL Photocoagulator (IRIDEX Corp., Mountain View, Calif., USA). Burns were performed in the 9-, 12-, and 3-o'clock positions of the posterior pole of the retina. Immediately after laser treatment and again on day 7, mice were given an intraocular injection of 1 μl containing 5 pmol of experimental synthetic microRNA or a mixture of three experimental synthetic microRNAs (1.67 pmol each mmu-miR-31, -150, and -184) in one eye and 5 pmol of a scrambled, synthetic microRNA (control) in the other eye. Fourteen days after laser treatment, mice were perfused with fluorescein-labeled dextran (2×10$^6$ average MW) (Sigma-Aldrich, St. Louis, Mo., USA), and choroidal whole mounts were prepared and examined by fluorescence microscopy. An observer, masked with respect to treatment group, used image analysis techniques to measure the area of choroidal neovascularization at each Bruch's membrane rupture site (Shen et al., 2006; Lima e Silva et al., 2007). The three choroidal neovascularization areas within each eye were averaged to give one experimental value per eye. Statistical comparisons were made by paired t-test.

Figures 7A, 7B:
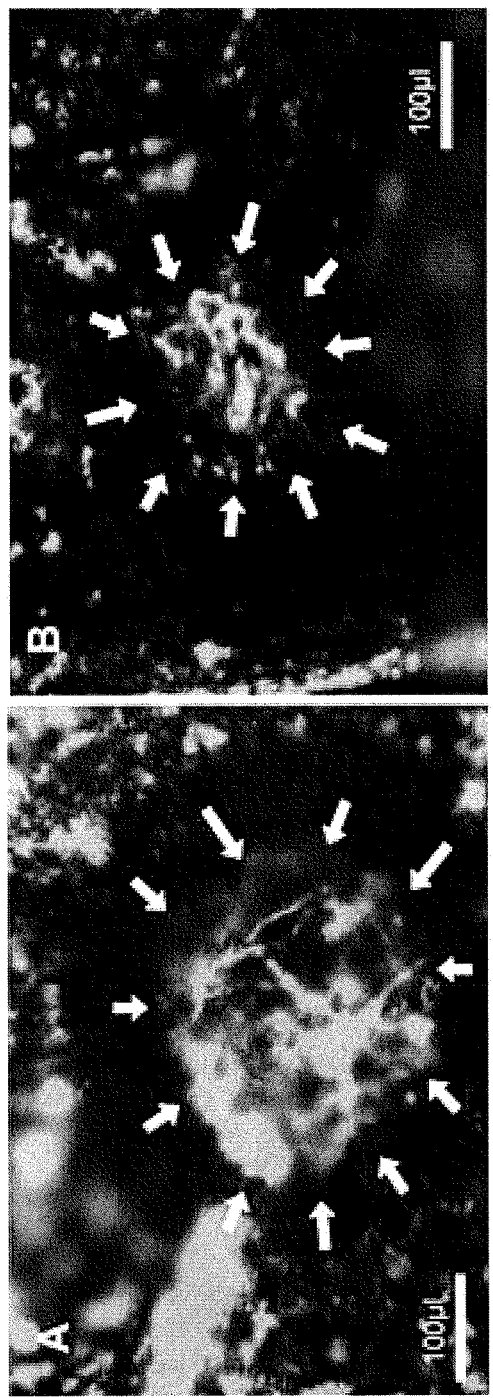
FIGS. 7A-7B. Choroidal neovascularization at Bruch's membrane rupture sites following laser photocoagulation.
Figures 8A, 8B, 8C, 8D:
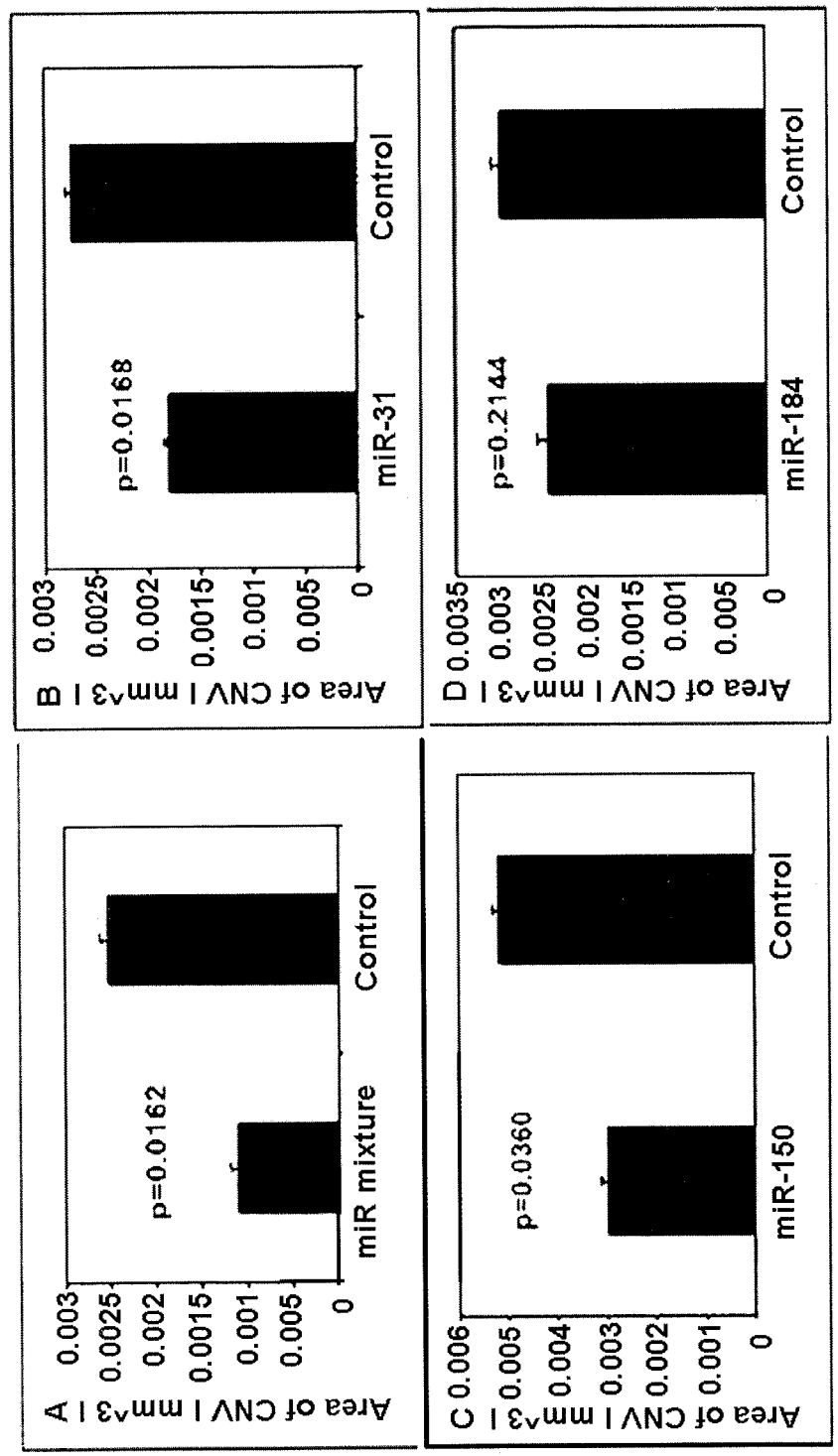
FIGS. 8A-8D. Effect of microRNAs on choroidal neovascularization at Bruch's membrane rupture sites in a mouse model. Each bar represents the mean area of choroidal neovascularization ($mm^3$±standard deviation) calculated from at least twelve experimental values. Statistical comparisons were made by paired t-test.

Fluorescence microscopy observation revealed that eyes treated with a mixture of three experimental miRNAs (mmu-miR-31, -150, and -184) (FIG. 7A) had smaller choroidal neovascularization lesions than fellow eyes treated with the scrambled, control miRNA (FIG. 7B). Measurement of the area of choroidal neovascularization by computerized image analysis revealed that eyes treated with the mixture of experimental miRNAs had a significant reduction in the mean area of choroidal neovascularization at Bruch's membrane rupture sites when compared to eyes treated with the scrambled, control miRNA (FIG. 8A). Mouse eyes treated individually with mmu-miR-31 (FIG. 8B) or mmu-miR-150 (FIG. 8C) also exhibited reduced choroidal neovascularization. Mouse eyes treated with mmu-miR-184 displayed similar levels of choroidal neovascularization as those treated with the control miRNA (FIG. 8D).

Example 8 miRNAs Altered in RD1 Mouse Model of Neovascularization

The inventors examined miRNA expression changes in a second model of neovascularization, consisting of a transgenic mouse strain (RD1) that contains a phosphodiesterase 6B mutation (Chang et al., 2002). RD1 mice exhibit early onset retinal degeneration wherein they undergo rod degeneration between postnatal day 10 (P10) and postnatal day 22 (P22) and cone degeneration between postnatal day 22 (P22) and postnatal day 35 (P35).

To track changes in miRNA expression during the progression of neo-vascularization in eyes of RD1 mice, animals were sacrificed at P5, P10, P15, P22, and P35, eyes were removed, and retinas dissected. Small RNAs were isolated from retinas using the mirVana™ miRNA Isolation Kit (Ambion). To account for changes in miRNA expression during normal mouse development, a set of control mice (strain C57) were sacrificed at P5, P10, P15, P22, and P35, eyes were removed, retinas dissected, and small RNAs were isolated as for the RD1 mice.

miRNAs from all mice were purified using the flashPAGE™ Fractionator Apparatus (cat. no. AM13100, Ambion) and labeled using the mirVana™ miRNA Labeling Kit (cat. no. AM1562, Ambion). Labeled miRNAs were hybridized to mirVana™ miRNA Bioarrays (Ambion). Signals for each miRNA-specific probe were background-subtracted, normalized, and converted to log(2) scale. The normalized expression data for each miRNA at each time point were compared to the corresponding data for the same animals at P10 (the day of retinal degeneration onset).

The inventors observed differential expression of specific miRNAs during retinal neovascularization in RD1 mice as compared to their expression in the control mice (Table 2). Forty-seven miRNAs were observed to be significantly differentially expressed, at one or both of P22 and P35, in the RD1 mice relative to the C57 control mice-mmu-miR-10b, -96, -183, -184, -16, -182, -191, -29c, -181c, -129-3p, -335, -210, -512-3p, -132, -500, -339, -511, -26b, -30b, and -15a and ambi-miR-7026 were all significantly decreased in mouse retinas undergoing neovascularization (Table 2) and mmu-miR-205, -106a, -365, -299-5p, -200a, -351, -329, -122a, -20a, -350, -520 h, -142-5p, -203, -211, -145, -93, -192, -106a, -201, -18a, -17-5p, -106b, and -223, mmu-let-7b, ambi-miR-7079, and ambi-miR-7085, were all significantly increased in mouse retinas undergoing neo-vascularization (Table 2). The miRNAs in Table 2 represent particularly useful therapeutic targets for treating conditions associated with vascularization.

TABLE 2

MicroRNAs Differentially Expressed During Neovascularization of Retinas in RD1 Mice. Positive log ratio values indicate miRNAs with increased levels during neovascularization. Negative log ratio values indicate miRNAs with decreased values during neovascularization. P22; post-natal day 22. P35; post-natal day 35.

| miRNA | Log Ratio RD1-057 (P22) | Log Ratio RD1-057 (P35) |
|---|---|---|
| miR-10b | −2.525 | −2.792 |
| miR-96 | −2.404 | −2.58 |
| miR-183 | −1.726 | −1.938 |
| miR-184 | −2.345 | −1.829 |
| miR-16 | −1.769 | −1.24 |
| miR-182 | −1.983 | −1.171 |
| miR-191 | −1.006 | −1.153 |
| miR-29c | −2.195 | −1.03 |
| miR-181c | −1.096 | −1.017 |
| miR-129-3p | −0.428 | −1.015 |
| miR-335 | −1.005 | −0.967 |
| ambi-miR-7026 | 0.461 | −0.88 |
| miR-210 | −0.672 | −0.862 |
| miR-512-3p | −0.132 | −0.845 |
| miR-132 | −0.229 | −0.832 |
| miR-500 | −0.395 | −0.77 |
| miR-339 | −0.295 | −0.712 |
| miR-511 | −0.124 | −0.695 |
| miR-26b | −1.375 | −0.689 |
| miR-30b | −1.35 | −0.685 |
| miR-15a | −1.01 | −0.601 |
| miR-205 | 2.588 | 2.601 |
| miR-106a | 0.957 | 2.585 |
| miR-365 | 2.332 | 2.359 |
| miR-299-5p | 2.408 | 2.318 |
| ambi-miR-7079 | 2.495 | 2.302 |
| miR-200a | 2.104 | 2.238 |
| miR-351 | 1.956 | 2.083 |
| miR-329 | 0.111 | 1.367 |
| miR-122a | 0.958 | 1.35 |

TABLE 2-continued

MicroRNAs Differentially Expressed During Neovascularization of Retinas in RD1 Mice. Positive log ratio values indicate miRNAs with increased levels during neovascularization. Negative log ratio values indicate miRNAs with decreased values during neovascularization. P22; post-natal day 22. P35; post-natal day 35.

| miRNA | Log Ratio RD1-057 (P22) | Log Ratio RD1-057 (P35) |
|---|---|---|
| miR-20a | 0.755 | 1.266 |
| miR-350 | 0.59 | 1.258 |
| miR-520h | 1.094 | 1.247 |
| miR-142-5p | 0.153 | 1.157 |
| miR-203 | 0.637 | 1.142 |
| miR-211 | 0.593 | 1.093 |
| miR-145 | 0.213 | 1.072 |
| let-7b | 0.364 | 1.06 |
| miR-93 | 0.969 | 1.045 |
| miR-192 | 0.319 | 1.001 |
| miR-106a | 0.83 | 0.929 |
| miR-201 | 0.704 | 0.916 |
| miR-18a | 0.611 | 0.907 |
| miR-17-5p | 0.741 | 0.864 |
| ambi-miR-7085 | 0.667 | 0.848 |
| miR-106b | 0.549 | 0.842 |
| miR-223 | 0.527 | 0.819 |

Example 9

Predicted MicroRNA Targets

The miRNAs that were observed to be significantly differentially expressed in the retinas of mice undergoing neovascularization were evaluated for their capacity to potentially regulate genes associated with angiogenesis. Gene target predictions were performed by searching within the 3'UTRs of 23 angiogenesis-related genes (LRP6, VEGFA, VEFC, VEGF-R, EFEMP1, ECGF1, ELOVL4, EREG, FGF1, FGF2, IGF1, JAG1, NRP1, NRP2, PGF, RS1, RDS, MMP2, MMP9, TIMP1, TIMP2, TIMP3, TLR4) for sites that are perfectly complementary with the core sequences of the selected miRNAs. Predicted targets for miRNAs are shown in Table 3. Many of the miRNAs were predicted to have multiple potential target sites within a single 3'UTR. The number of predicted target interactions is denoted in parentheses. The average number of angiogenesis-related target sites for the neovascularization-associated miRNAs was 4.64, with a range of 0-12. Based on this analysis, it is apparent that the altered expression of one or several of these miRNAs can profoundly influence the expression levels of genes that are known to inhibit or activate blood vessel growth.

TABLE 3

Predicted target genes of miRNAs altered during neovascularization. Genes with multiple predicted target interaction sites have the number of such sites indicated in parentheses following the gene name. Some genes had no targets predicted by the methods described in Example 9.

| miRNA | Predicted Target Genes | | | | | | |
|---|---|---|---|---|---|---|---|
| miR-10b | NRP2 | RS1 | | | | | |
| miR-96 | | | | | | | |
| miR-183 | LRP6 | MMP9 | TIMP3 | NRP1 | | | |
| miR-16/miR-15a | VEGFA | LRP6 | NRP2 (3) | FGF2 (4) | RDS (2) | RS1 | |
| miR-182 | VEGFR | | | | | | |
| miR-191 | TIMP2 | ELOVL4 | RDS | RS1 | | | |
| miR-29c/miR-29a | VEGFA | MMP2 | EREG (2) | IGF1 (2) | ELOVL4 | EFEMP1 | RDS |
| miR-181c | TIMP3 (2) | IGF1 | RDS | | | | |
| miR-129-3p | NRP1 | NRP2 | | | | | |
| miR-335 | FGF2 | RDS (2) | | | | | |
| miR-210 | NRP2 | | | | | | |
| miR-512-3p | TIMP2 | FGF1 | FGF2 | | | | |
| miR-132 | RS1 | | | | | | |
| miR-500 | VEGFR (2) | TIMP2 | NRP1 | NRP2 | FGF2 (2) | ANPEP | |
| miR-339 | VEGFA (2) | MMP2 | NRP2 | CFB | RS1 | | |
| miR-511 | VEGFA | VEGFC | MMP2 | NRP1 (2) | FGF2 | TLR4 (3) | VMD2 | ELOVL4 (2) |
| miR-26b | JAG1 | EREG | IGF1 | TLR4 | EFEMP1 | | |
| miR-30b | TIMP3 | NRP1 | | | | | |
| miR-31 | TIMP2 | IGF1 | TLR4 (2) | | | | |
| miR-150 | VEGFA | NRP1 | FGF1 | FGF2 (2) | EREG | IGF1 | RS1 |
| miR-129-5p | APOE | TIMP2 | NRP1 | JAG1 | FGF2 | ANGPT1 | IGF1 (4) | RDS |
| miR-124a | MMP2 | PGF | NRP1 | NRP2 | JAG1 | | |
| miR-451 | EREG | FBLN5 | | | | | |
| miR-214 | VEGFR | PGF (3) | TIMP3 | NRP1 | JAG1 | CFB | FBLN5 | RDS |
| miR-424 | VEGFA | LRP6 | NRP2 (3) | FGF2 (4) | RDS (2) | RS1 | |
| miR-199a | JAG1 | | | | | | |
| miR-146 | TIMP3 | NRP2 (2) | JAG1 | FGF2 | CFH | TLR4 | |
| miR-106a/20a/17-5p | VEGFA | MMP2 (2) | TIMP2 | FGF2 (2) | EREG | | |
| miR-21 | TIMP3 (2) | JAG1 | FGF1 | FGF2 | CFH | TLR4 | |
| miR-218 | TIMP2 | JAG1 | IGF1 | RDS | | | |
| miR-148b | NRP1 | FGF2 | ANGPT2 | IFG1 | VMD2 | | |
| miR-205 | VEGFA | FGF1 | FGF2 | | | | |
| miR-365 | EREG | TLR4 | EFEMP1 | | | | |
| miR-299-5p | VEGFR | FGF1 | | | | | |
| miR-200a | VEGFR | NRP1 | NRP2 (2) | FBLN5 | | | |
| miR-329 | TIMP3 | NRP2 | TLR4 | | | | |
| miR-122a | TLR4 | RS1 | | | | | |
| miR-520h | VEGFA | MMP2 | PGF | FGF2 (2) | EREG | ANGPT1 | TLR4 |
| miR-142-5p | NRP1 | JAG1 | FGF2 | ANGPT2 | IGF1 (2) | | |
| miR-203 | TIMP3 | NRP1 | NRP2 | FGF2 | EREG | TLR4 (2) | ABCA4 |

TABLE 3-continued

Predicted target genes of miRNAs altered during neovascularization. Genes with multiple predicted target interaction sites have the number of such sites indicated in parentheses following the gene name. Some genes had no targets predicted by the methods described in Example 9.

| miRNA | Predicted Target Genes | | | | | |
|---|---|---|---|---|---|---|
| miR-211 | MMP9 | NRP2 | FGF1 (2) | ANGPT1 | ELOVL4 | RDS |
| miR-145 | NRP1 | NRP2 | ANGPT2 | IGF1 | TLR4 | ELOVL4 |
| let-7b | IGF1 | ELOVL4 | | | | |
| miR-93 | VEGFA | MMP2 (2) | TIMP2 | FGF2 (2) | EREG | |
| miR-192 | EREG | IGF1 | | | | |
| miR-18a | IGF1 | | | | | |
| miR-223 | TIMP2 | FGF2 (2) | ABCA4 | EFEMP1 | | |
| miR-409 | | | | | | |
| miR-375 | | | | | | |
| miR-184 | | | | | | |

To determine if the number of angiogenesis target sites for the various miRNAs was significant, the inventors randomly selected twelve miRNAs and used the same list of genes and methodology to select potential angiogenesis related target genes. The average number of target sites for the randomly selected miRNAs was 2.7 or almost two fewer than was observed for the neovascularization-related miRNAs. The Student's t-test was used to calculate a p-value of 0.01, suggesting that the variance in the number of target gene predictions for the neovascularization associated miRNAs and the randomly-selected miRNAs is significant. A further indication of the significant difference between the lists of miRNAs is that only one of the randomly selected miRNAs was predicted to have at least two target sites for any single angiogenesis related gene.

TABLE 4

Predicted target genes of randomly selected miRNAs. Genes with multiple predicted target interaction sites have the number of such sites indicated in parentheses following the gene name. Some genes had no targets predicted by the methods described in Example 9.

| miRNA | Predicted Target Genes | | | | | |
|---|---|---|---|---|---|---|
| miR-24 | VEGFA | TIMP2 | NRP1 | NRP2 | EREG | RDS |
| miR-26a | JAG1 | EREG | IGF1 | TLR4 | EFEMP1 | |
| miR-103 | VEGFA | NRP2 | FGF2 | FGF2 | TLR4 | RS1 |
| miR-143 | NRP2 | FGF1 | | | | |
| miR-9 | EREG | ANGPT2 | ELOVL4 | | | |
| miR-124 | MMP2 | PFG | NRP1 | NRP2 | JAG1 | |
| miR-219-5p | TIMP3 | TLR4 | | | | |
| miR-377 | VEGFA | TIMP3 | NRP2 (2) | JAG1 | IGF1 | ABCA4 |
| miR-384 | TIMP2 | IGF1 | | | | |
| miR-7 | FBLN5 | TLR4 | | | | |
| miR-28-5p | PGF | ECGF1 | RS1 | | | |
| miR-601 | NRP2 | | | | | |
| miR-890 | TIMP3 (2) | | | | | |
| miR-99a | | | | | | |
| miR-202 | | | | | | |
| miR-323-50 | | | | | | |
| miR-126 | | | | | | |

REFERENCES

The following references, to the extent that they provide exemplary procedural or other details supplementary to those set forth herein, are specifically incorporated herein by reference.

U.S. Pat. No. 4,337,063
U.S. Pat. No. 4,404,289
U.S. Pat. No. 4,405,711
U.S. Pat. No. 4,659,774
U.S. Pat. No. 4,682,195
U.S. Pat. No. 4,683,202
U.S. Pat. No. 4,704,362
U.S. Pat. No. 4,816,571
U.S. Pat. No. 4,870,287
U.S. Pat. No. 4,959,463
U.S. Pat. No. 5,141,813
U.S. Pat. No. 5,143,854
U.S. Pat. No. 5,202,231
U.S. Pat. No. 5,214,136
U.S. Pat. No. 5,221,619
U.S. Pat. No. 5,223,618
U.S. Pat. No. 5,242,974
U.S. Pat. No. 5,264,566
U.S. Pat. No. 5,268,486
U.S. Pat. No. 5,288,644
U.S. Pat. No. 5,324,633
U.S. Pat. No. 5,378,825
U.S. Pat. No. 5,384,261
U.S. Pat. No. 5,399,363
U.S. Pat. No. 5,405,783
U.S. Pat. No. 5,411,876
U.S. Pat. No. 5,412,087
U.S. Pat. No. 5,413,924
U.S. Pat. No. 5,424,186
U.S. Pat. No. 5,428,148
U.S. Pat. No. 5,429,807

U.S. Pat. No. 5,432,049
U.S. Pat. No. 5,436,327
U.S. Pat. No. 5,445,934
U.S. Pat. No. 5,446,137
U.S. Pat. No. 5,466,786
U.S. Pat. No. 5,468,613
U.S. Pat. No. 5,470,710
U.S. Pat. No. 5,470,967
U.S. Pat. No. 5,472,672
U.S. Pat. No. 5,480,980
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,543,158
U.S. Pat. No. 5,545,531
U.S. Pat. No. 5,547,839
U.S. Pat. No. 5,550,044
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146
U.S. Pat. No. 5,580,726
U.S. Pat. No. 5,580,732
U.S. Pat. No. 5,583,013
U.S. Pat. No. 5,985,619
U.S. Pat. No. 5,593,839
U.S. Pat. No. 5,599,672
U.S. Pat. No. 5,599,695
U.S. Pat. No. 5,602,240
U.S. Pat. No. 5,602,244
U.S. Pat. No. 5,610,287
U.S. Pat. No. 5,610,289
U.S. Pat. No. 5,614,617
U.S. Pat. No. 5,623,070
U.S. Pat. No. 5,624,711
U.S. Pat. No. 5,631,134
U.S. Pat. No. 5,637,683
U.S. Pat. No. 5,639,603
U.S. Pat. No. 5,641,515
U.S. Pat. No. 5,645,897
U.S. Pat. No. 5,652,099
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,670,663
U.S. Pat. No. 5,672,697
U.S. Pat. No. 5,681,947
U.S. Pat. No. 5,695,940
U.S. Pat. No. 5,700,637
U.S. Pat. No. 5,700,922
U.S. Pat. No. 5,705,629
U.S. Pat. No. 5,708,154
U.S. Pat. No. 5,714,606
U.S. Pat. No. 5,728,525
U.S. Pat. No. 5,739,169
U.S. Pat. No. 5,744,305
U.S. Pat. No. 5,753,230
U.S. Pat. No. 5,760,395
U.S. Pat. No. 5,763,167
U.S. Pat. No. 5,766,591
U.S. Pat. No. 5,777,092
U.S. Pat. No. 5,792,847
U.S. Pat. No. 5,800,992
U.S. Pat. No. 5,801,005
U.S. Pat. No. 5,807,522
U.S. Pat. No. 5,824,311
U.S. Pat. No. 5,830,645
U.S. Pat. No. 5,830,880
U.S. Pat. No. 5,837,196
U.S. Pat. No. 5,846,225
U.S. Pat. No. 5,846,945
U.S. Pat. No. 5,847,219
U.S. Pat. No. 5,858,988
U.S. Pat. No. 5,859,221
U.S. Pat. No. 5,871,928
U.S. Pat. No. 5,872,232
U.S. Pat. No. 5,876,932
U.S. Pat. No. 5,886,165
U.S. Pat. No. 5,919,626
U.S. Pat. No. 5,985,619
U.S. Pat. No. 6,004,755
U.S. Pat. No. 6,087,102
U.S. Pat. No. 6,251,666
U.S. Pat. No. 6,368,799
U.S. Pat. No. 6,383,749
U.S. Pat. No. 6,403,341
U.S. Pat. No. 6,617,112
U.S. Pat. No. 6,638,717
U.S. Pat. No. 6,720,138
U.S. Patent Appln. 20080014196
U.S. Patent Appln. 20080039384
U.S. Patent Appln. 20080090750
U.S. Patent Appln. 20080096795
U.S. patent application Ser. No. 11/857,948
U.S. patent application Ser. No. 11/567,082
U.S. patent application Ser. No. 10/667,126
U.S. patent application Ser. No. 11/141,707
U.S. patent application Ser. No. 11/273,640
U.S. patent application Ser. No. 11/349,727
U.S. patent application Ser. No. 11/855,792
U.S. Patent appln. Ser. No. 60/575,743
U.S. Patent Prov. Ser. No. 60/649,584
Aiello et al., *Proc. Natl. Acad. Sci. USA.* 92(23):10457-10461, 1995.
Andersen et al., *Cancer Res.,* 64(15):5245-5250, 2004.
Austin-Ward and Villaseca, *Revista Medica de Chile,* 126(7): 838-845, 1998.
Bagga et al., *Cell,* 122(4):553-563, 2005.
Betel et al., *Nucleic Acids Res.* 36(Database Issue): D149-153, 2008.
Birney et al., *Genome Res.* 14(5):925-928, 2004
Brown and Regillo, *Am. J. Ophthalmol.,* 144(4):627-637, 2007.
Bukowski et al., *Clinical Cancer Res.,* 4(10):2337-2347, 1998.
Campochiaro and Hackett, *Oncogene.* 22(42):6537-6548, 2003.
Chang et al., *Vision Res.* 42(4):517-525, 2002.
Chen et al. *Mol. Endocrinol.,* 19:441-458, 2005.
Christodoulides et al., *Microbiology,* 144(Pt 11):3027-3037, 1998.
Davidson et al., *J. Immunother.,* 21(5):389-398, 1998.
EP 266,032
EP 373 203
EP 785 280
EP 799 897

Folkman, *N Engl J Med* 320:1211-1212, 1989.
Froehler et al., *Nucleic Acids Res.*, 14(13):5399-5407, 1986.
Griffiths-Jones et al., *Nucleic Acids Res.*, 34 (Database Issue): D140-D144, 2006.
Hanibuchi et al., *Int. J. Cancer*, 78(4):480-485, 1998.
Hellstrand et al., *Acta Oncologica*, 37(4):347-353, 1998.
Hui and Hashimoto, *Infection Immun.*, 66(11):5329-5336, 1998.
Itakura and Riggs, *Science*, 209:1401-1405, 1980.
John et al., *PLoS Biol.*, 3(7):e264, 2005.
Kornberg and Baker, In: *DNA Replication*, 2d Ed., Freeman, San Francisco, 1992.
Krek et al., *Nature Genetics*, 37:495-500, 2005.
Kwak et al., *Invest. Ophthalmol. Vis. Sci.*, 41(10):3158-3164, 2000.
Lewis et al., *Cell*, 120:15-20, 2005.
Lim et al., *Nature*, 433(7027):769-773, 2005.
Lima e Silva et al., *FASEB J.*, 21(12):3219-3230, 2007.
Miller et al., *Am. J. Pathol.*, 145(3):574-584, 1994.
Mori et al., *Am. J. Ophthalmol.*, 132(6):897-902, 2001.
Ozaki et al., *Am. J. Pathol.*, 156(2):697-707, 2000.
PCT Appln. WO 0138580
PCT Appln. WO 0168255
PCT Appln. WO 03020898
PCT Appln. WO 03022421
PCT Appln. WO 03023058
PCT Appln. WO 03029485
PCT Appln. WO 03040410
PCT Appln. WO 03053586
PCT Appln. WO 03066906
PCT Appln. WO 03067217
PCT Appln. WO 03076928
PCT Appln. WO 03087297
PCT Appln. WO 03091426
PCT Appln. WO 03093810
PCT Appln. WO 03100012
PCT Appln. WO 03100448A1
PCT Appln. WO 04020085
PCT Appln. WO 04027093
PCT Appln. WO 09923256
PCT Appln. WO 09936760
PCT Appln. WO 93/17126
PCT Appln. WO 95/11995
PCT Appln. WO 95/21265
PCT Appln. WO 95/21944
PCT Appln. WO 95/35505
PCT Appln. WO 96/31622
PCT Appln. WO 97/45137
PCT Appln. WO 97/10365
PCT Appln. WO 97/27317
PCT Appln. WO 9743450
PCT Appln. WO 99/35505
Pietras et al., *Oncogene*, 17(17):2235-2249, 1998.
Poliseno et al., *Blood* 108(9):3068-3071, 2006.
Qin et al., *Proc. Natl. Acad. Sci. USA*, 95(24):14411-14416, 1998.
Raymond et al., *RNA*, 11(11): 1737-1344, 2005.
Rehmsmeier et al., *RNA*, 10:1507-1517, 2004.
Remington's Pharmaceutical Sciences" 15th Edition, pages 1035-1038 and 1570-1580, 1990.
Rosenfeld et al., *Ophthalmol. Clin. North Am.* 19(3):361-372, 2006.
Sambrook et al., In: *DNA microaarays: a molecular cloning manual*, Cold Spring Harbor Laboratory Press, Cold Spring Harbor, N.Y., 2003.
Sambrook et al., In: *Molecular cloning: a laboratory manual*, $3^{rd}$ Ed., Cold Spring Harbor Laboratory Press, Cold Spring Harbor, N.Y., 2001.
Sambrook et al., In: *Molecular cloning: a laboratory manual*, $2^{nd}$ Ed., Cold Spring Harbor Laboratory Press, Cold Spring Harbor, N.Y., 1989.
Sargent et al., *J Clin Oncol.* 23:8664-8670, 2005
Sethupathy et al., *Nat. Methods.* 3(11):881-886, 2006.
Shen et al., *Gene Ther.* 13(3):225-234, 2006.
Shen et al., *Histol. Histopathol.* 22(12):1301-1308, 2007.
Smith et al., *Invest. Ophthalmol. Vis. Sci.* 35(1):101-111, 1994.
Tobe et al., *Invest. Ophthalmol. Vis. Sci.* 39:180-188, 1998.
U.K. Patent 1,529,202
U.K. Patent 8 803 000
White et al., *N Engl J Med* 320:1197-1200, 1989.
Yang et al., *J. Biol. Chem.* 280(10):9330-9335, 2005.

---

What is claimed is:

1. A method for reducing unwanted neovascularization in an individual in need thereof comprising administering to the individual a therapeutically-effective amount of an inhibitor of miR-21-comprising a single-stranded oligonucleotide that is complementary to a sequence of mature miR-21 (SEQ ID NO: 71).

2. The method of claim 1, wherein the inhibitor of miR-21 is 5, 6, 7, 8, 9, 10, 11, 12, 13, 14, 15, 16, 17, 18, 19, 20, 21, 22, 23, 24, 25, or 30 nucleotides in length.

3. The method of claim 1, wherein the inhibitor of miR-21 comprises a nucleotide analog or a modified nucleotide.

4. The method of claim 3, wherein the modified nucleotide comprises a sugar modification.

5. The method of claim 1, wherein the inhibitor of miR-21 is administered parenterally.

6. The method of claim 1, wherein the inhibitor of miR-21 has a sulfur modification.

* * * * *